United States Patent
Sommers et al.

(10) Patent No.: US 11,723,699 B2
(45) Date of Patent: Aug. 15, 2023

(54) SYSTEM AND METHOD FOR BONE FIXATION USING A NAIL LOCKED TO AN ENCIRCLING ANCHOR

(71) Applicant: Acumed LLC, Hillsboro, OR (US)

(72) Inventors: Mark B. Sommers, Beaverton, OR (US); Roy Werner Sanders, Tampa, FL (US); James G. Falkner, Jr., Beaverton, OR (US); Caleb Abraham Martin, Beaverton, OR (US); Zachary James Stroh, Winona Lake, IN (US); Scott Francis Mastroianni, Forest Grove, OR (US); Andrew William Seykora, Portland, OR (US); Ann Nicole Santich, Corvallis, OR (US); Larry W. Ehmke, Portland, OR (US); Oren S. Bernstein, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 36 days.

(21) Appl. No.: 16/935,799

(22) Filed: Jul. 22, 2020

(65) Prior Publication Data
US 2020/0345398 A1   Nov. 5, 2020

Related U.S. Application Data

(63) Continuation of application No. 16/153,460, filed on Oct. 5, 2018, now Pat. No. 10,758,280.
(Continued)

(51) Int. Cl.
*A61B 17/72*   (2006.01)
*A61B 17/88*   (2006.01)
(Continued)

(52) U.S. Cl.
CPC ...... *A61B 17/7233* (2013.01); *A61B 17/1615* (2013.01); *A61B 17/1725* (2013.01);
(Continued)

(58) Field of Classification Search
CPC .................. A61B 17/72–7291; A61B 17/921
See application file for complete search history.

(56) References Cited

U.S. PATENT DOCUMENTS 3,763,855 A * 10/1973 McAtee ................. A61B 17/72
   606/64
4,697,585 A * 10/1987 Williams ............... A61B 17/72
   606/64
(Continued)

FOREIGN PATENT DOCUMENTS

FR      2690330 A1   10/1993
JP    2003-533327 A  11/2003
(Continued)

OTHER PUBLICATIONS

Supplementary European Search Report corresponding to EP Application No. 18866037.7; report dated Jun. 11, 2021; 14 pages.
(Continued)

*Primary Examiner* — Eduardo C Robert
*Assistant Examiner* — Michelle C Eckman
(74) *Attorney, Agent, or Firm* — K&L Gates LLP

(57) ABSTRACT

Systems and methods for fixing bone using an intramedullary nail locked to an encircling anchor including a bushing and a locking member. An exemplary system may include any combination of the nail, one or more bushings, one or more locking members, an instrument to guide installation of the bushing, at least one drill, and a driver that attaches to the bushing. The instrument may define a guide axis and be configured to be coupled to a bone such that the guide axis extends across the bone. The instrument may be used to
(Continued)

guide a drill, the bushing, and/or the locking member along the guide axis into the bone. The nail may be configured to be placed along the medullary canal of the bone such that the nail extends through the bushing, and the locking member may be configured to lock the nail to the bushing.

20 Claims, 23 Drawing Sheets

Related U.S. Application Data

(60) Provisional application No. 62/569,955, filed on Oct. 9, 2017.

(51) Int. Cl.
<table>
<tr><td>A61B 17/86</td><td>(2006.01)</td></tr>
<tr><td>A61B 17/16</td><td>(2006.01)</td></tr>
<tr><td>A61B 17/17</td><td>(2006.01)</td></tr>
<tr><td>A61B 17/00</td><td>(2006.01)</td></tr>
<tr><td>A61B 90/00</td><td>(2016.01)</td></tr>
<tr><td>A61B 17/90</td><td>(2006.01)</td></tr>
</table>

(52) U.S. Cl.
CPC .......... *A61B 17/725* (2013.01); *A61B 17/86* (2013.01); *A61B 17/88* (2013.01); *A61B 17/8866* (2013.01); *A61B 17/90* (2021.08); *A61B 2017/0092* (2013.01); *A61B 2017/00477* (2013.01); *A61B 2090/061* (2016.02)

(56) References Cited

U.S. PATENT DOCUMENTS

| | | | |
|---|---|---|---|
| 5,697,933 A | 12/1997 | Gundlapalli et al. | |
| 6,221,074 B1* | 4/2001 | Cole | A61B 17/72 606/60 |
| 6,562,042 B2* | 5/2003 | Nelson | A61B 17/1721 606/328 |
| 10,758,280 B2* | 9/2020 | Sommers | A61B 17/1725 |
| 2004/0122428 A1* | 6/2004 | Johnstone | A61B 17/1725 606/62 |
| 2004/0167533 A1 | 8/2004 | Wilson et al. | |
| 2006/0084997 A1 | 4/2006 | Dejardin | |
| 2007/0088360 A1 | 4/2007 | Orbay et al. | |
| 2007/0100342 A1* | 5/2007 | Green | A61B 17/725 606/64 |
| 2007/0299451 A1 | 12/2007 | Tulkis | |
| 2008/0183179 A1 | 7/2008 | Siebel et al. | |
| 2009/0062797 A1* | 3/2009 | Huebner | A61B 17/1739 606/151 |
| 2010/0137863 A1* | 6/2010 | Munro | A61B 17/8872 606/64 |
| 2012/0197291 A1 | 8/2012 | Tsai et al. | |
| 2014/0135850 A1 | 5/2014 | Parent et al. | |
| 2014/0222002 A1 | 8/2014 | Maxson | |
| 2016/0361100 A1* | 12/2016 | Savage | A61B 17/744 |
| 2018/0078294 A1* | 3/2018 | Hedgeland | A61B 17/1725 |

FOREIGN PATENT DOCUMENTS

| | | |
|---|---|---|
| JP | 2019-502523 A | 1/2019 |
| WO | 95014176 A1 | 5/1995 |
| WO | 2009029798 A1 | 3/2009 |
| WO | 2017120327 A2 | 7/2017 |

OTHER PUBLICATIONS

Extended European Search Report corresponding to EP Application No. 18866037.7; report dated Sep. 24, 2021; 14 pages.
First Japanese Office Action corresponding to related Japanese Application No. 2020-521315 dated Sep. 12, 2022, 15 pages.
First Chinese Office Action corresponding to related Chinese Application No. 2018800793264 dated Jan. 19, 2023, 23 pages.
Second Japanese Office Action corresponding to related Japanese Application No. 2020-521315 dated Jan. 23, 2023, 6 pages.

* cited by examiner

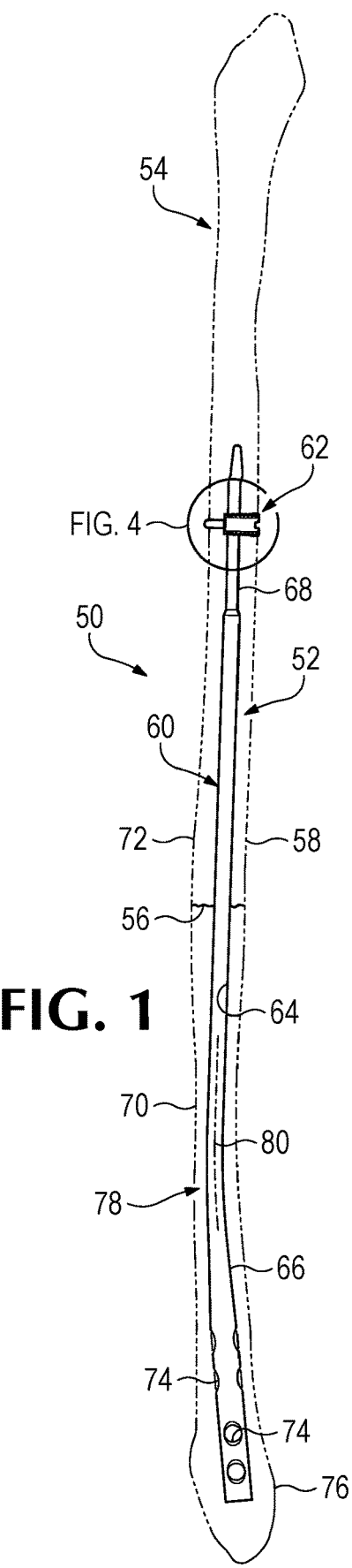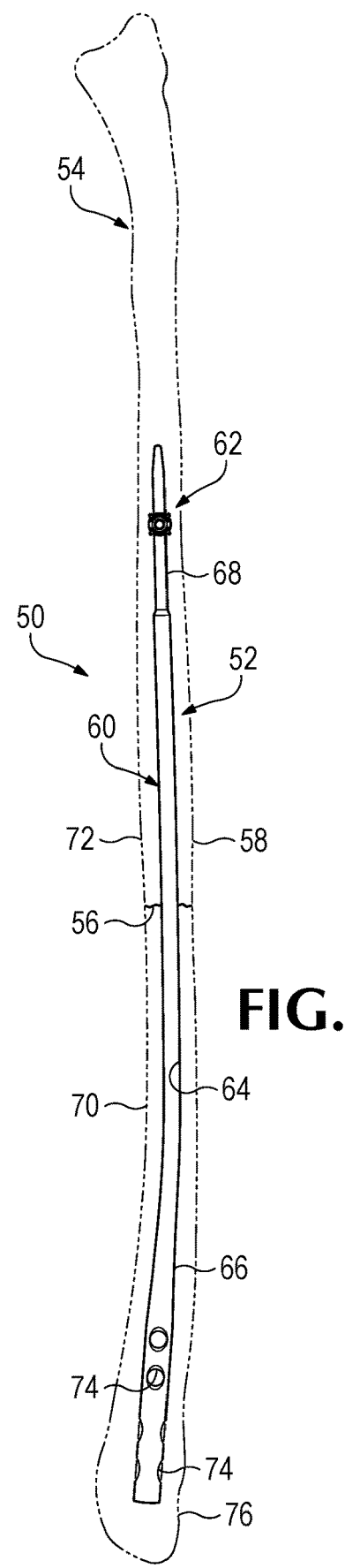

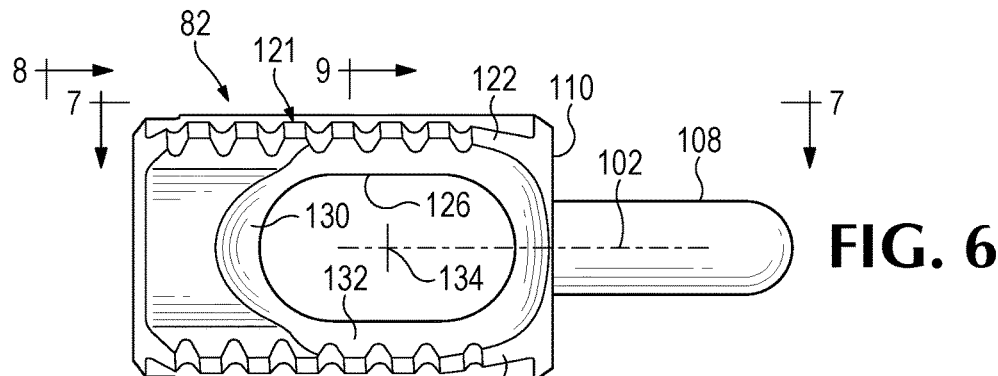
FIG. 6
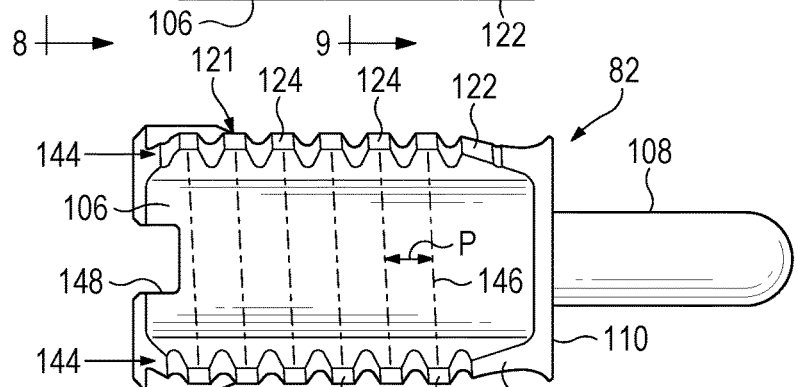
FIG. 7
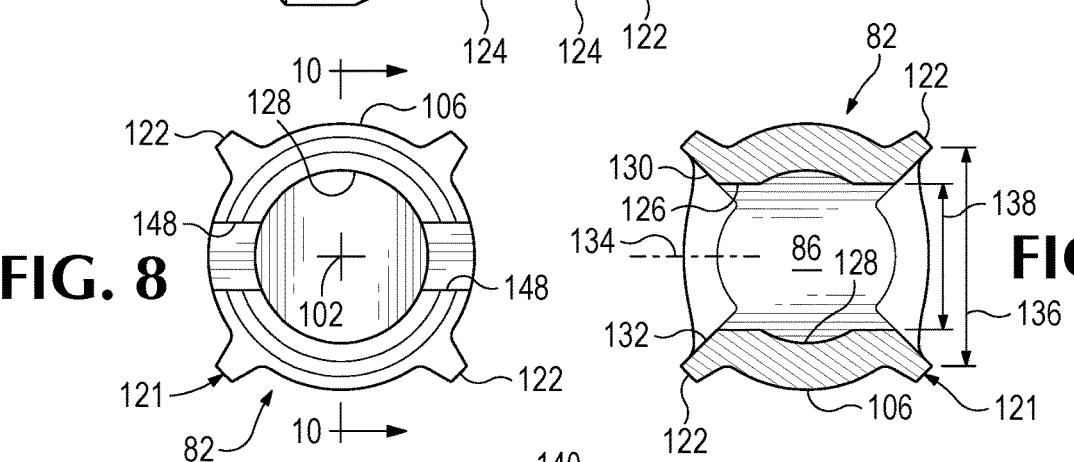
FIG. 8
FIG. 9
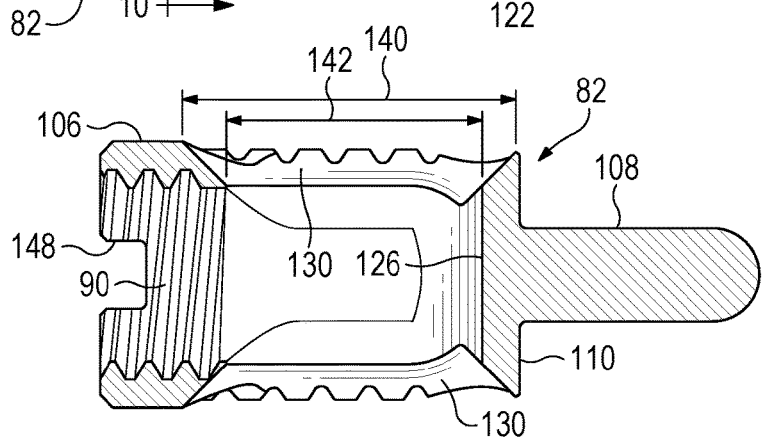
FIG. 10

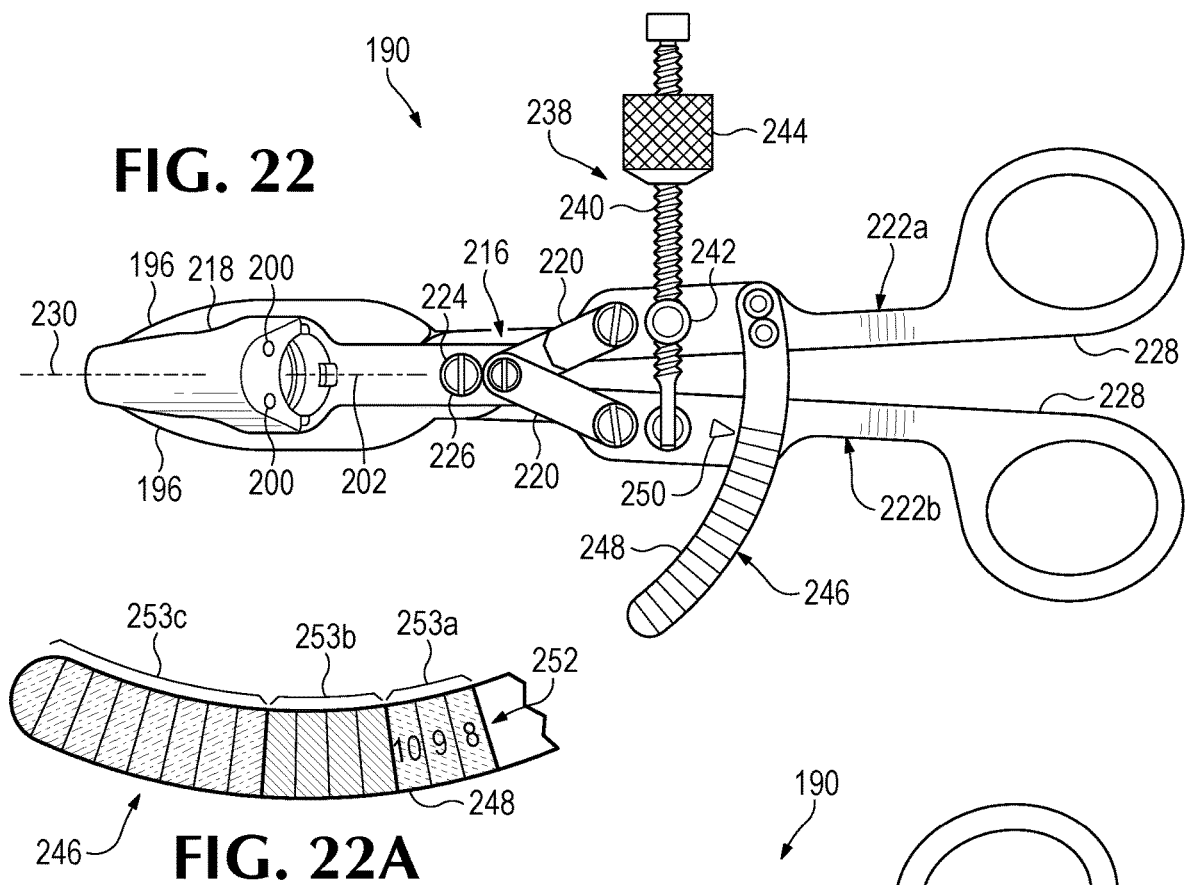
FIG. 22
FIG. 22A
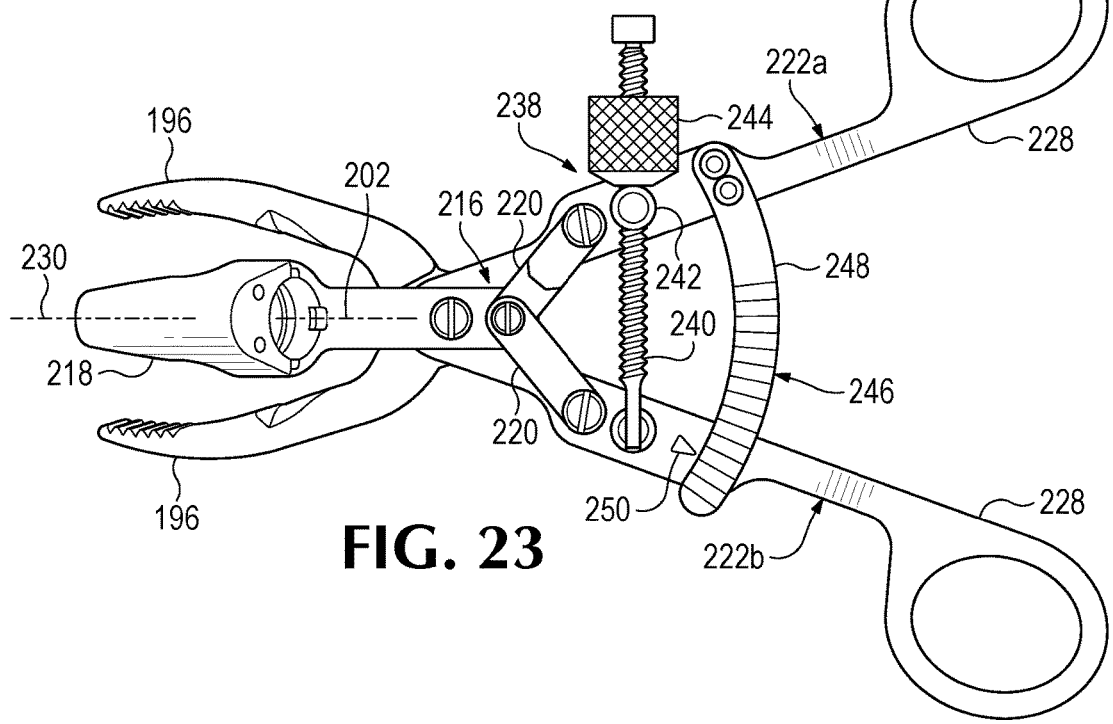
FIG. 23

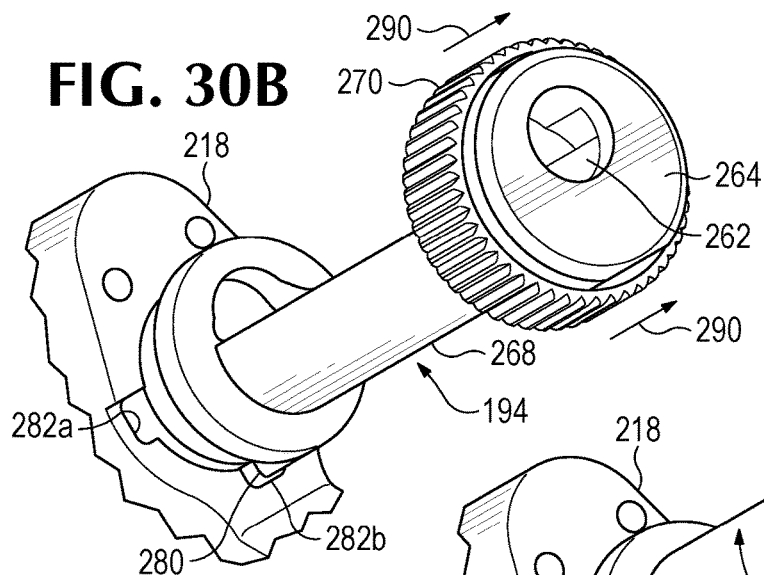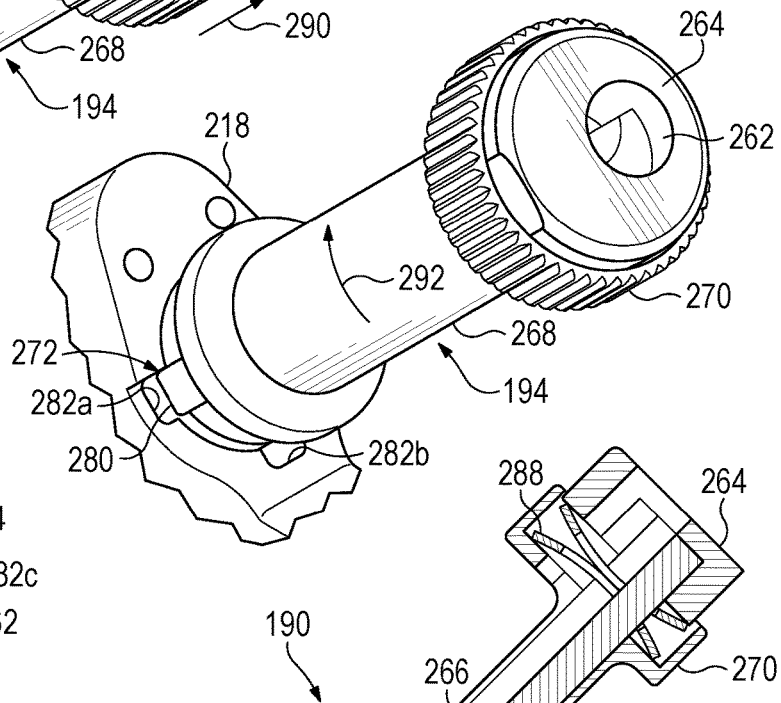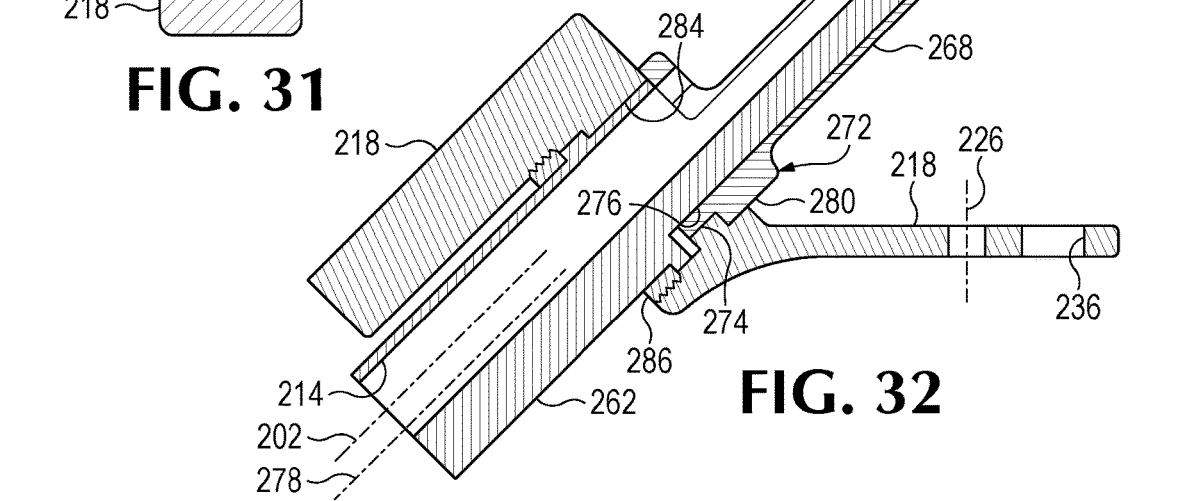

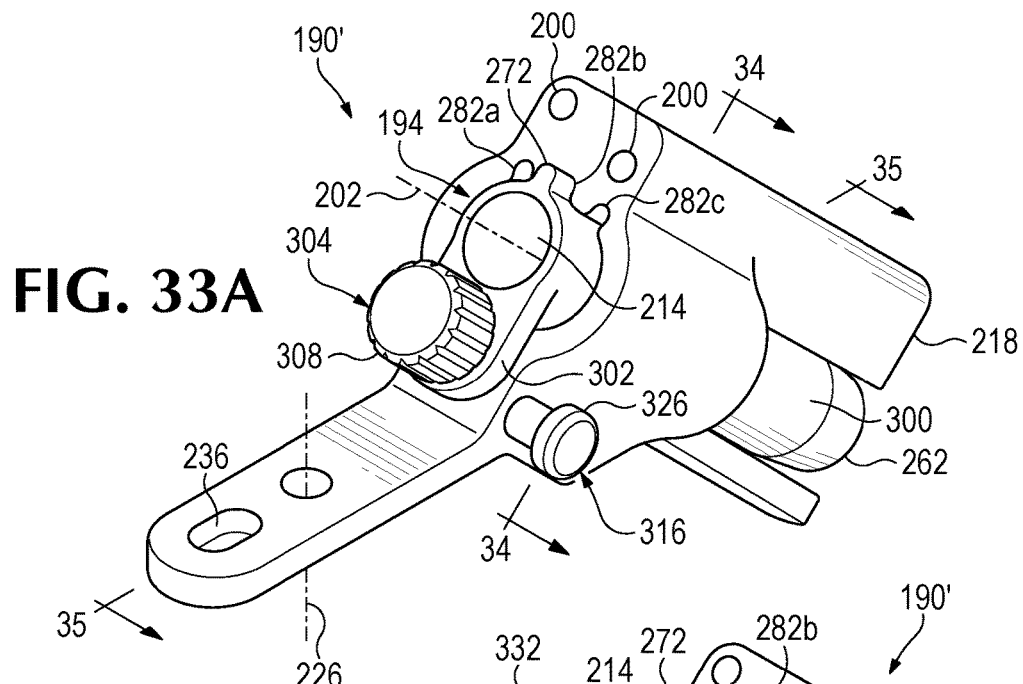
FIG. 33A
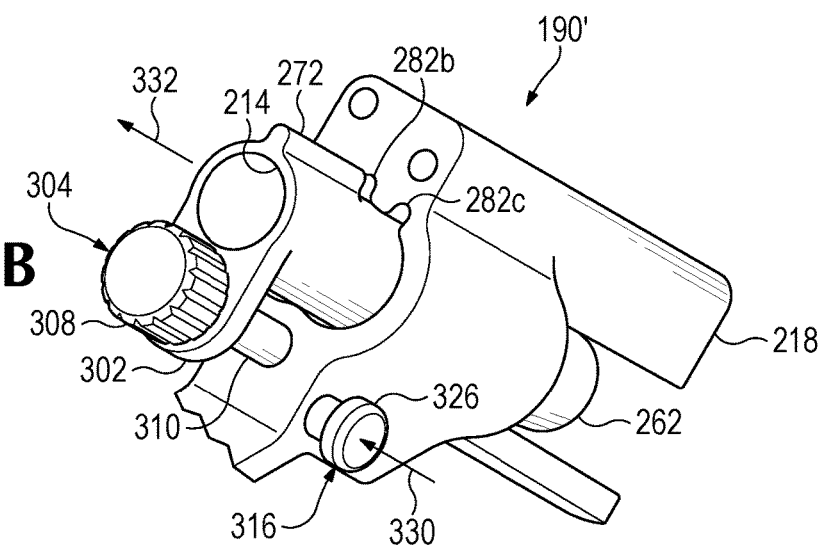
FIG. 33B
FIG. 33C

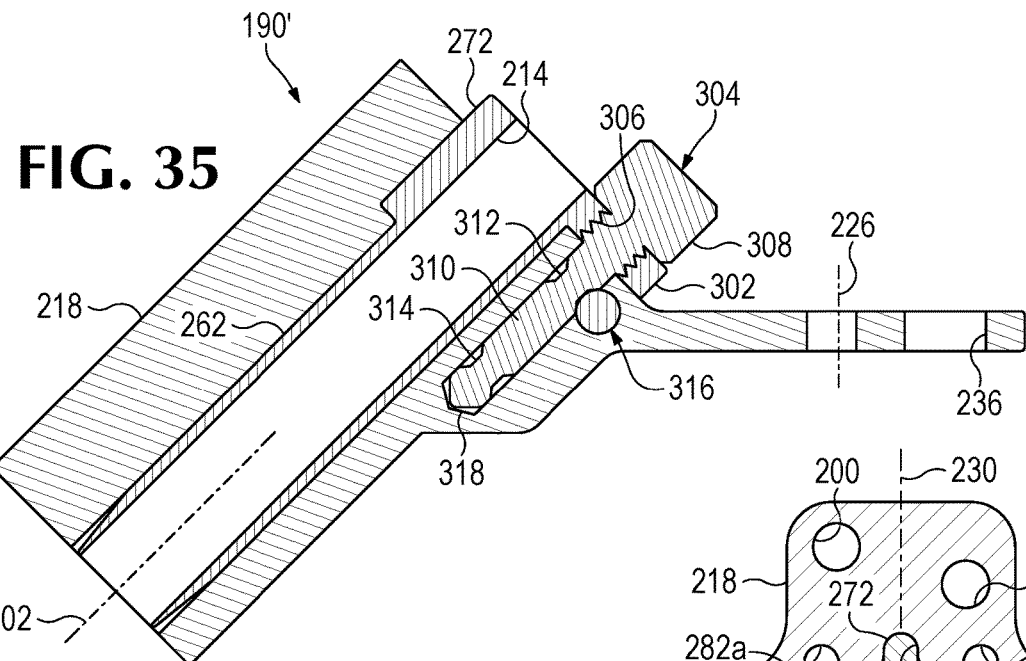
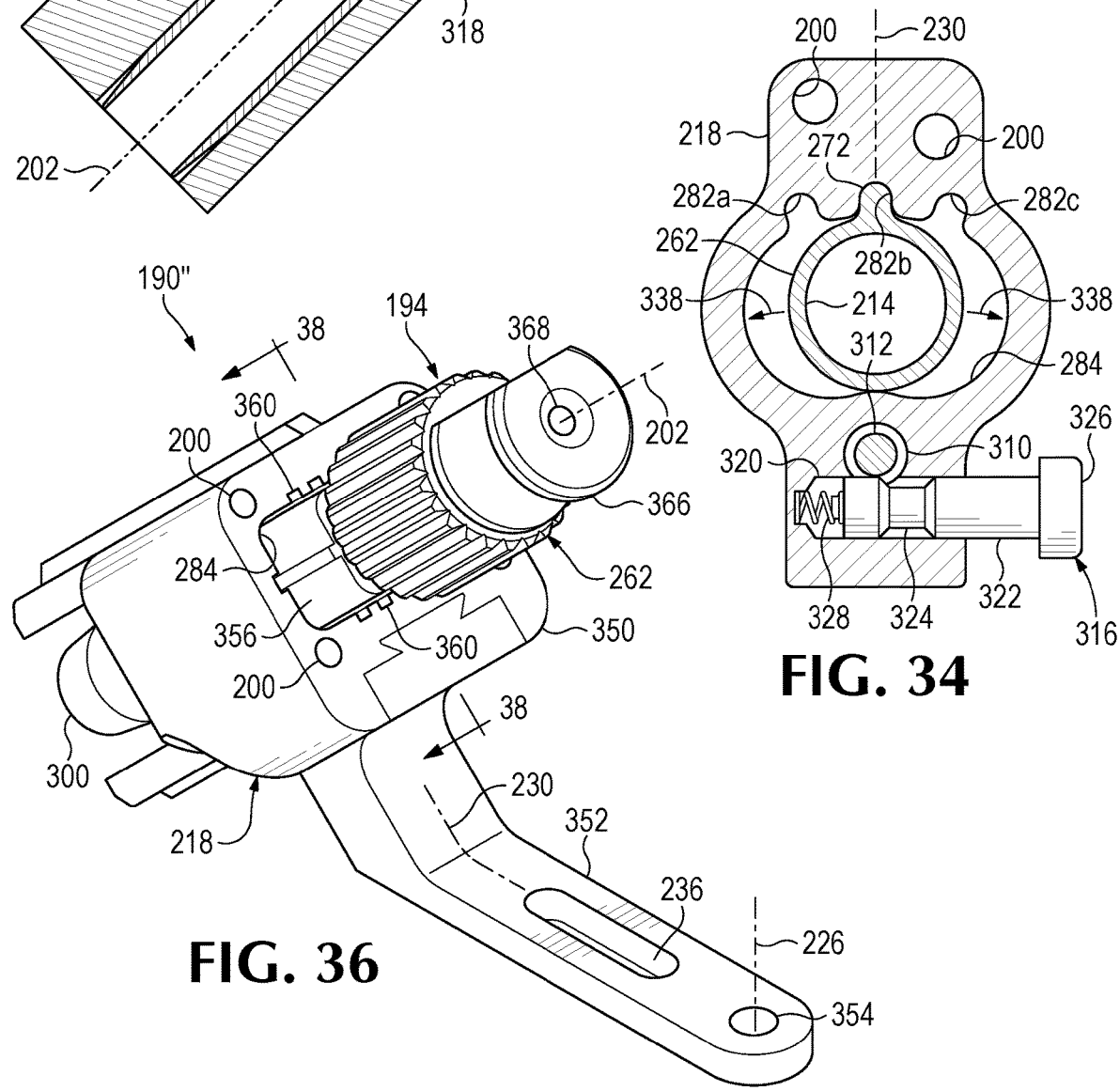

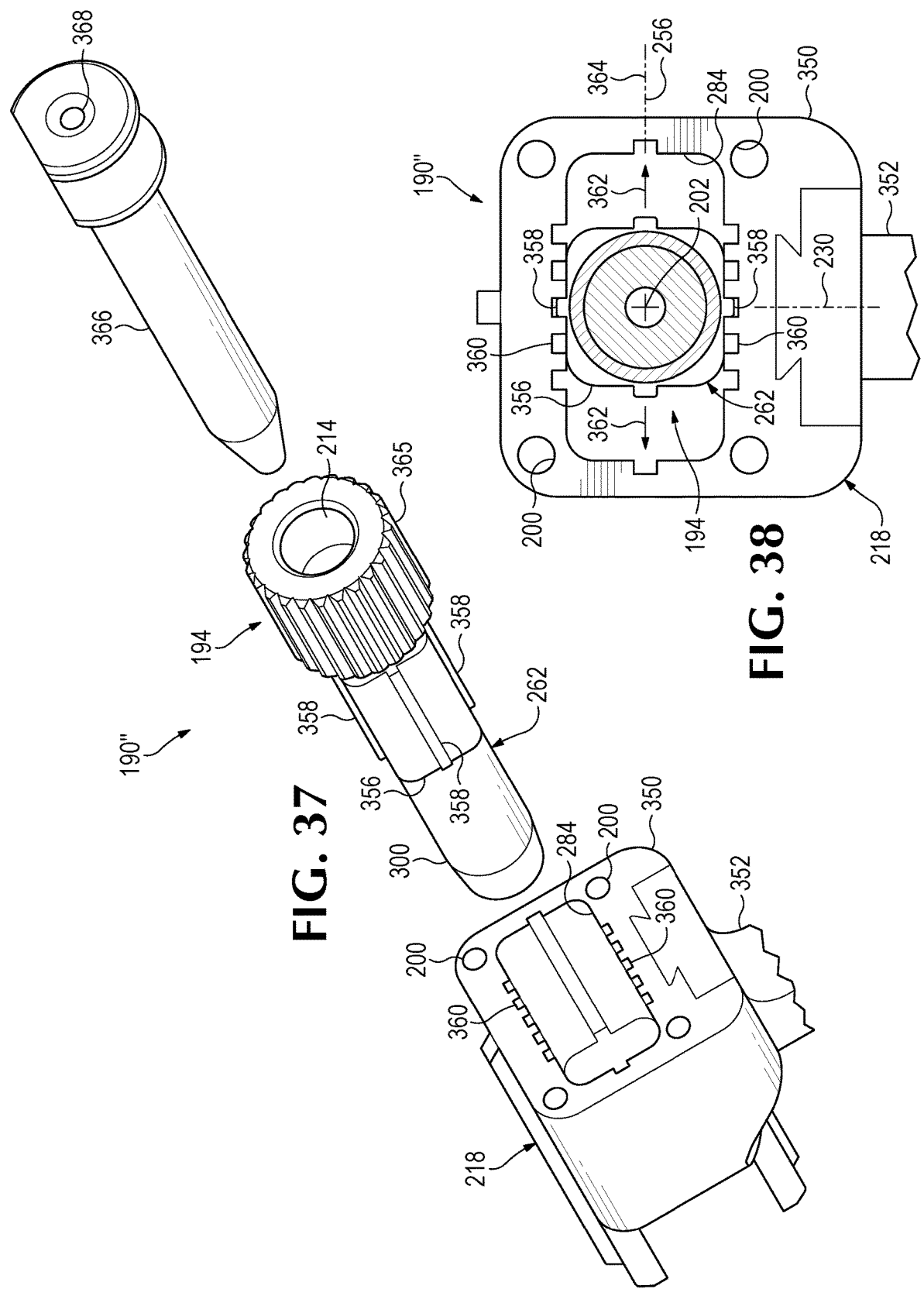

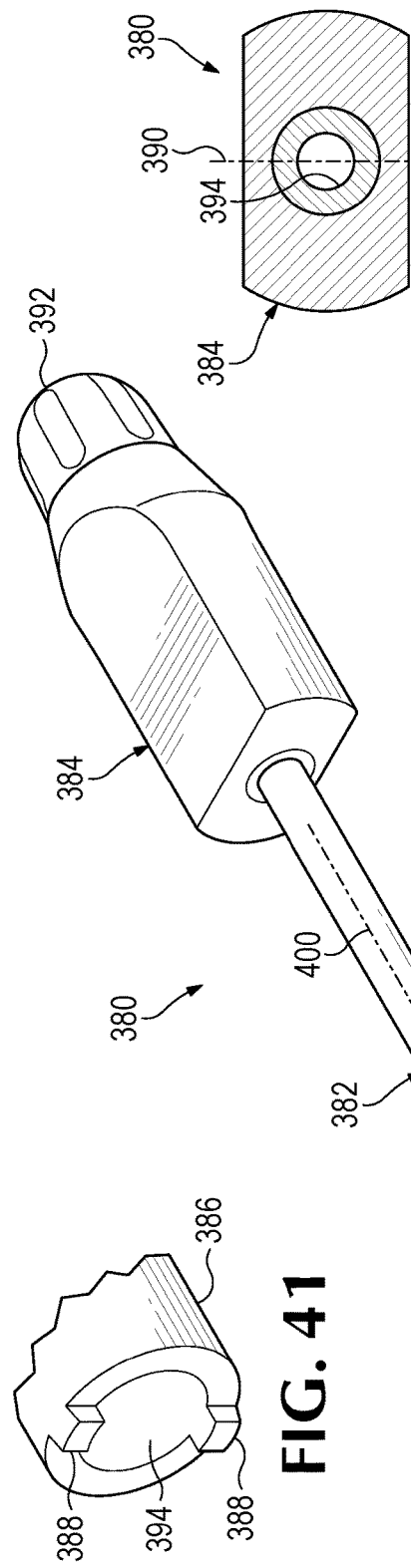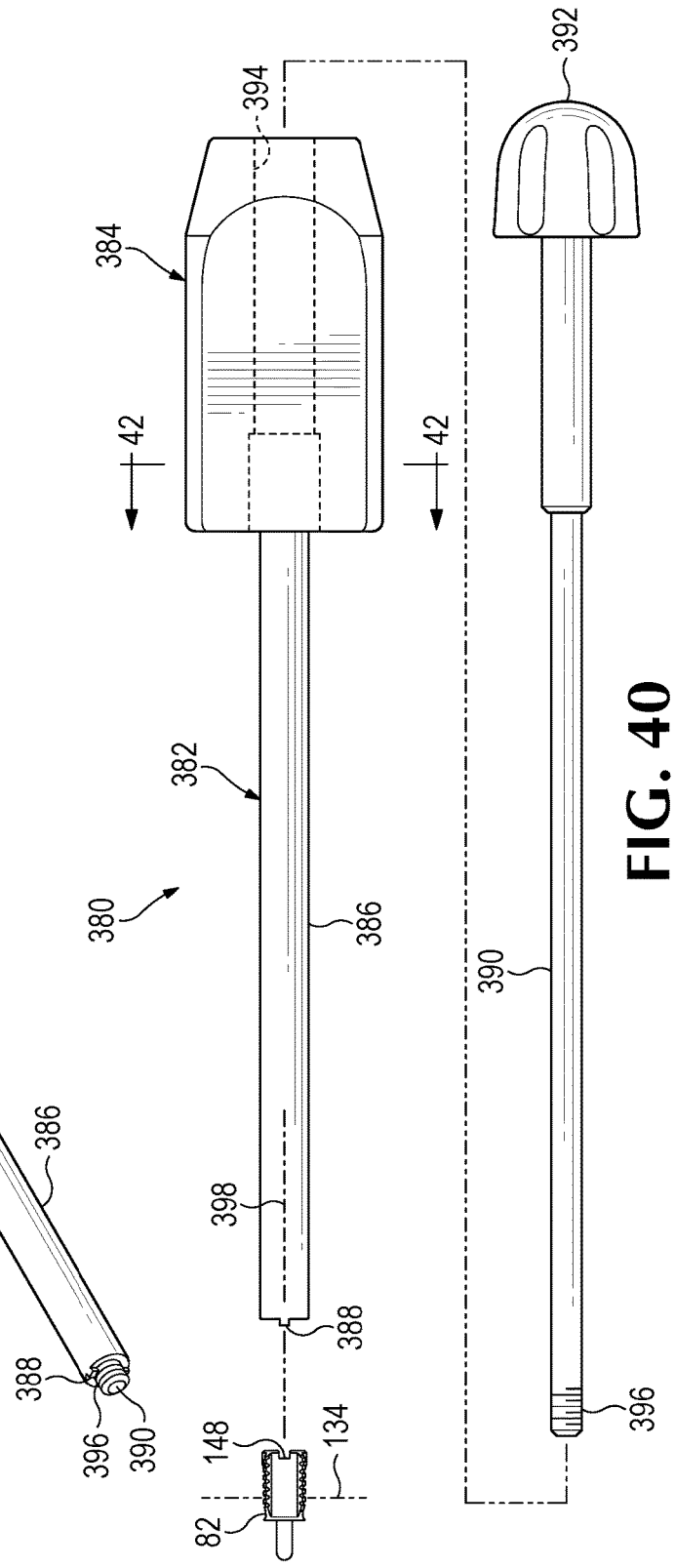

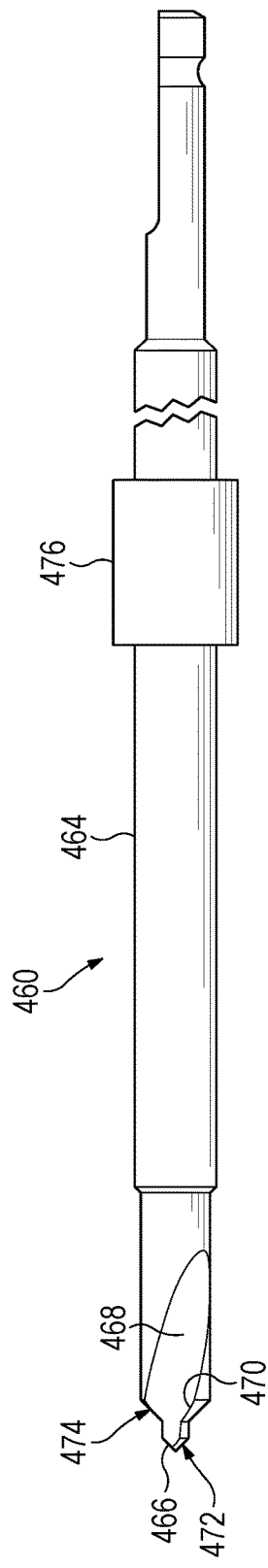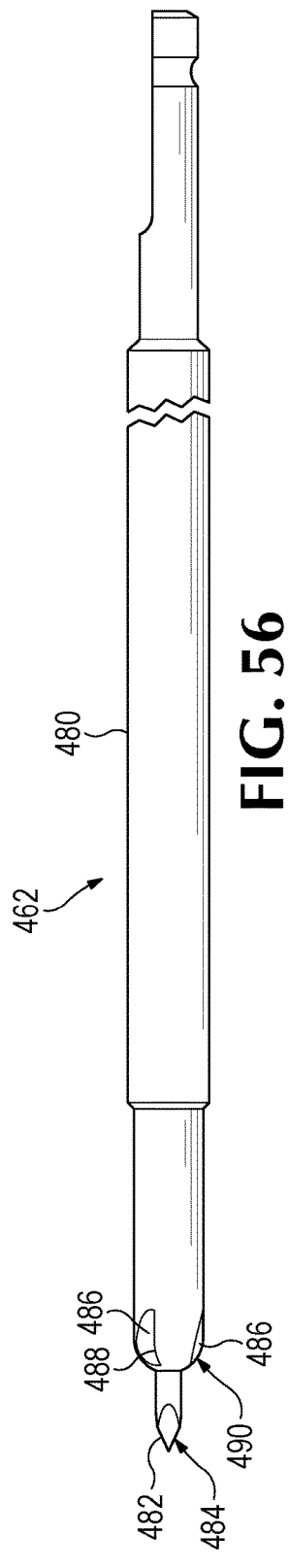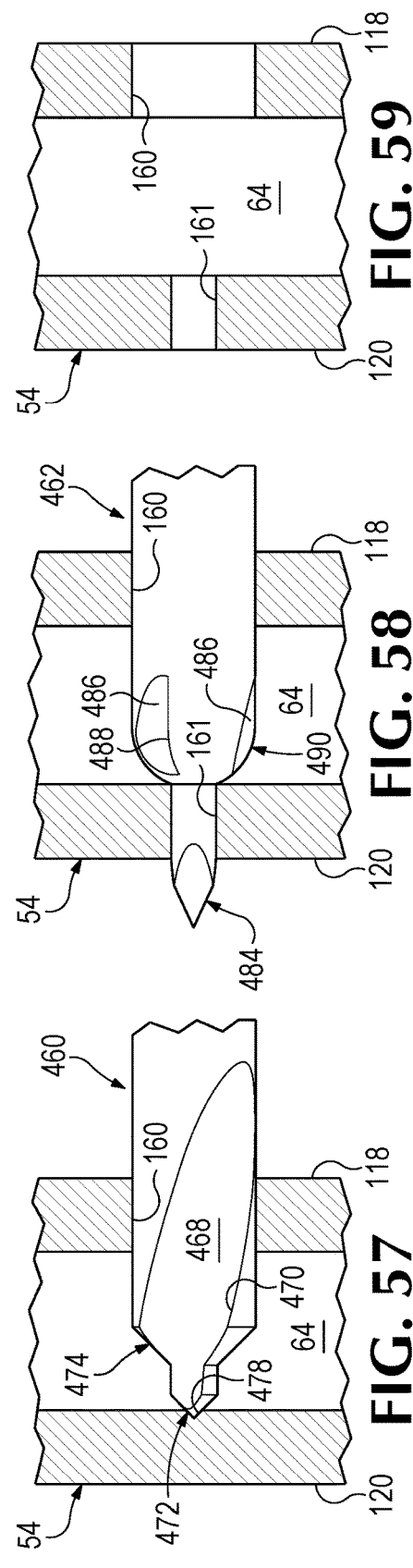

SYSTEM AND METHOD FOR BONE FIXATION USING A NAIL LOCKED TO AN ENCIRCLING ANCHOR

CROSS-REFERENCE TO PRIORITY APPLICATIONS

The present application is a continuation of application Ser. No. 16/153,460 filed on Oct. 5, 2018, which claims the benefit of U.S. Provisional Patent Application Ser. No. 62/569,955, filed Oct. 9, 2017, which is incorporated herein by reference in its entirety for all purposes.

INTRODUCTION

An intramedullary (IM) nail is an internal fixation device that can be placed along the medullary canal of a fractured bone. The nail acts as a splint inside the bone to keep segments of the bone aligned as healing occurs. A standard, double-locking nail defines a plurality of apertures near its opposite ends to receive screws that lock both ends of the nail to bone. However, some bones, such as the fibula and ulna, can be too narrow to receive a standard nail without excessive reaming. For these bones, a slender, single-locking nail may be installed instead. The single-locking nail has a head defining apertures for screws, and a stem that is too thin to receive screws. Accordingly, one end of the nail (the head) is locked to the bone, but the other end (the stem) remains unlocked. If the bone is fractured at a position spanned by the stem, the nail may permit movement of bone segments relative to one another. For this type of fracture, the bone could be stabilized more effectively if the surgeon had the option of also locking the stem to the bone.

U.S. Pat. No. 7,785,326 proposes a nail-based fixation system in which a nail extends through, and is locked to, a fastener. More particularly, the system utilizes an installation jig that requires the nail to travel a linear path during advancement into bone, until the leading end of the nail has entered a hole of the fastener. However, this system is unsuitable for locking the stem of a nonlinear and/or flexible nail to bone at a substantial distance from the site of entry of the nail into the bone.

SUMMARY

The present disclosure provides systems and methods for fixing bone using an intramedullary nail locked to an encircling anchor including a bushing and a locking member. An exemplary system may include any combination of the nail, one or more bushings, one or more locking members, an instrument to guide installation of the bushing, at least one drill, and a driver that attaches to the bushing. The instrument may define a guide axis and be configured to be coupled to a bone such that the guide axis extends across the bone. The instrument may be used to guide a drill, the bushing, and/or the locking member along the guide axis into the bone. The nail may be configured to be placed along the medullary canal of the bone, such that the nail extends through the bushing, and the locking member may be configured to lock the nail to the bushing.

BRIEF DESCRIPTION OF THE DRAWINGS

FIG. 1 is an anterior view of a fractured left fibula (in phantom) fixed with an intramedullary nail locked to an encircling anchor, but with fasteners for a trailing region of the nail omitted, in accordance with aspects of the present disclosure.

FIG. 2 is a lateral view of the fractured left fibula of FIG. 1, taken with the nail and encircling anchor installed as in FIG. 1.

FIG. 6 is a side view of a bushing of the anchor of FIG. 1.

FIG. 7 is another side view of the bushing of FIG. 1, taken along line 7-7 of FIG. 6.

FIG. 8 is an end view of the bushing of FIG. 1, taken along line 8-8 of FIG. 6.

FIG. 9 is a sectional view of the bushing of FIG. 1, taken along line 9-9 of FIG. 6.

FIG. 10 is another sectional view of the bushing of FIG. 1, taken along line 10-10 of FIG. 8.

FIG. 22 is a top view of the instrument of FIG. 21, taken in the absence of a guide portion of the instrument and with jaws of the instrument in a closed configuration.

FIG. 22A is a fragmentary view of the instrument of FIG. 21 showing a portion of a gauge of the instrument.

FIG. 23 is another top view of the instrument of FIG. 21, taken as in FIG. 22 but with the jaws of the instrument in an open configuration.

FIG. 30B is a fragmentary, isometric view of the guide portion and holder of FIG. 30A, taken with the guide portion in an unlocked configuration that permits rotation of the guide portion with respect to the holder.

FIG. 30C is another fragmentary, isometric view of the guide portion and holder of FIG. 30A, taken after rotation of the guide portion with respect to the holder (compare with FIG. 30B), while the guide portion is still in an unlocked configuration.

FIG. 31 is a sectional view of the guide portion and holder of FIG. 30A, taken generally along line 31-31 of FIG. 30A and showing, in phantom, alternative locked positions of the guide portion.

FIG. 32 is a sectional view of the guide portion and holder of FIG. 30A, taken generally along line 32-32 of FIG. 30A.

FIG. 33A is an isometric view of another exemplary guide portion and holder for the instrument of FIG. 21, taken in isolation from the rest of the instrument with the guide portion in a locked configuration that prevents movement with respect to the holder, in accordance with aspects of the present disclosure.

FIG. 33B is another isometric view of the guide portion and holder of FIG. 33A, taken as in FIG. 33A, except with the holder fragmentary and with the guide portion retracted to produce an unlocked configuration.

FIG. 33C is another isometric, fragmentary view of the guide portion and holder of FIG. 33A, taken as in FIG. 33B with the guide portion retracted and in an unlocked configuration, except with the guide portion rotated.

FIG. 34 is a sectional view of the guide portion and holder of FIG. 33A, taken generally along line 34-34 of FIG. 33A.

FIG. 35 is another sectional view of the guide portion and holder of FIG. 33A, taken generally along line 35-35 of FIG. 33A.

FIG. 36 is an isometric view of yet another exemplary guide portion and holder for the instrument of FIG. 21, taken in isolation from the rest of the instrument, in accordance with aspects of the present disclosure.

FIG. 37 is an exploded, fragmentary view of the guide portion and holder of FIG. 36.

FIG. 38 is a sectional view of the guide portion of FIG. 36, taken generally along line 38-38 of FIG. 36.

FIG. 39 is an isometric view of an exemplary driver for the bushings of FIG. 14.

FIG. 40 is an exploded view of the driver of FIG. 39 with one of the bushings of FIG. 14 aligned with the driver.

FIG. 41 is a fragmentary view of a sleeve of the driver of FIG. 39, taken around the leading end of the sleeve and showing protrusions that mate with complementary recesses of each bushing.

FIG. 42 is a sectional view of the driver of FIG. 39, taken generally along line 42-42 of FIG. 40 through a handle portion of the driver.

FIG. 55 is a side view of an exemplary near-cortex drill for use in a two-drill procedure for boring holes in a bone to receive a bushing, with the near-cortex drill configured to be guided into the bone using any of the guide instruments disclosed herein.

FIG. 56 is a side view of an exemplary far-cortex drill that can be used with the near-cortex drill of FIG. 55 in a two-drill procedure for boring holes in a bone to receive a bushing.

FIGS. 57-59 are fragmentary sectional views of a bone illustrating how the drills of FIGS. 55 and 56 can sequentially bore holes of different diameter to receive correspondingly-sized regions of a bushing.

DETAILED DESCRIPTION

Figure 3:
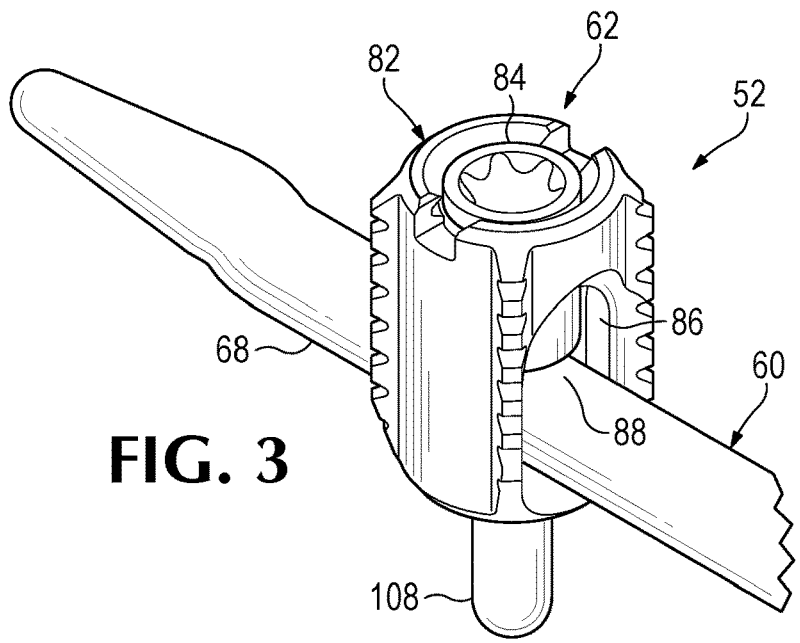
FIG. 3 is a fragmentary, isometric view of the nail and encircling anchor of FIG. 1, taken around the anchor.

The present disclosure provides systems and methods for fixing bone using an intramedullary nail locked to an encircling anchor including a bushing and a locking member. An exemplary system may include any combination of the nail, one or more bushings, one or more locking members, an instrument to guide installation of the bushing, at least one drill, and a driver that attaches to the bushing. The instrument may define a guide axis and be configured to be coupled to a bone such that the guide axis extends across the bone. The instrument may be used to guide a drill, the bushing, and/or the locking member along the guide axis into the bone. The nail may be configured to be placed along the medullary canal of the bone, such that the nail extends through the bushing, and the locking member may be configured to lock the nail to the bushing.

An exemplary system for bone fixation is provided. The system may comprise an instrument, a bushing, a nail, and a locking member. The instrument may have a pair of jaws configured to engage opposite sides of a shaft of a long bone. The jaws may be coupled to a guide portion defining a guide axis. The guide axis may extend across the shaft of the bone when the jaws are engaged with the shaft of the bone. The instrument may be configured to maintain the guide in a central plane that is between and equidistant from the jaws as the jaws are opened and closed. The bushing may be configured to be placed transversely into the bone along the guide axis. The nail may be configured to be placed along a medullary canal of the bone such that the nail extends through the bushing. The locking member may be configured to lock the nail to the bushing. In some embodiments, the instrument may be configured to permit the guide axis to be adjustably offset from the central plane, if needed. In some embodiments, the instrument may be configured to direct a wire member into/through the bone to couple the instrument to the bone. For example, the leading ends of a pair of wire members may be directed on non-parallel trajectories through the bone, to stabilize the instrument on the bone. In some embodiments, the instrument may include a gauge configured to measure a local width of the bone, and optionally to indicate whether the local width is sufficient for safe installation of the bushing. In some embodiments, the bushing may form a shoulder configured to impede advancement of the bushing when the shoulder contacts a far cortex of the bone. The bushing also may form a post projecting distally from the shoulder. In some embodiments, the nail may have an offset tip configured to permit adjustment of the alignment of the nail with a transverse aperture of the bushing when the nail is rotated about its long axis.

An exemplary method of fixing bone is provided. In the method, opposite sides of a bone may be engaged with jaws of an instrument having a guide portion defining a guide axis. The jaws may be coupled or configured to be coupled to the guide portion such that the guide axis remains in a central plane that is between and equidistant from the jaws as the jaws are opened and closed. At least one hole may be bored transversely in the bone along the guide axis. A bushing may be placed into the bone at the at least one hole. A nail may be advanced along a medullary canal of the bone such that the nail extends through the bushing. The nail may be locked to the bushing.

Another exemplary method of fixing bone is provided. In the method, a bone may be bored along an axis to form a wider hole through a near cortex and a narrower hole in and/or through a far cortex of the bone. A bushing may be selected. The bushing may have a trailing portion with a diameter corresponding to the wider hole and a leading portion with a diameter corresponding to the narrower hole. The trailing portion may form a shoulder adjacent the leading portion. The bushing may be driven as a unit into the bored bone along the axis until contact between the shoulder and the far cortex impedes further advancement of the bushing. A nail may be advanced along the medullary canal such that the nail extends through the bushing. The nail may be locked to the bushing.

The systems and methods of the present disclosure may offer any combination of the following features and advantages. Installation of the bushing may be performed more reliably using an instrument with a self-centering guide axis. The jaws of the clamp may be inserted through an incision and under soft tissue that covers opposite sides of the bone, to engage regions of the bone that are not visible to the surgeon. Accordingly, even if the surgeon cannot determine where the transverse center of the bone is visually, a self-centering configuration of the instrument can ensure that the guide axis extends across the bone very close to the transverse center. Also, the systems and methods can reliably align the leading end of the nail inside bone with a transverse aperture defined by the bushing, even when the nail is flexible/curved and/or when the bushing is positioned far from the site of nail entry. The nail is successfully mated with the bushing when the trajectory of the nail intersects the transverse aperture of the bushing. The systems and methods can properly position a guide axis along which the bushing is installed. For example, an instrument defining the guide axis may be self-centering on the bone, as described above, and/or may permit movement of the guide axis off-center, if needed, while the instrument remains attached to the bone. The instrument may be coupled to the bone with one or more wire members, in addition to or instead of using jaws of the instrument. (The jaws thus may be omitted from the design of the instrument.) The systems and methods may install or be configured to install the bushing along the guide axis such that the bushing has an optimal position along the guide axis. For example, the bushing may have a shoulder that stops advancement of the bushing through contact with the far cortex of the bone to set the position of the bushing along the guide axis. This configuration may place a distal end of the transverse aperture very near the far cortex. The transverse aperture may be elongated parallel to the long axis of the bushing (to form a slot), such that the transverse aperture substantially spans the medullary canal (in a direction across the canal) when the bushing is installed in a bone. In some embodiments, the size of the transverse aperture may be selected by choosing a bushing from a set of bushings having respective transverse apertures of different length (measured parallel to the long axes of the bushings). The width of the transverse aperture may be substantially maximized using a bevel, which may be formed in part by a protrusion on the bushing, to further increase the reliability of successful mating of the nail with the bushing.

Further aspects of the present disclosure are described in the following sections: (I) overview of implanted components of the fixation system, (II) anchors, (III) nail with offset tip, (IV) instrument, (V) driver, (VI) methods of fixing bone, (VII) composition of system components, and (VIII) examples.

I. OVERVIEW OF IMPLANTED COMPONENTS OF THE FIXATION SYSTEM

This section provides an overview of exemplary implanted components for a fixation system 50 of the present disclosure; see FIGS. 1-5.

FIGS. 1 and 2 show a fixation assembly 52 of the fixation system implanted in a left fibula 54 having a fracture 56 in a shaft region 58 of the bone. The fixation assembly may include an intramedullary nail 60 that spans at least one fracture 56 and extends through an anchor 62 for the nail. The anchor may encircle and lock to the nail and attach the nail to the bone. Nail 60 may be arranged longitudinally in the bone and particularly a medullary canal 64 thereof, with the long axes of the nail and the bone substantially aligned with one another (e.g., parallel and/or coincident). Anchor 62 may be implanted transversely in the bone (e.g., bicortically) and may span the medullary canal crosswise. The anchor alternatively may be described as an implant or, in some embodiments, as an external fastener (i.e., external to the nail).

Nail 60 is elongated and may have a trailing region 66 and a leading region 68, each of which also may be elongated. Trailing and leading regions 66, 68 may be contiguous with one another, or may be separated by an intermediate region of the nail. Regions 66, 68 may form opposite leading and trailing ends of the nail and may be formed integrally with one another. The leading region may have a smaller diameter (e.g., a smaller average or maximum diameter) than the trailing region. Accordingly, the leading region may be described as a stem and the trailing region as a head of the nail. The leading region may be configured to enter the medullary canal first as the nail is being placed therein. The nail may taper, or decrease in diameter stepwise, at one or more positions along its length. Leading region 68 may include an elongated lockable section that is uniform in diameter and sized according to a transverse aperture of the anchor. The anchor may be locked to the nail over a continuous range of positions along the lockable section. The lockable section may have any suitable length, such as at least about 5%, 10%, or 20% of the length of the nail, among others.

To fix fibula 54, the nail may be attached to bone pieces 70, 72 (also described as bone segments) of fibula 54 (or another bone) located on opposite sides of fracture 56. Trailing region 66 of the nail may define one or more transverse openings 74 (such as through-holes or blind holes) to receive fasteners (such as threaded fasteners (e.g., screws)) that attach the trailing region to bone piece 70 and/or an end region 76 of the bone. Each opening 74 may or may not include an internal thread that is complementary to an external thread of the fasteners. For narrow bones such as the fibula, leading region 68 may be too thin to define any openings, such as holes, to receive fasteners, without compromising the strength of the nail. Anchor 62 disclosed herein provides attachment of leading region 68 of nail 60 to bone piece 72 and/or shaft region 58 of the bone, to stabilize fibula 54 and promote osteosynthesis at the fracture.

Nail 60 may be linear or may have a preformed radial curvature, for example, as indicated at 78. The nail thus may define a long axis 80 that is linear or nonlinear. The nail also may be sufficiently flexible, particularly in leading region 68, to be deformed as the nail is being placed into the medullary canal of the bone, such that the nail follows the longitudinal shape of the medullary canal.

The anchor may be elongated but substantially shorter than the nail. For example, the nail may be at least five or ten times the length of the anchor and/or a bushing thereof.

Anchor 62 may be introduced into fibula 54 from a side thereof in shaft region 58 of the bone. The anchor may be placed into the bone along an axis that is transverse, such as substantially orthogonal, to the long axis of the bone. In the depicted embodiment, anchor 62 is introduced from an anatomically lateral side of fibula 54, and advanced along a medial-lateral axis of the bone, but in other embodiments anchor 62 may be introduced from any suitable side of the fibula or other bone.

Figure 4:
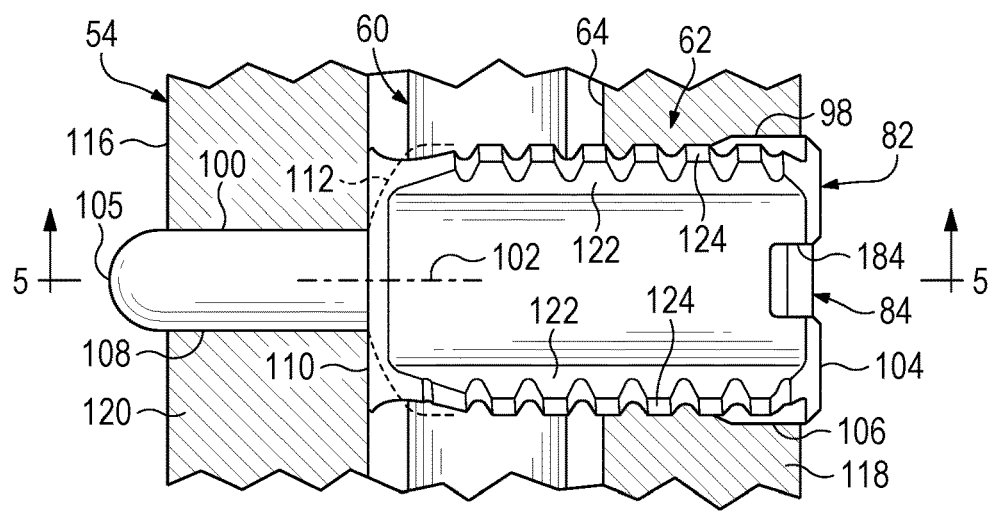
FIG. 4 is a fragmentary view of the fibula, nail, and anchor of FIG. 1, taken generally around the region indicated in FIG. 1 with the fibula sectioned longitudinally.
Figure 5:
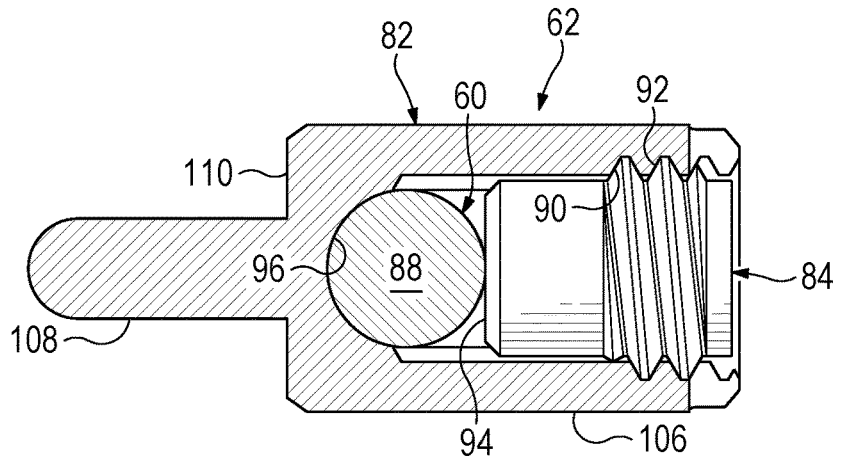
FIG. 5 is a partially sectional view of the nail and anchor of FIG. 1, taken along line 5-5 of FIG. 4.

FIGS. 3-5 show anchor 62 and its relationship to nail 60 and fibula 54 in more detail. Anchor 62 may include an assembly of a bushing 82 and a locking member 84 that are separate from, and attach to, one another. The bushing interchangeably may be called a housing. Bushing 82 may define a void 86 in which at least part of a lockable section 88 of nail 60 and at least part or all of locking member 84 may be received. Lockable section 88 may be clamped cooperatively by bushing 82 and locking member 84, to lock the nail to the bushing/anchor (see FIG. 5). For example, bushing 82 may define an internal thread 90, and locking member 84 may be a setscrew having a complementary external thread 92, or vice versa, to provide threaded engagement between the bushing and the locking member. (An extension of either thread also may be created by material deformation as the fixation system is installed; see Example 1.)

Locking member 84 may be rotated to adjust its axial position in the bushing, to advance a leading end 94 of the locking member, such that nail section 88 is tightly gripped on opposite sides thereof with leading end 94 and an internal wall region 96 of bushing 82, to lock the nail to the anchor. The internal wall region may be complementary to the nail (e.g., cylindrical in shape). The locking member may be configured to be located completely inside bushing 82 when the nail is locked to the bushing, with the trailing end of the locking member flush or recessed with respect to the bushing.

Leading end 94 of locking member 84 and/or internal wall region 96 of bushing 82 may be structured to further discourage slippage of the locked nail. One or both may have a protruding feature, which, in some embodiments, may be configured to dent the surface of nail 60 as the nail is being tightly clamped. For example, leading end 94 may form a distally-protruding rim or spike, which may be centered on the long axis of the locking member (see Section II and Example 1 of Section VIII), and/or internal wall region 96 may define one or more proximally-protruding ridges, bumps, spikes, etc., to contact the nail. To facilitate deformation of the nail by the protruding feature(s), the nail may be formed of a softer material than bushing 82 and/or locking member 84. In exemplary embodiments, the nail may be formed of titanium or a titanium alloy, and the bushing and/or locking member may be formed of a cobalt-chromium alloy (interchangeably called a cobalt-chrome alloy), among others.

Bushing 82 may have a trailing portion 98 and a leading portion 100 arranged coaxially to one another, with each centered on a long axis 102 of the bushing (see FIG. 4). Trailing portion 98 may extend to a trailing end 104 of the bushing, and leading portion 100 may extend to a leading end 105 of the bushing. The bushing may be unitary (only one piece) and/or may be configured to be installed as a unit. Trailing and leading portions 98, 100 may be formed integrally with one another. In other embodiments, the trailing and leading portions may be formed separately from one another, and then rigidly attached to one another. The trailing and leading portions may be contiguous with one another.

Trailing portion 98 may be substantially wider than leading portion 100, such that the portions form a body 106 and a post 108. For example, the trailing portion may have a diameter (e.g., an average diameter) that is greater than a diameter (e.g., an average diameter) of the leading portion. In some embodiments, the average diameter of the trailing portion may be at least about 1.5, 2, 2.5, or 3 times the average diameter of the leading portion. Each portion may be substantially cylindrical, as shown in the depicted embodiment. The post may stabilize the bushing to prevent it from wobbling within the bone.

Trailing portion 98 may form a shoulder 110 at a distal end thereof (see FIGS. 4 and 5). The shoulder may be formed by an abrupt end to body 106, as in the depicted embodiment, or by a more gradual linear or nonlinear decrease in the diameter of body 106, as indicated with dashed lines at 112 in FIG. 4. Accordingly, the shoulder may be planar and may lie in a plane oriented orthogonal to long axis 102, may be conical, or may be rounded in profile (e.g., being spherical), among others (also see Example 1 of Section VIII). The shoulder may form an angle (e.g., a maximum or average angle) of at least about 50, 60, 70, or 80 degrees with long axis 102 (and/or post 108) such that the shoulder is configured to act as stop during installation of the bushing.

Trailing and leading portions 98, 100 may have a different length from one another, with the length measured parallel to long axis 102. The different lengths may correspond to the different position and function of each portion within the bone as shown with fibula 54 sectioned in FIG. 4. A cortex 116 of fibula 54 forms a shell of dense, compact bone around medullary canal 64 in which nail 60 is located. Transversely-spaced regions of cortex 116 that are respectively closer and farther from the site of entry of bushing 82 are described as the near cortex 118 (proximal to the site) and the far cortex 120 (distal to the site). Trailing portion 98 may be located only partially in near cortex 118 and may span medullary canal 64 crosswise. Shoulder 110 may be configured to contact far cortex 120 to stop advancement of the bushing into bone during installation thereof. The trailing end of the trailing portion may be recessed, flush, or protruding with respect to the exterior of the bone. Leading portion 100 of the bushing may extend into and/or through far cortex 120, and may be located at least predominantly in far cortex 120, or at least predominantly in the far cortex and/or outside the bone, as in the depicted embodiment where a rounded tip of leading portion 100 protrudes from the far cortex. In other embodiments, the tip may be pointed or blunt, among others.

Bushing 82 may be configured to be attached to near cortex 118, far cortex 120, or both cortices. Trailing portion 98 and/or leading portion 100 may have at least one radial protrusion configured to attach the portion to bone by engagement, such as threaded engagement, with the corresponding region of the cortex. Each radial protrusion may, for example, include or form at least one thread, tooth, fin, barb, annular ridge, axial ridge, and/or the like. In some embodiments, one or both portions 98, 100 may have one or more radial protrusions forming an external thread structure, which is any fastening structure that corresponds to at least one continuous or segmented external thread. In the depicted embodiment, an external thread structure 121 having a segmented external thread is created by radial protrusions 122 formed only on trailing portion 98, with each radial protrusion defining a plurality of teeth 124, as described in more detail in Section II. In other embodiments, an external thread structure 121 having a more continuous configuration may be created by one or more helical protrusions on body 106 (see Example 1 of Section VIII), and/or a continuous/segmented external thread structure may be formed on post 108.

The fibula is only exemplary. Other suitable bones that may be fixed with the fixation system disclosed herein may include long bones, particularly long bones that have narrow shaft regions, such as the ulna, although the fixation assembly may be used with any suitable bone (e.g., the radius, humerus, femur, tibia, clavicle, etc.). In the depicted embodiment, nail 60 enters fibula 54 from an anatomically-distal end of the bone and then leading region 68 is attached to anatomically-proximal bone piece 72. However, in other embodiments, the nail may be introduced into a bone from an anatomically-proximal end thereof, and leading region 68 may be attached to an anatomically-distal piece of the bone.

The terms "proximal" and "distal" have different meanings herein for implants and bones. The terms "proximal" and "distal," as used to describe implants or instruments, mean respectively closer to and farther from the site of entry into bone and/or the surgeon during installation or use, and often correspond respectively to "trailing" and "leading." The terms "proximal" and "distal," as used to describe regions along a long bone, mean respectively closer to and farther from a site of attachment to the torso.

II. ANCHORS

This section describes further aspects of exemplary anchors 62 for the fixation systems of the present disclosure, and exemplary coaxial cortical bores in which the anchors can be installed; see FIGS. 6-16.

FIGS. 6-10 show various views of bushing 82 described above in Section I. As already discussed, the bushing may have a proximal, cylindrical body 106 and a distal post 108, which may or may not be cylindrical and/or elongated axially. Also, the bushing may have a plurality of external radial protrusions 122 formed on body 106 and arranged to provide an external thread structure, or to otherwise restrict removal of the bushing from bone.

Body 106 may be hollow, defining void 86 to allow the body to receive nail 60 radially and locking member 84 axially (also see FIGS. 3-5). More particularly, void 86 may include a transverse aperture 126 intersecting an axial opening 128. The transverse aperture is a through-aperture that extends through the body transversely (e.g., orthogonally to long axis 102, such as radially through the body as a radial aperture). The transverse aperture may be formed in part by internal wall region 96. Transverse aperture 126 may be sized to permit nail 60 to be progressively and longitudinally advanced, from its leading end, through the body until a lockable section of the leading region of the nail is located partially in the transverse aperture and extends through bushing 82 (e.g., radially). The transverse aperture may be a slot that is elongated parallel to long axis 102, to increase the size of the aperture, thereby increasing the chance of successful entry of the leading end of the nail into the bushing. Axial opening 128 may be sized to receive locking member 84 and may define internal thread 90.

Transverse aperture 126 may be tapered inward at one or both ends to form at least one inlet 130. The inlet further increases the target size of the aperture, thereby increasing the chance of successful entry of the leading end of the nail into the bushing's body. In the depicted embodiment, a pair of inlets 130 are defined by opposite lateral sides of body 106. Each inlet 130 may be created as a bevel 132, which may be a circumferential bevel as shown. At least part of at least one or each inlet/bevel may be formed by a radial protrusion (e.g., protrusion 122) on body 106. The bevel may define any suitable acute angle with a through-axis 134 of aperture 126, such as an angle greater than about 35, 40, or 45 degrees, among others. The increase in target size of the transverse aperture produced by the bevel is shown in FIGS. 9 and 10. The bevel may increase a maximum width 136 of the aperture (i.e., the width of the inlet; compare with internal width 138), and/or may increase a maximum length 140 of the aperture (i.e., the length of the inlet; compare with internal length 142). In some embodiments, internal width 138 may be at least about one-half the average diameter of body 106 (ignoring any protrusions forms thereon). In some embodiments, width 136 of inlet 130 may be at least about 40% or 50% greater than internal width 138, and/or may be at least about 75%, 80%, or 90% of the average diameter of body 106 (as defined above). In some embodiments, internal length 142 of aperture 126 and/or length 140 of at least one or each inlet 130 may be greater than one-half the length of body 106 measured parallel to long axis 102.

Radial protrusions 122 may be described as wings (see FIG. 8). The protrusions may be spaced from one another circumferentially on the body and may be spaced uniformly. For example, the depicted embodiment has four protrusions 122 spaced by 90 degrees from one another to define an X-shape in an end view of the bushing. In other embodiments, the bushing may have a different number of protrusions 122, such as 2, 3, 5, or 6, among others. Each of the protrusions may be linear and arranged axially on body 106, parallel to long axis 102, may be helical, or may have some other arrangement.

Body 106 may have teeth 124 formed laterally thereon, optionally provided by protrusions 122 (see FIG. 7). The teeth may be arranged in spaced columns 144, each extending parallel to long axis 102, and the columns may be uniformly spaced from one another, as described above for protrusions 122. The teeth considered collectively may be arranged on the same helical path 146. The pitch (p) of the helical path (i.e., the distance between successive full turns of the path) may be equal to the center-to-center spacing of adjacent teeth within each column. The columns of teeth may be axially offset from one another by a fraction of the pitch to place some or all of the teeth on the helical path. For example, with n uniformly spaced rows of teeth, the rows may be successively offset from one another by a distance of p/n. The axial columns of teeth permit the bushing to be driven into bone axially/translationally (without substantial rotation), or by rotating the bushing (such that the teeth function as an external thread), or both in succession. In other embodiments, the teeth may be replaced by a more complete external thread (e.g., see Example 1 of Section VIII).

Bushing 82 may have a driver-engagement structure formed internally, externally, and/or at its proximal (trailing) end, to facilitate driving the bushing into bone translationally and/or rotationally. In the depicted embodiment, body 106 defines a pair of recesses 148 at the trailing end thereof. The recesses may be diametrically spaced from one another. A corresponding driver is described below in Section V.

Figure 11:
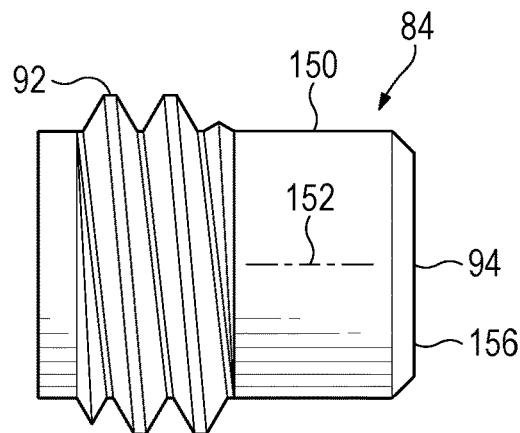
FIG. 11 is a side view of a locking member of the anchor of FIG. 1.
Figure 12:
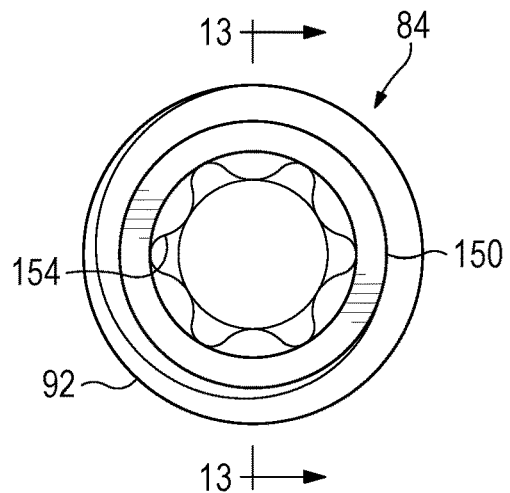
FIG. 12 is a proximal end view of the locking member of FIG. 1.
Figure 13:
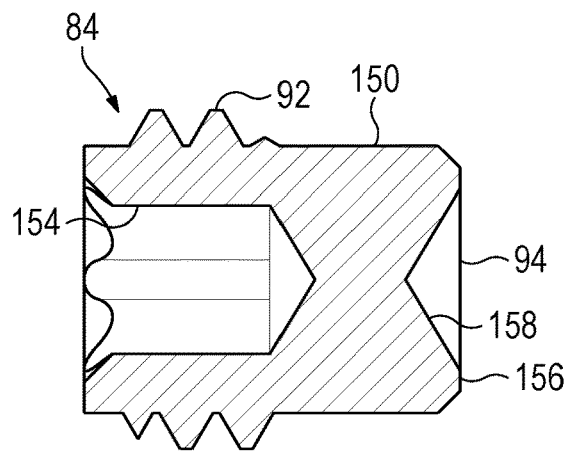
FIG. 13 is a sectional view of the locking member of FIG. 1, taken along line 13-13 of FIG. 12.

FIGS. 11-13 show various views of locking member 84, which was described above in Section I. The locking member may have a cylindrical shaft 150, with external thread 92 formed thereon. The length of the locking member, measured parallel to a long axis 152 thereof, may be less than the length of body 106 of bushing 82, such as approximately equal to the length of body 106 minus the diameter of the section of the nail that extends through the body, and further minus the distance between the distal end of body 106 and internal wall region 96 of the body that engages the nail. With this length, the proximal end of the locking member can be flush or recessed with respect to the proximal end of the bushing when the locking member is operatively engaged with the nail.

The proximal end of locking member 84 may define a driver-engagement structure 154. In the depicted embodiment, structure 154 is a hexalobe recess, but any suitable internal and/or external driver-engagement structure may be present.

The distal end of locking member 84 may define a protrusion 156 configured to engage, and optionally deform, the nail. In the depicted embodiment, protrusion 156 surrounds a central depression 158, such that the distal end of the locking member forms an annular, protruding rim to engage the nail.

Figure 14:
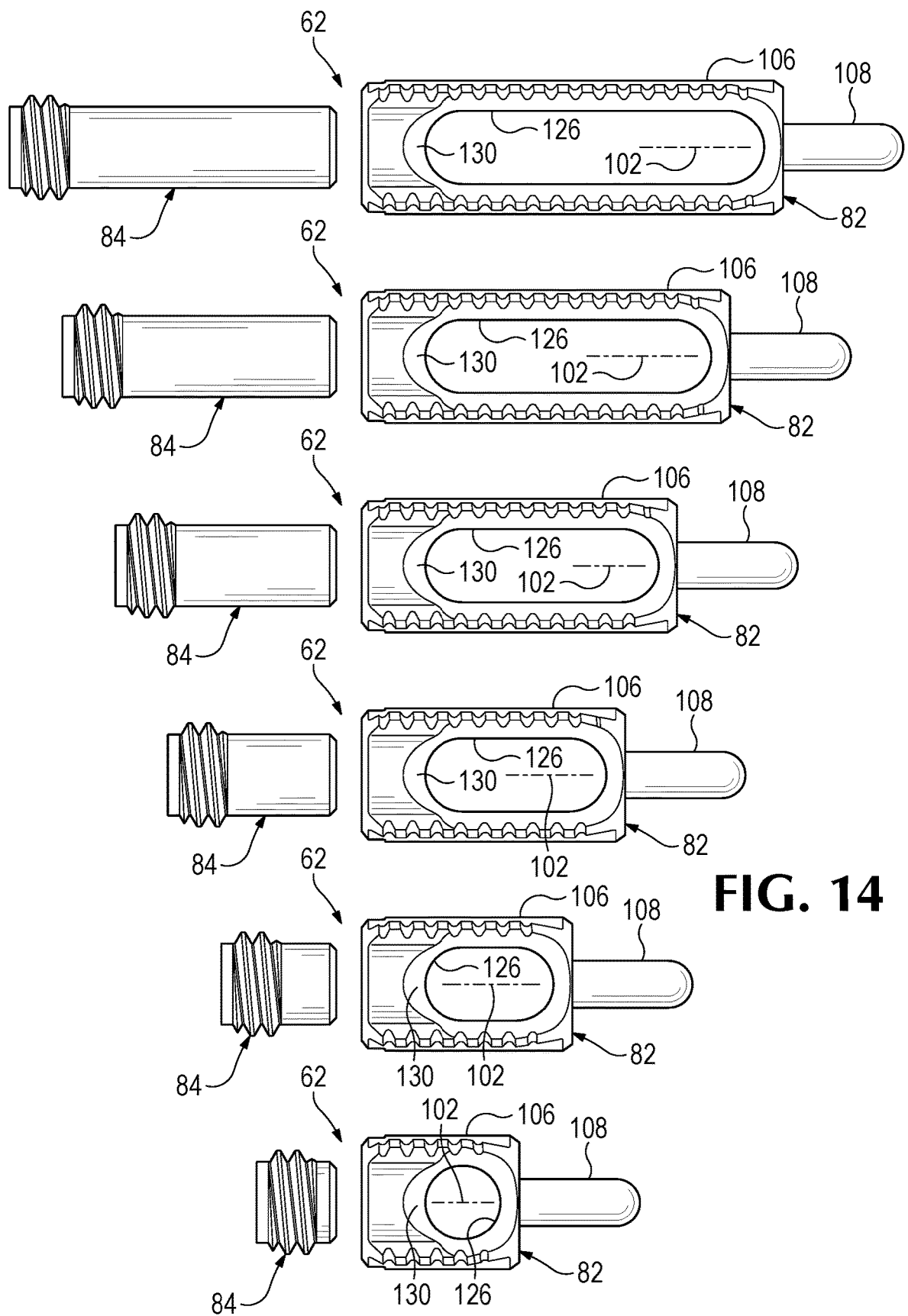
FIG. 14 is a set of bushings and corresponding locking members that may be included in the fixation system of FIG. 1, to facilitate attachment of the nail to regions of bone having different local widths.

FIG. 14 shows a set of bushings 82 and corresponding locking members 84 that may be included in fixation system 50. The set allows a surgeon to select a suitable size of anchor for a given bone, and particularly for the particular region of the bone where the anchor is to be installed. The bushings have the same diameter but are different in length from one another. The difference in length may be determined by body 106 of each bushing. In other words, bodies 106 may be different in length from one another, and posts 108 may have the same length (and/or diameter) as one another. In the depicted embodiment, posts 108 are identical to one another. Transverse aperture 126 may differ in length among bushings 82, measured parallel to long axis 102, in direct relation to the different lengths of the bushings 82 and/or bodies 106 thereof. By increasing the length of aperture 126 (and thus inlet 130), the target area for nail entry into the bushing is increased for bones of locally greater diameter. The elongated inlet 130 may substantially span the medullary canal of the bone, which simplifies alignment of the leading end of the nail with the inlet.

Locking members 84 may differ in length in correspondence with the differing lengths of bodies 106. Each locking member 84 may have a length that is approximately the length of corresponding body 106 minus the diameter of the leading region of the nail that extends through the body, and further minus the distance between the distal end of body 106 and internal wall region 96 of the body that engages the nail.

Figure 15:
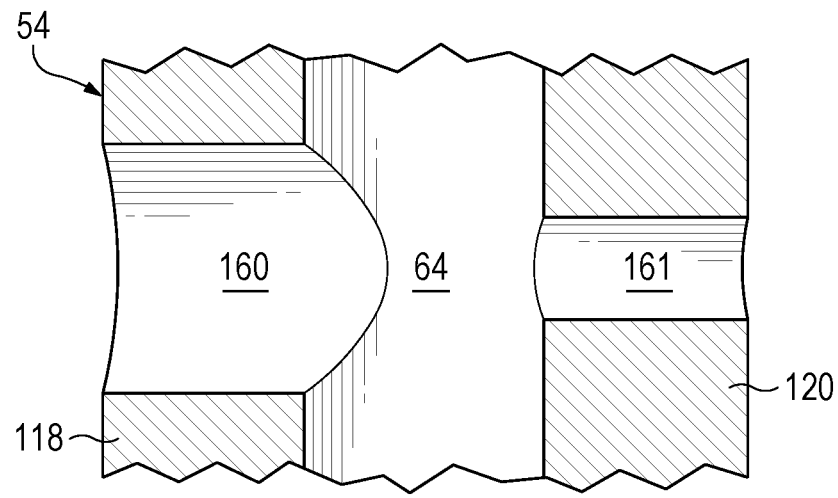
FIG. 15 is a fragmentary, sectional view of the fibula of FIG. 1, taken after the fibula has been bored bicortically to prepare the bone to receive the bushing.
Figure 16:
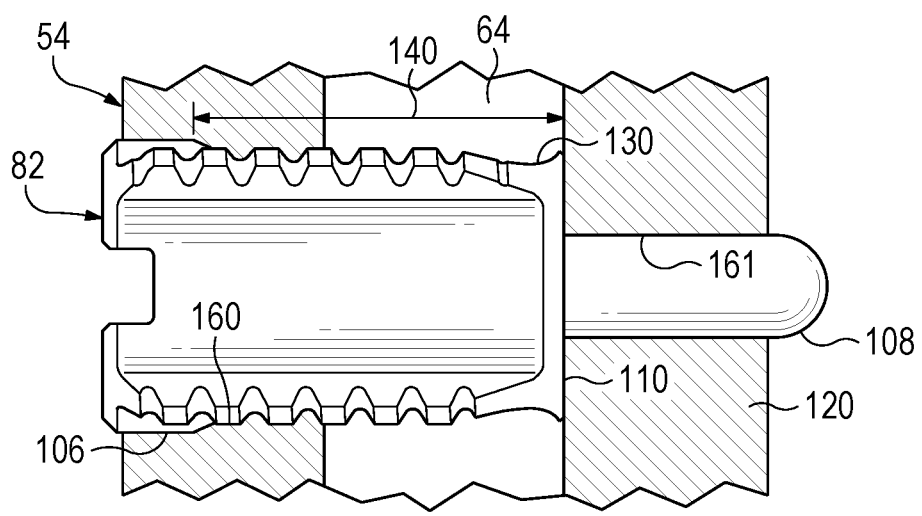
FIG. 16 is another fragmentary, sectional view of the fibula of FIG. 1, taken as in FIG. 15 except with the bushing implanted in the fibula.

FIGS. 15 and 16 respectively show fibula 54 prepared to receive bushing 82, and with the bushing installed. In FIG. 15, medullary canal 64 has been reamed, if needed, and fibula 54 has been bored bicortically to form a pair of coaxial, cylindrical holes, namely, a wider hole 160 through near cortex 118 and a narrower hole 161 in, and optionally through, far cortex 120. In FIG. 16, body 106 has been placed into wider hole 160 and medullary canal 64, and post 108 has been placed into narrower hole 161 and protrudes out of fibula 54. Shoulder 110 is abutted with far cortex 120, and optionally located in a matching/complementary recess formed in the inner side of the far cortex adjacent narrower hole 161. Length 140 of inlet 130 is greater than the local width of medullary canal 64.

III. NAIL WITH OFFSET TIP

This section describes an exemplary offset tip 162 for nail 60 of fixation system 50, and a procedure for utilizing tip 162 to help correct for misalignment and guide the nail into bushing 82; see FIGS. 17-20. The offset tip interchangeably may be called a kicked tip.

FIGS. 17-20 show a series of exemplary positional relationships of nail 60 and bushing 82 relative to one another. These positional relationships may be generated after the bushing has been installed transversely in bone, and as the nail is being mated with the bushing by a surgeon. In other words, bushing 82 is stationary and nail 60 is being advanced longitudinally along the medullary canal of the bone, indicated by motion arrows at 164, 166, and 168, to place a section of leading region 68 of the nail inside transverse aperture 126 of the bushing. Nail 60 and bushing 82 are viewed parallel to long axis 102 of the bushing, with bushing 82 sectioned as in FIG. 9, orthogonal to the long axis, so that tip 162 of the nail remains visible as it enters and passes through transverse aperture 126.

In some embodiments, the surgeon may monitor the positional relationship of nail 60 and bushing 82 fluoroscopically, with a viewing axis parallel to long axis 102, as the nail is being mated with the bushing generally in the manner shown. Inlet 130 of transverse aperture 126 may at least substantially span the medullary canal parallel to long axis 102, by selecting a suitably sized anchor/bushing from a set, as explained above in Section II. Accordingly, the surgeon often can successfully perform the mating procedure illustrated in FIGS. 17-20 without the need for viewing the bushing and nail fluoroscopically along a viewing axis orthogonal to long axis 102 (e.g., parallel to transverse axis 170).

Figure 17:
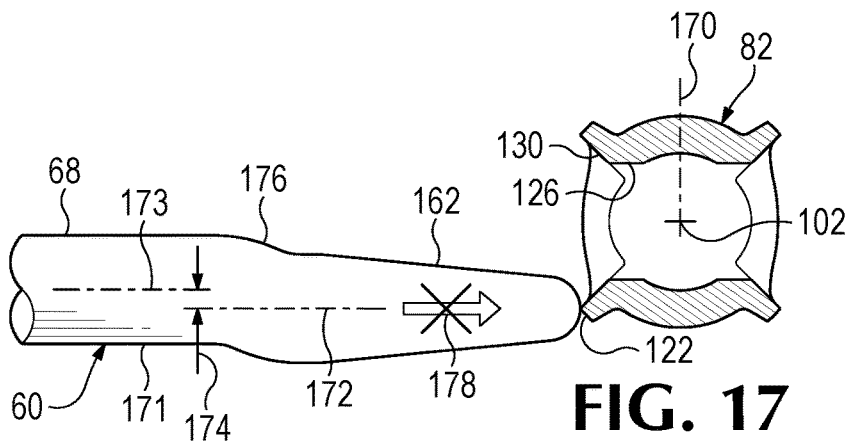
FIGS. 17-20 are a series of views of the nail and bushing of FIG. 1, with the nail shown as fragmentary and the bushing shown sectioned as in FIG. 9, taken as the tip of the nail is being passed through a transverse aperture of the bushing, and schematically illustrating how an offset of the tip and rotation of the nail can cooperate to correct for misalignment between the tip and the transverse aperture, thereby allowing the tip to successfully enter the bushing.

FIG. 17 shows only a distal portion of leading region 68 of nail 60. Leading region 68 has an elongated main portion 171 and tip 162 located distally thereof. The tip may be elongated to define a tip axis 172 that is not collinear with a long axis 173 defined by main portion 171. Axes 172, 173 may or may not be substantially parallel to one another. In the depicted embodiment, the axes are spaced from one another by a radial offset 174 created by a bent region 176 (e.g., a double bend) in the nail. The nail may bend radially in respective opposite directions as it extends longitudinally through the bent region. Each bend may be in a plane in which trailing region 66 of nail 60 curves. The tip may be tapered, as shown, or cylindrical, and may have a rounded or pointed distal end.

Misalignment of nail 60 and bushing 82 relative to one another can prevent the distal end of the nail from entering inlet 130 of transverse aperture 126 (see FIG. 17). For example, in the depicted configuration, the distal end of tip 162 is in contact with lateral protrusion 122 and cannot advance, indicated by a crossed-out motion arrow at 178.

Figure 18:
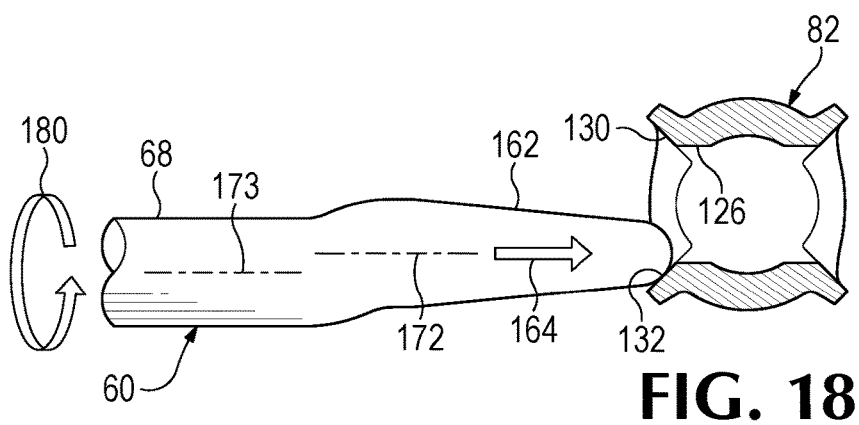

FIG. 18 shows a position of nail 60 after the nail has been rotated one-half turn about its long axis by the surgeon, indicated by a rotation arrow at 180. Tip axis 172 now intersects inlet 130 of aperture 126, and bevel 132 of the inlet provides a ramp that helps to center tip 162 transversely in aperture 126, as the nail is advanced at 164. In other embodiments, the nail may be rotated a different amount, such as 90 degrees, among others.

Figure 19:
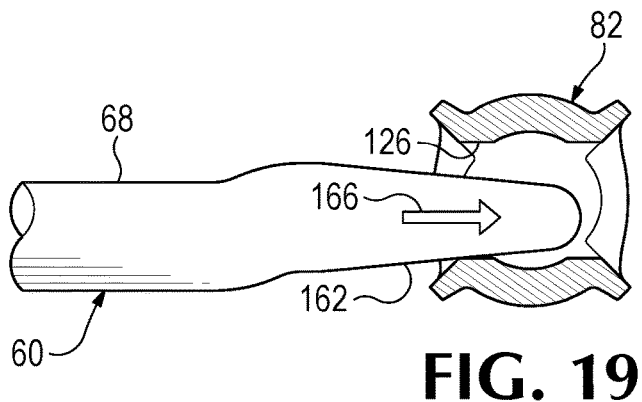

FIG. 19 shows tip 162 being advanced, indicated by motion arrow 166, farther into transverse aperture 126. The tip is being centered further by contact between its tapered wall and an internal region of the transverse aperture.

Figure 20:
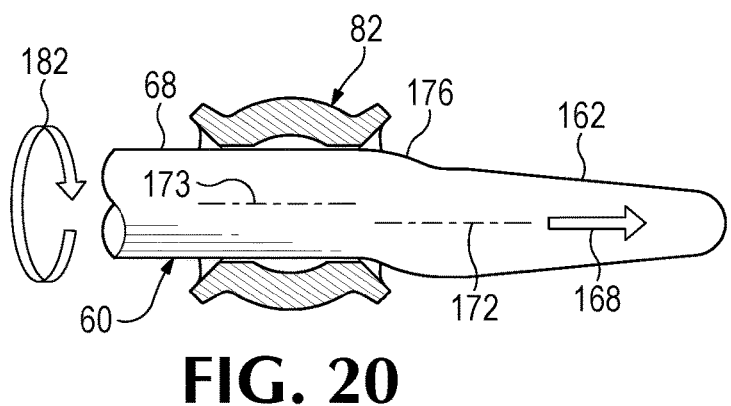

FIG. 20 shows further advancement of the tip, indicated by motion arrow 168, after the tip and bent region 176 have passed through bushing 82. The nail may be rotated about axis 80 one-half turn in reverse, indicated by a rotation arrow at 182, to restore the nail to its original rotational orientation, if needed. In the depicted embodiment, nail 60 has a preformed radial curvature 78 (see FIG. 1) which may preferably follow that of the medullary canal. Radial curvature 78 and the offset of tip 162 may be in the same plane.

IV. INSTRUMENT

This section describes exemplary embodiments of a non-implantable instrument of fixation system 50 to facilitate installation of bushing 82 and/or locking member 84 (see Sections I and II), and procedures for using the instrument; see FIGS. 21-38.

Figure 21:
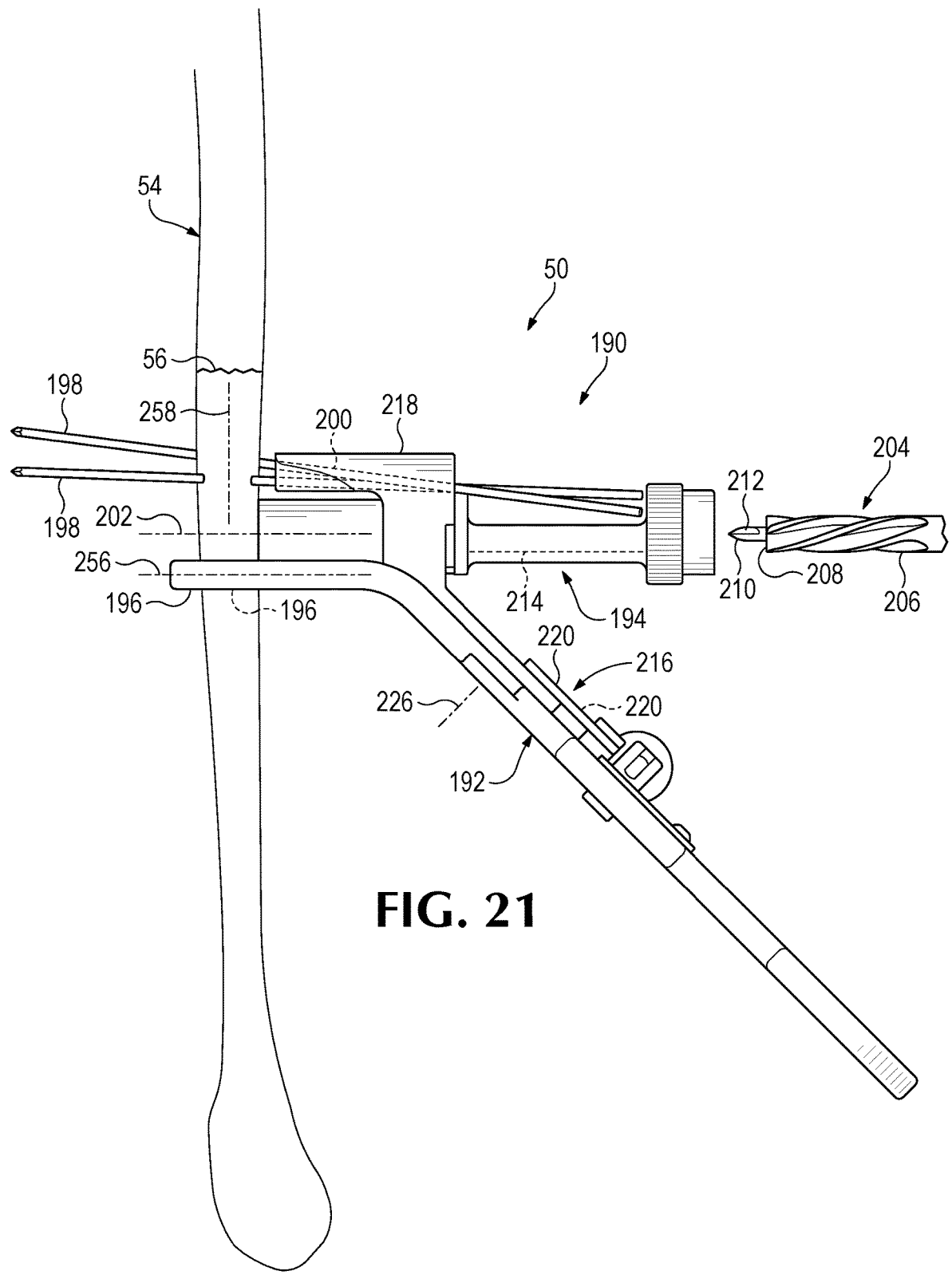
FIG. 21 is a fragmentary, anterior view of the fibula of FIG. 1, taken during preparation of the fibula to receive the bushing of FIG. 1, and showing an exemplary instrument mounted to the fibula, in part with wire members, and positioned to guide a step drill, shown as fragmentary, into the fibula, in accordance with aspects of the present disclosure.

FIG. 21 shows an embodiment 190 of the instrument having a clamp portion 192 coupled to a guide portion 194. A pair of opposing jaws 196 of the clamp portion may be engaged with fibula 54, such that the fibula is clamped between the jaws, and/or one or more wire members 198 may be placed through one or more wire-receiving channels 200 defined by the instrument to couple the instrument to the bone. Coupling the instrument to the bone with jaws 196 and at least one wire member 198 can provide better stabilization of the instrument on the bone. Guide portion 194 defines a guide axis 202. At least one drill 204 may bore fibula 54 (or another bone) on the guide axis to prepare the fibula to receive bushing 82, and/or the bushing may be passed through guide portion 194 along guide axis 202 and into the fibula. (Each drill interchangeably may be termed a drill bit.)

The at least one drill may bore fibula 54 (or another bone) bicortically to form a wider hole in the near cortex and a narrower hole in the far cortex, as described above in Section II (e.g., see FIGS. 15 and 16). In some embodiments, respective, corresponding drills may be utilized to form the holes of different size. Alternatively, a step drill 204 may be used to form both holes in a single pass. The step drill may have a shaft 206 having a proximal boring portion 208 to form the wider hole, and a nose 210 that protrudes from the shaft and provides a distal boring portion 212 to form the narrower hole. In some embodiments, the proximal and distal boring portions of the drill may be configured to bore preferentially in opposite rotational directions of the drill from one another, as described in U.S. patent application Ser. No. 15/728,247, filed Oct. 9, 2017, which is incorporated herein by reference. (The terms drilling, boring, and forming a hole are used interchangeably herein.) Shaft 206 may be sized to extend through a guide channel 214 defined by guide portion 194 and centered on guide axis 202.

Instrument 190 may include a coupling assembly 216 that couples clamp portion 192 and guide portion 194 to one another. The coupling assembly keeps the guide portion centered, as explained in more detail below, and may include a holder 218 (interchangeably termed a housing) for the guide portion and a pair of linkage members 220.

FIGS. 22 and 23 show instrument 190 without guide portion 194, and with jaws 196 in a closed configuration and an open configuration, respectively. The instrument may have a pair of levers 222a, 222b connected pivotably to one another at a fulcrum 224 defining a pivot axis 226 (also see FIG. 21). Jaws 196 are formed by portions of the levers located distally to fulcrum 224, and a pair of handle members 228 may be formed proximally to the fulcrum by the levers.

Coupling assembly 216 maintains holder 218 at a fixed position with respect to a central plane 230 as the distance between jaws 196 is changed (i.e., as the jaws are opened (moved farther from one another) or closed (moved closer to one another)) (compare FIGS. 22 and 23). The central plane may contain pivot axis 226 and may remain equidistant from the jaws (and optionally handle members 228) as their separation is changed. Guide portion 194, and particularly guide axis 202 thereof, thus can remain lying in central plane 230 as the jaws are opened and closed. This positional relationship ensures that the guide axis extends across the bone close to the long axis of the bone when the jaws are engaged with opposite sides of the bone. In some embodiments, the guide axis may be adjustably offset from the central plane, if needed, as described below.

Figure 24:
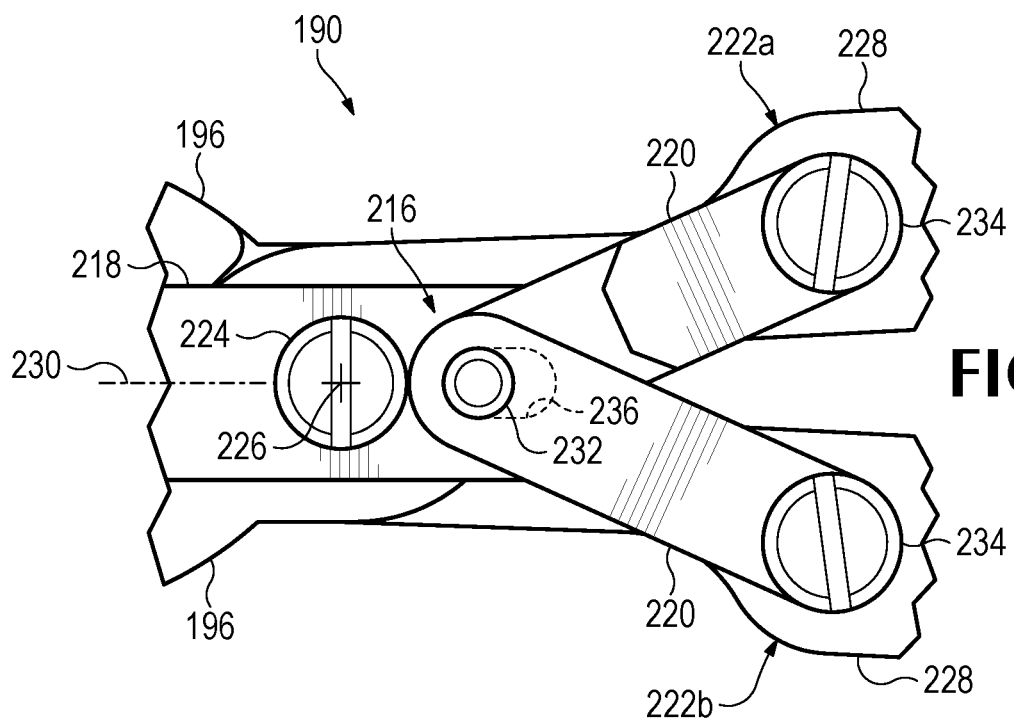
FIG. 24 is a fragmentary top view of the instrument of FIG. 21, taken as in FIG. 22 around a fulcrum and coupling assembly of the instrument.
Figure 25:
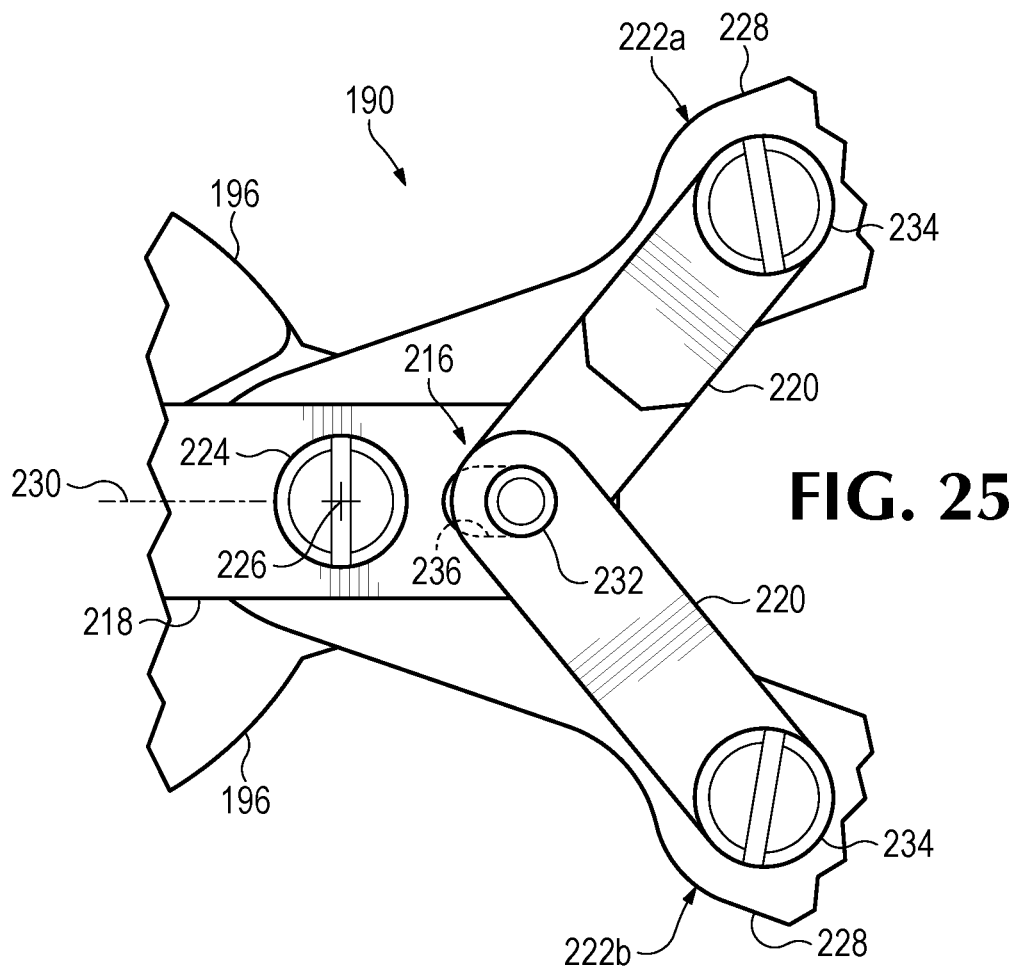
FIG. 25 is another fragmentary top view of the instrument of FIG. 21, taken as in FIG. 23 around the fulcrum and coupling assembly of the instrument.

FIGS. 24 and 25 show respective fragmentary views of instrument 190 in the configurations of FIGS. 22 and 23 and illustrate how coupling assembly 216 can operate. Holder 218 may be pivotably connected to levers 222a, 222b on pivot axis 226. Linkage members 220 may be pivotably connected to one another and to holder 218 at one end of each linkage member, to form a pivotable connection 232, and may be pivotably connected to a respective lever 222a or 222b at the other end of each linkage member, indicated at 234. Holder 218 may define a slot 236 that permits pivotable connection 232 to slide along the slot as the separation of the jaws is changed (compare FIGS. 24 and 25). As a result, angular motion of the levers with respect to holder 218 is coupled, and holder 218 cannot pivot out of alignment with central plane 230. In some embodiments, the positions of fulcrum 224 and slot 236 may be switched. In other embodiments, the same type of centering action can be created by replacing slot 236 with a circular aperture, and providing a slot in each lever 222a, 222b, such that each pivotable connection 234 can slide along a corresponding lever as the jaws are opened and closed.

FIGS. 22 and 23 show additional exemplary aspects of instrument 190. The instrument may have a locking mechanism 238 to prevent the jaws from being opened (moved farther apart). The locking mechanism may or may not restrict the jaws from being closed (moved closer together), since that role may be played by the bone engaged on opposite sides by the jaws. In the depicted embodiment, instrument 190 has an externally threaded member 240 pivotably connected at one end to lever 222b, extending through a collar 242 of the other lever, and in threaded engagement with an internally threaded wheel 244. The locking mechanism is in an unlocked configuration in FIG. 22, because wheel 244 is spaced from collar 242, and in a locked configuration in FIG. 23, where the wheel is in contact with the collar. In other embodiments, the locking mechanism may include meshed teeth or the like.

Instrument 190 also may have a gauge 246 to measure the separation of the jaws from one another, and thus the local width of a bone engaged by the jaws. The gauge may be located proximally or distally with respect fulcrum 224. In the depicted embodiment, the gauge is associated with handle members 228. In particular, the gauge has a scale 248 attached to one of handle members 228, and a pointer 250 attached to the other handle member. Scale 248 may be arcuate or linear, among others.

FIG. 22A shows further aspects of scale 248. The scale may include indicia 252 to indicate the current separation of the jaws from one another. The indicia may include graduation marks (which may be uniformly spaced), alphanumeric characters (e.g., numbers), and color coding, among others. For example, the numbers may report the distance (e.g., in millimeters) between the jaws. The color coding may indicate whether the jaw separation (and thus local bone width) is sufficient for safely introducing the anchor. In the depicted embodiment, sections 253a, 253b, and 253c of increasing distance from lever 222a along the scale are colored red, yellow, and green, respectively, to indicate high, medium, and low risk for drilling and/or insertion of the anchor.

Figure 26:
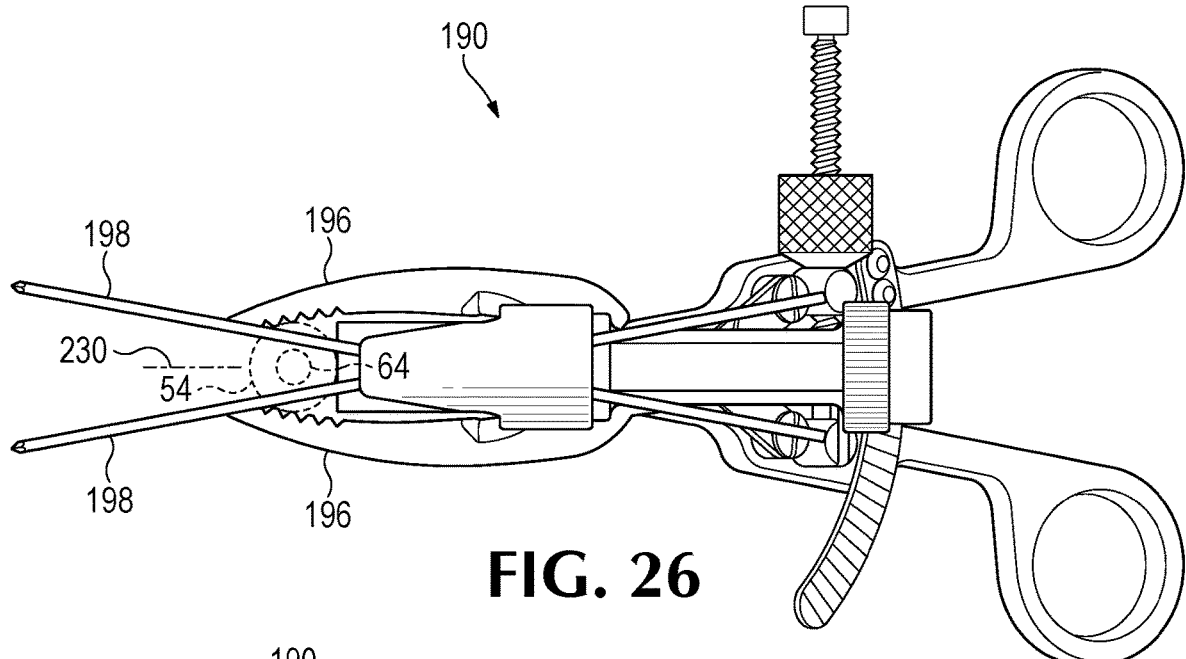
FIG. 26 is a top view of the instrument of FIG. 21, taken with the cortex and medullary canal of the fibula shown schematically in phantom outline.
Figure 27:
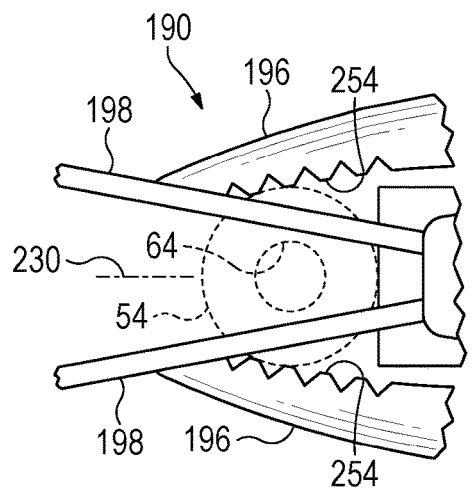
FIG. 27 is a fragmentary view of the instrument of FIG. 21, taken as in FIG. 26 and showing exemplary trajectories on which the instrument may direct a leading end of wire members into and/or through the bone to further couple the instrument to bone, thereby stabilizing the instrument on the bone.
Figure 28:
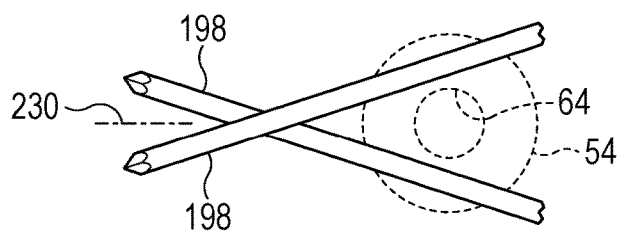
FIG. 28 is a schematic view corresponding to FIG. 27 but showing different exemplary trajectories on which the instrument may direct the leading end of wire members into and/or through the bone to stabilize the instrument.

FIGS. 26 and 27 show an exemplary positional relationship between wire members 198, instrument 190, fibula 54, and medullary canal 64. Jaws 196 may define teeth 254 to engage opposite sides of the bone and improve purchase. The jaws may be angled inward distally, toward central plane 230, when the jaws are fully closed and for a range of open positions of the jaws, to resist removal of the locked instrument from the bone. The jaws engage a bone in a clamping plane 256, which may be oriented at least generally orthogonal to a long axis 258 of the bone when the instrument is properly clamped to the bone (see FIG. 21). The clamping plane may be at least generally parallel to, and optionally spaced from, guide axis 202, and orthogonal to central plane 230. (At least generally orthogonal (or parallel) means within ten degrees of exactly orthogonal (or parallel).) Each of the jaws may be oriented at an oblique angle with respect to a plane that is orthogonal to pivot axis 226. Accordingly, the jaws may travel along a surface of a cone centered on pivot axis 226 as the jaws are opened or closed.

Channels 200 of the instrument may define trajectories for wire members 198 that extend into and/or through the bone transversely. The channels may be defined by holder 218, one or both levers 222a, 222b, or by both the holder and one or both levers. The trajectories may be configured to extend through at least one region of the bone that is spaced along the bone from clamping plane 256 and guide axis 202. For example, in the depicted embodiment, guide axis 202 is located intermediate clamping plane 256 and the region of the fibula that receives wire members 198. In other embodiments, clamping plane 256 may be located along the fibula between the region of the fibula that receives wire members 198 and guide axis 202. In yet other embodiments, a pair of the trajectories may pass through the bone on opposite sides of the clamping plane from one another.

The wire-receiving channels may be configured to define trajectories that pass through cortical bone while avoiding at the least the radially central portion of the medullary canal, to permit advancement of a leading end of the nail along the medullary canal past the wire members. In other words, the wire members avoid the space to be occupied by the nail. Each trajectory may pass through central plane 230 before or after the trajectory has passed through bone. For example, in FIGS. 26 and 27, both wire members pass through central plane 230 before reaching the bone, while in FIG. 28 the wire members pass through the bone before reaching central plane 230.

Each wire member may be placed into/through bone after the nail has been provisionally positioned in the medullary canal, substantially in the space the nail will occupy once locked to the bushing. Having the nail in this position ensures that the wire member, when placed into bone, will not block re-advancement of the nail into the space, after the nail has been retracted to permit drilling and bushing installation along the guide axis.

Figure 29:
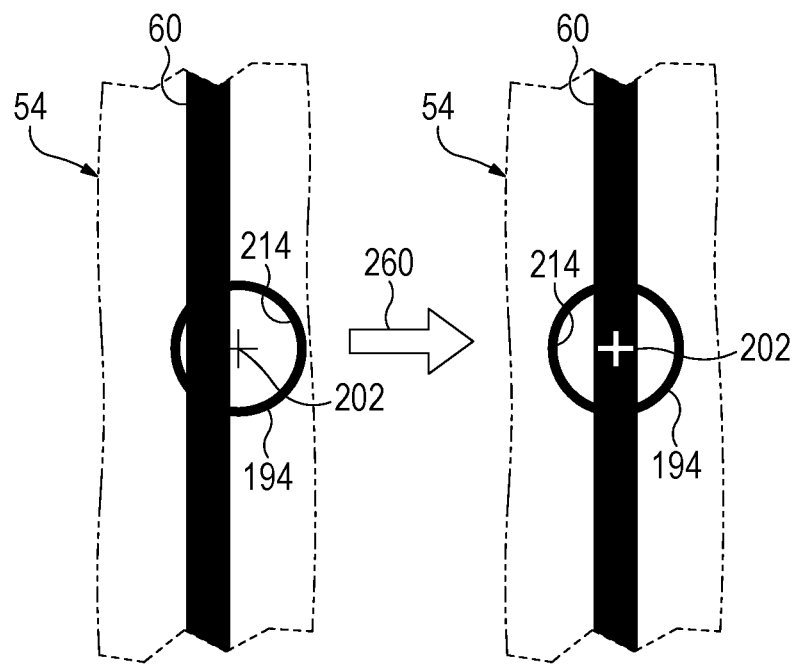
FIG. 29 is a schematic illustration of a pair of fluoroscopic images showing fragmentary axial portions of the fibula and nail of FIG. 1, and a guide tube of the instrument of FIG. 21, viewed along the axis defined by the guide tube, before (left) and after (right) the position of the tube has been adjusted to improve the alignment of the tube with the nail.

FIG. 29 shows a pair of schematic fluoroscopic images illustrating adjustment, indicated by an arrow at 260, of the position of guide portion 194 of instrument 190 while the instrument is clamped to fibula 54 and further stabilized with wire members (not shown). The guide portion and nail 60 (or a reamer) are viewed substantially in line with guide axis 202, and may be radiopaque (at least in part) to make them readily visible fluoroscopically. The leading end of the nail has been advanced along the medullary canal of fibula 54 past guide axis 202 and overlying guide portion 194.

Guide channel 214 of guide portion 194 is not centered on the long axis of nail 60 (or reamer) in the image on the left. Accordingly, if the alignment of guide portion 194 and nail 60 is not improved before boring the fibula on guide axis 202, the surgeon may have difficulty feeding the nail through bushing 82 installed in the bored fibula. As described in more detail below, the position of guide portion 194 may be adjusted while the instrument remains clamped to the bone, to improve the alignment of the guide portion with the nail as shown in the image on the right.

FIGS. 30A-30C, 31, and 32 illustrate an exemplary adjustment mechanism of instrument 190 for changing the position of guide portion 194 with respect to holder 218 (and central plane 230). The adjustment moves guide portion 194, while holder 218 and the jaws of the clamp portion remain stationary. The adjustment may permit guide axis 202 to be offset from central plane 230 in opposite directions (also see FIGS. 22 and 23), optionally by the same distance, to improve the alignment of the guide axis with the long axis of the nail. The guide portion may be locked in place through use of complementary mating structures provided by the guide portion and holder 218, as described below. The complementary mating structures may be mated with one another in a plurality of alternative configurations, to provide a plurality of predetermined, discrete adjustments to the offset of the guide axis from central plane 230. In other embodiments, the adjustment mechanism may permit adjustment of the spacing of the guide axis from the central plane over a continuous range of positions.

Guide portion 194 may include a tube 262 defining guide channel 214. A cap 264 (also called a button) may be firmly attached to a proximal end of tube 262 (see FIGS. 30A and 32), such as with a plurality of setscrews. Guide channel 214 may be open only at both ends or also may be open laterally along at least a portion of its length, to form a furrow 266. A locking sleeve 268 may encircle parts of tube 262. The locking sleeve may form a knob 270 proximally, which may be knurled. An axial tang 272 may be defined by the locking sleeve distally (see FIG. 32). A distal portion 274 of the tang may be received in an axial groove 276 defined on the radially outer side of tube 262, to prevent rotation of the tube and the locking member relative to one another about the coincident long axes 278 thereof (see FIGS. 31 and 32). A proximal portion 280 of the tang may be received in, and may be complementary to, each of a plurality of pockets 282a, 282b, 282c defined by an opening 284 through holder 218. Tube 262 is held in opening 284 of the holder by a retainer 286, which prevents any axial motion of the tube, while permitting the tube to rotate about its long axis when not locked by locking sleeve 268. The locking sleeve may be urged distally parallel to guide axis 202 by a spring 288 to keep the guide portion locked.

Figure 30A:
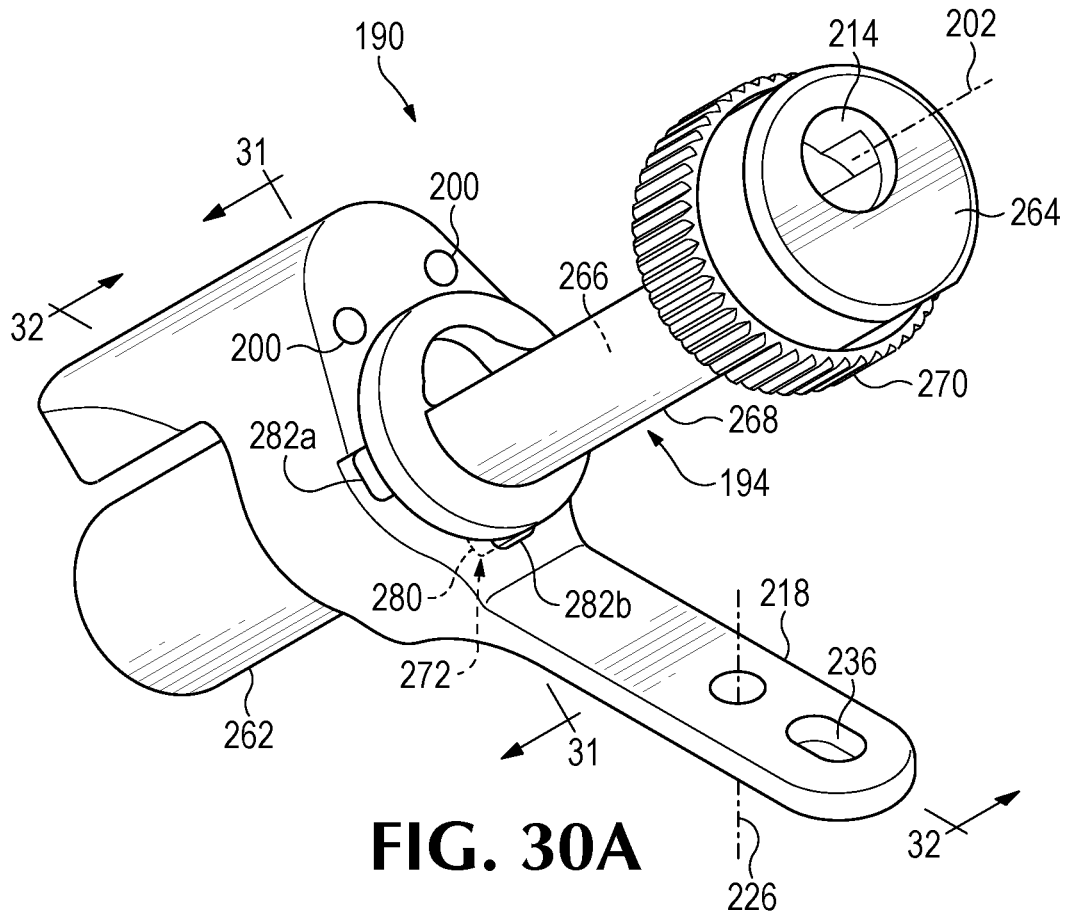
FIG. 30A is an isometric view of a guide portion and a holder of the instrument of FIG. 21, taken in isolation from the rest of the instrument, with the guide portion in a locked configuration that prevents rotation with respect to the holder.
Figure 43:
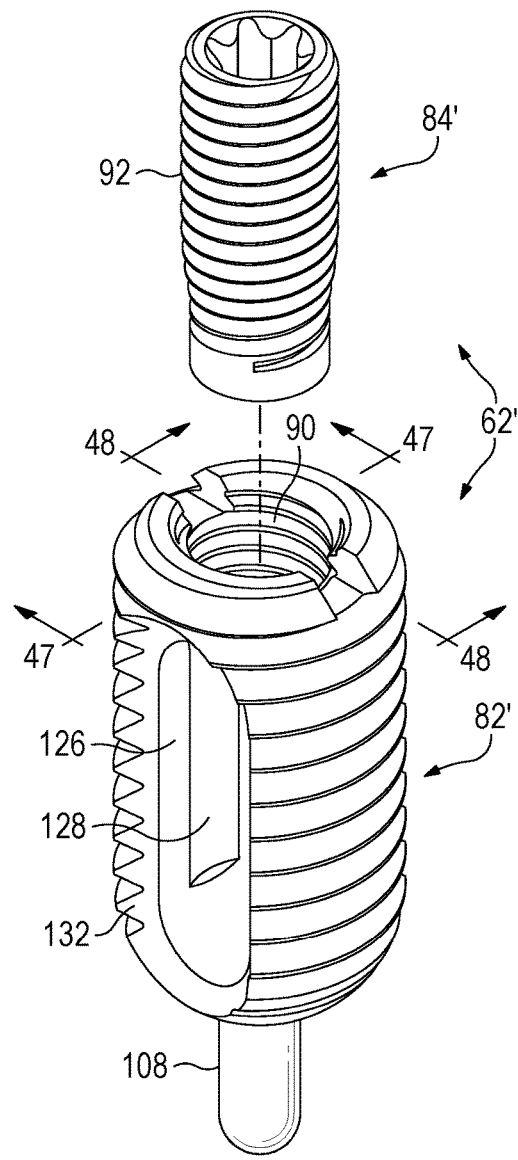
FIG. 43 is an exploded view of another exemplary encircling anchor for the nail-based fixation system of FIG. 1, in accordance with aspects of the present disclosure.

FIGS. 30A-30C illustrate an exemplary adjustment of the rotational position of guide portion 194. In FIG. 30A, proximal portion 280 of tang 272 is located in central pocket 282b, locking tube 262 in place. In FIG. 30B, the guide portion has been unlocked by urging locking sleeve 268 proximally relative to tube 262, parallel to long axes 278, indicated by motion arrows at 290. Upward pressure may be applied to knob 270 to compress spring 288 and remove proximal portion 280 of tang 272 from pocket 282b. In FIG. 30C, guide portion 194 has been rotated, indicated by a rotation arrow at 292, to align tang 272 with pocket 282a while spring 288 remains compressed. Tang 272 then may be allowed to enter pocket 282a by releasing the upward pressure on knob 270, thereby re-locking the guide portion at a new rotational position.

FIG. 31 shows a sectional view of the guide portion in the locked position of FIG. 30A. The position of guide channel 214 in alternative locked positions of the guide tube are show in phantom.

FIGS. 33A-33C, 34, and 35 show only guide portion 194 and holder 218 of another exemplary embodiment 190' of an installation instrument for fixation system 50. Instrument 190' may have any suitable combination of the elements and features described above for instrument 190, such as the clamp portion and coupling assembly thereof. Accordingly, functionally similar components of instruments 190 and 190' have been assigned the same reference numbers.

Guide portion 194 of instrument 190' has a tube 262 defining guide axis 202. The position of the guide axis can be changed by moving the tube with respect to holder 218, to a different, alternative mating configuration of a tang 272 with one of a plurality of pockets 282a-282c defined by holder 218. However, in contrast to instrument 190, tube 262 of instrument 190' is movable axially and rotationally with respect to holder 218, as described further below.

Tube 262 has a tubular body 300 defining channel 214 and projections extending laterally therefrom, namely, tang 272 and a tab 302 (see FIGS. 33A-C and 35). One or both of tang 272 and tab 302 may be formed integrally with body 300. A threaded member 304 may be attached to tab 302 at an internally threaded through-hole 306 defined by the tab. More particularly, the threaded member may have a graspable head 308 forming a knob that is coaxial with and rigidly attached to a shaft 310 (see FIG. 35). The head may be knurled. The shaft may be externally threaded near the head for threaded engagement with through-hole 306. Shaft 310 may define a pair of circumferential depressions 312, 314 configured to receive a lateral portion of locking pin 316, to hold tube 262 in a locked configuration or an unlocked configuration, respectively. The shaft may be received in an axial bore 318 defined by holder 218.

Locking pin 316 may extend into a transverse bore 320 defined by holder 218 (see FIG. 34). The pin may have a shaft 322 defining a waist 324, and a button 326 may be formed at the proximal end of the shaft. A spring 328 may bias the position of shaft 322, such that waist 324 is out of alignment with shaft 310 of threaded member 304 until a user applies pressure to button 326, to compress spring 328.

FIGS. 33A-33C illustrate adjustment of the position of tube 262, to change the spacing of guide axis 202 from central plane 230 of holder 218 (also see FIG. 34). In FIG. 33A, guide axis 202 is contained by central plane 230, and tube 262 is locked in its central position. More particularly, tang 272 is located in central pocket 282b of holder 218. Axial motion of tube 262 is prevented by locking pin 316, which is located partially in upper depression 312 of shaft 310 of threaded member 304 (also see FIG. 35).

In FIG. 33B, button 326 of locking pin 316 has been pressed, indicated by a motion arrow at 330. The locking pin moves inward, parallel to its axis, which moves waist 324 of the locking pin into alignment with shaft 310 of threaded member 304 (also see FIG. 34). Tube 262 is now unlocked and can be moved axially, indicated by a motion arrow at 332, to remove tang 272 from central pocket 282b. The tube can be axially locked in the retracted position shown in FIG. 33B, with locking pin 316 located partially in lower depression 314.

In FIG. 33C, unlocked tube 262 has been moved laterally and reoriented, by pivoting the tube, indicated by a rotation arrow at 334, about an axis 336 defined by shaft 310 of threaded member 304. Tang 272 has been aligned with lateral pocket 282c. The tube then may be moved axially to place the tang in the lateral pocket, until locking pin 316 pops out to its locking position. The threaded member may be rotated via head 308 to more firmly fix the tube in place.

FIG. 34 shows opening 284 of holder 218. The opening may be shaped to permit lateral motion of the tubular body of tube 262, indicated by motion arrows at 338, when tube 262 is pivoted about shaft 310 of threaded member 304.

FIGS. 36-38 show only a guide portion 194 and a holder 218 of another exemplary embodiment 190" of an installation instrument for fixation system 50. Instrument 190" may have any suitable combination of the elements and features described above for instrument 190, such as the clamp portion and coupling assembly thereof. Accordingly, functionally similar components of instruments 190 and 190" have been assigned the same reference numbers.

Holder 218 of instrument 190" is generally similar to that of instrument 190. For example, the holder has a housing portion 350 defining an opening 284 to receive tube 262. The holder also has an arm 352 projecting from and in fixed relation to the housing portion, and defining a slot 236. However, in contrast to instrument 190, slot 236 of arm 352 in instrument 190" is located closer to housing portion 350 than a bore 354 centered on pivot axis 226.

Tube 262 has a mating portion 356 defining a pair of ridges 358 formed on opposite sides of the mating portion. The ridges are parallel to a guide axis 202 defined by tube 262. Ridges 358 are configured to be received alternatively in each aligned pair of a plurality of pairs of grooves 360 defined by housing portion 350 in opening 284. Each aligned pair of grooves 360 defines a plane parallel to central plane 230 of instrument 190" and orthogonal to clamping plane 256. Accordingly, when ridges 358 are mated with any of the aligned pairs of grooves 360, by motion of tube 262 and holder 218 relative to one another parallel to guide axis 202, the guide axis is either contained in central plane 230 or parallel to and offset therefrom. In the depicted embodiment, tube 262 can be held by holder 218 in five different positions in a plane orthogonal to the guide axis, indicated generally by arrows at 362 in FIG. 38. In other embodiments, more or fewer grooves may be provided, to provide more or fewer positions for the guide axis. To change the position of tube 262, the tube may be removed from housing portion 350, and then re-mated at a desired position along a transverse axis 364. The tube may have an enlarged head 365, which may be knurled, to facilitate grasping tube 262.

Guide portion 194 of any of instruments 190, 190', and 190" may include at least one tubular insert 366 configured to be received removably in tube 262. The insert may define an axial bore 368 that extends axially through the insert. Insert 366, and particularly bore 368, may be sized to guide a narrower tool, such as a drill or a guide wire, or locking member 84, into bone. The outer diameter of insert 366 may correspond to the inner diameter of tube 262, such that the insert fits closely in the tube and remains parallel to the guide channel.

V. DRIVER

This section describes an exemplary driver 380 for fixation system 50 that attaches to bushing 82; see FIGS. 39-42.

Driver 380 may have a distal shaft portion 382 attached to a proximal, graspable handle portion 384. The shaft portion may be formed at least in part by a sleeve 386 that is fixed to the handle portion proximally. A pair of projections 388 may protrude from the distal end of the sleeve. The projections may be complementary to, and mate with, recesses 148 defined by the proximal end of bushing 82. A rod member 390 having a knob 392 at a trailing end thereof, may extend through a channel 394 defined by handle portion 384 and sleeve 386, and may be rotatable about its long axis with respect to the handle portion and sleeve.

A distal section of the rod member may have an external thread 396 that is complementary to internal thread 90 of bushing 82 (also see FIG. 5). The rod member may be movable axially to extend and retract the distal end of the rod member from the sleeve. Bushing 82 may be locked to driver 380 in a defined rotational position by mating projections 388 with recesses 148, while rod member 390 is retracted slightly, and then advancing and rotating the rod member to produce threaded engagement between external thread 396 and internal thread 90. Alternatively, the rod member may have a fixed axial position, and may be rotated to provide threaded engagement with bushing 82 that draws the bushing into mated relation with projections 388.

Handle portion 384 may be shaped or marked to indicate the orientation of through-axis 134 of bushing 82 to the surgeon. For example, handle portion 384 may be elongated in transverse cross-section as shown in FIG. 42, in a direction orthogonal to a plane 398 defined collectively by a long axis 400 of driver 380 and projections 388.

VI. METHODS OF FIXING BONE

This section describes exemplary methods of fixing bone with the systems of the present disclosure. The method steps described in this section may be performed in a suitable order and combination, and may be implemented using any suitable combination of the system components of the present disclosure and/or supplemented by any other method steps of the present disclosure.

A bone to be fixed may be selected. The bone may be a long bone or any other suitable bone. Exemplary bones that may be suitable include a leg bone (e.g., a femur, tibia, or fibula), an arm bone (e.g., a humerus, radius, or ulna), or the like. The bone may have any suitable discontinuity, such as at least one fracture, cut, nonunion, or the like. The discontinuity may separate the bone into two or more portions (interchangeably called segments or fragments), which may be fixed relative to one another using the method.

A nail for fixation of the bone may be selected. The nail may have any suitable combination of properties and characteristics as disclosed herein. For example, the length, diameter, longitudinal shape, flexibility, and/or taper, among others, of the nail may be selected according to the bone that was selected and/or the position(s) of the discontinuity. The nail has a lockable section configured to be locked to an anchor. The lockable section may be elongated such that the anchor can be locked to the nail over a continuous range of positions along the lockable section, optionally positions in a leading region of the nail.

A bushing for the nail and a corresponding locking member may be selected. The bushing and locking member may be selected from a set of bushings and locking members of different length. The sizes of the bushing and locking member may be selected based on a measured local width of the bone, such as a local width indicated by a gauge of an instrument engaged with the bone (see below).

The bone may be prepared to receive the nail longitudinally in the medullary canal of the bone. Preparation of the bone may include creating an access opening to the medullary canal from an end region of the bone. The access opening may be created by any suitable technique, such as punching and/or drilling the bone. The medullary canal then may be reamed via the access opening using at least one reamer advanced longitudinally in the medullary canal. The reamer may remove cortical bone to widen the medullary canal, particularly in a shaft region of the medullary canal. In some embodiments, the step of selecting a nail may be performed after reaming the medullary canal, when the size of the medullary canal has been established by reaming. In some embodiments, the step of reaming may be omitted.

An incision may be created through soft tissue to access a region of the selected bone. The position of the incision may be located generally where the nail will be attached to the bone with an anchor. This position may be selected such that the incision overlies an expected location of the lockable section of the nail inside the bone.

An instrument having a clamp portion may be engaged with the bone through the incision to attach the instrument to bone. The instrument may have a guide portion that is coupled to the clamp portion and defines a self-centering guide axis, as described above in Section IV. Jaws of the clamp portion may be engaged with opposite sides of the bone and may be held against the bone using a locking mechanism that prevents the jaws from moving away from one another. The jaws may engage the bone in a plane, and the plane may be transverse, such as substantially orthogonal, to a local long axis of the bone where the jaws contact bone. The step of engaging the bone with the clamp portion may be performed with the nail already located in the medullary canal, to assist fluoroscopic visualization of the prospective installed position of the lockable section of the nail and ensure that the guide axis defined by the instrument will intersect the lockable section. In some embodiments, the position at which the clamp portion is engaged with the bone may be selected by measuring a distance from the end of the bone where the access opening has been created, to estimate where the lockable section of the nail will be located once the nail is inserted into the bone.

A local width of the bone may be measured between the jaws with a gauge of the instrument. The gauge may indicate the local width as a numerical value and/or may indicate a level of risk associated with installing the bushing on the current guide axis. The level of risk may be indicated by color coding of the gauge. If the risk is deemed to be unacceptable, the instrument may be moved to a different position on the bone where the gauge indicates the local width is sufficient and/or the level of risk is deemed to be acceptable.

The position of the instrument, such as its orientation, may be stabilized using one or more wire members, such as K-wires. Each wire member may have a leading end that is passed through a channel defined by the instrument and into and/or through the bone on a trajectory defined by the channel. The trajectory may avoid the medullary canal of the bone and may pass through the bone under or over the medullary canal. In some embodiments, the instrument may be stabilized using two wire members placed on non-parallel trajectories having their closest approach to one another before passing through the bone (e.g., inside the instrument), inside the bone, or after passing through the bone.

A position of the guide axis defined by the instrument may be compared to a position of the nail or a reamer extending along the medullary canal of the bone. The positions of the guide axis and nail may be determined fluoroscopically using a viewing axis substantially in line with the guide axis. A radiopaque region of the guide portion, such as a tube thereof, may be viewed to determine the position of the guide axis (e.g., at the center of a radiolucent channel defined by the tube). The position of the guide axis may be adjusted in a plane orthogonal to the guide axis, to move the guide axis closer to a long axis of the nail or reamer. Adjustment may be performed by rotating the guide portion with respect to the clamp portion of the instrument and/or by adjusting a translational position of the guide portion, among others. The adjustment may improve the alignment of a tip of the nail with the guide axis.

A hole may be formed in the bone on the guide axis. The hole may include a wider hole formed in the near cortex and a narrower hole formed in and/or through the far cortex, with the holes coaxial to one another. The holes may be formed from the guide portion with at least one drill extending through the guide portion. The at least one drill may be a step drill that forms both holes. In some embodiments, the step drill may have a shaft to form the wider hole and a nose to form the narrower hole, and the shaft and nose may bore preferentially in respective opposite rotational directions of the drill. In some embodiments, the at least one drill may be a pair of drills sized to form the respective holes separately. Each drill may be cannulated and may be advanced over a guide wire driven into the bone from the guide portion of the instrument on the guide axis. In some embodiments, the smaller drill of the pair of drills may be a K-wire.

The bushing may be attached to a driver (see Section V) and placed through the guide portion of the instrument and into the hole formed in the bone. The bushing may be driven into the bone with the driver until a shoulder of the bushing bottoms out against the far cortex of the bone. The bushing may be driven by pushing or tapping the bushing into the bone, or by utilizing a thread or thread-like structure of the bushing and rotationally advancing the bushing into the hole until seated. In the seated configuration, a leading portion of the bushing may be located in and/or may extend through the narrower hole. The bushing's orientation about its long axis may need to be adjusted such that the through-axis of the transverse aperture of the bushing is aligned with the long axis of the bone, as indicated by the bushing and/or the driver (e.g., a handle portion thereof).

The nail may be advanced through the transverse aperture of the bushing. Fluoroscopy may be used to assess whether the nail's tip is correctly aligned with the bushing as the tip is approaching the bushing. In some embodiments, the nail may be rotated around its longitudinal axis to improve alignment before insertion of the nail's tip through the transverse aperture (see Section III).

The locking member may be inserted into the bushing to lock the nail to the bushing. The locking member may be advanced through the guide portion of the instrument and into the bushing, while the instrument remains attached to the bone. The bushing's internal bottom wall and/or the tip of the locking member may have features (protrusions) to engage the nail to increase the holding power of the interface.

The nail may be locked to one or more other anchors installed at spaced positions along the nail. The use of more than one anchor may be suitable in some cases to fix more than two segments of the bone created by fractures.

VII. COMPOSITION OF SYSTEM COMPONENTS

The nails, bushings, and locking members disclosed herein may have any suitable composition. Each may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, magnesium or magnesium alloy (e.g., an alloy including magnesium, calcium, and zinc) etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) carbon fiber; or (5) any combination thereof. In exemplary embodiments, each of the nail, the bushing, and the locking member is formed of metal. In exemplary embodiments, the nail is formed of softer metal than the bushing and/or locking member, and/or the bushing is formed of softer metal than the locking member.

VIII. EXAMPLES

The following examples describe selected aspects and embodiments of the present disclosure related to the bone fixation systems, assemblies, devices, and methods of the present disclosure. These examples are included for illustration and are not intended to limit or define the entire scope of the present disclosure. Devices, elements, features, aspects, and/or steps of the systems, assemblies, devices, and methods described in this section may be combined with one another and with any of the devices, elements, features, aspects, and/or steps of the systems, assemblies, devices, and methods described elsewhere in the present disclosure, in any suitable combination.

Example 1

Deformable Anchor

This example describes an exemplary anchor 62' including a bushing 82' that is deformable by a corresponding locking member 84'. This deformation makes locking member 84' more resistant to rotation that would loosen the grip of the anchor on a nail 60, and results in more reliable and stable locking of nail 60 to anchor 62'; see FIGS. 43-50.

Bushing 82' and locking member 84' are similar to bushing 82 and locking member 84 (e.g., see FIGS. 1-20), and may have any suitable combination of features described above in Sections I and II. For example, bushing 82' may have a proximal body 106 forming a shoulder 110 distally, and may have a post 108 projecting axially from shoulder 110. Body 106 may define a transverse aperture 126, such as a slot in the depicted embodiment. The body also may define an axial opening 128, such as an axial bore, that intersects the transverse aperture. An external thread structure 121, such as one or more external threads, may be defined by the exterior of body 106 for attachment of the bushing to bone via threaded engagement. An internal thread 90 may be defined by axial opening 128 inside body 106 for attachment of bushing 82' to locking member 84' by threaded engagement with at least one external thread 92 thereof. Accordingly, locking member 84' may be described as a setscrew. Various differences between anchor 62' of this example and anchor 62 of Section I are described below.

Figure 44:
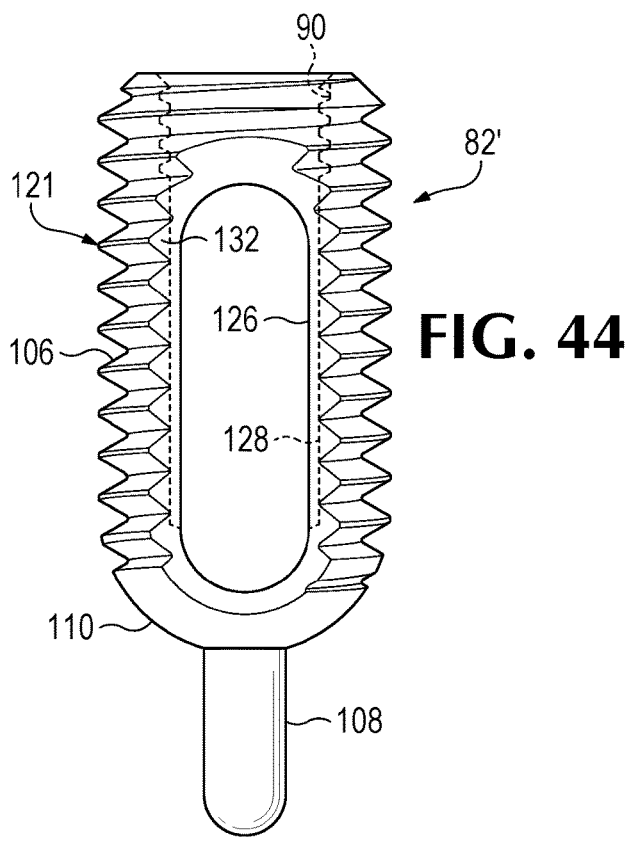
FIG. 44 is a side view of a bushing of the anchor of FIG. 43, viewed parallel to a through-axis defined by a transverse aperture of the bushing.
Figure 45:
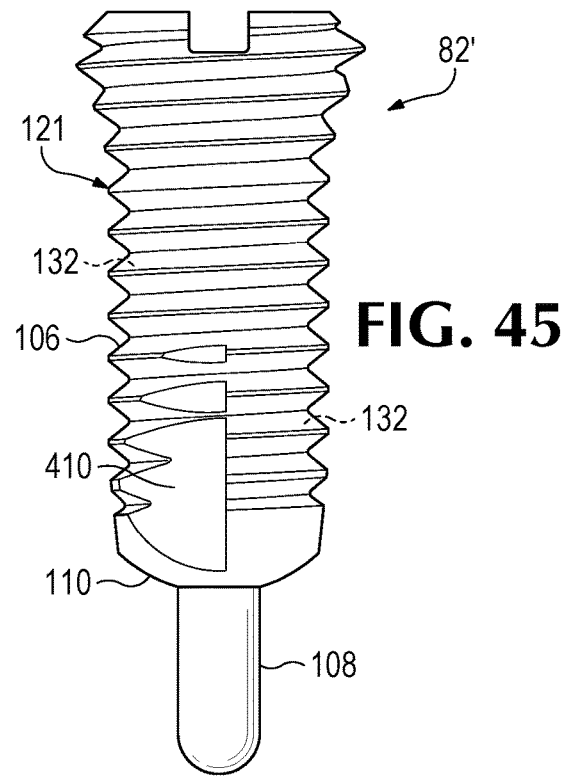
FIG. 45 is a side view of the bushing of FIG. 44 taken orthogonally to the through-axis of the transverse aperture.

External thread structure 121 of bushing 82' may cover a larger area of the radial periphery of body 106 relative to bushing 82 (compare FIGS. 44 and 45 with FIGS. 6 and 7). More specifically, external thread structure 121 may extend along a majority of a complete turn of a helix for each full revolution of the thread(s). Transverse aperture 126 and associated bevels 132 interrupt thread structure 121. The thread structure also may be interrupted by a self-tapping feature 410, such as an axial cutout, to form a complementary, internal thread in bone as the bushing is driven into bone (see FIG. 45). With this thread configuration, bushing 82' is driven into bone predominantly by rotation, and may provide stronger attachment to bone than bushing 82.

Shoulder 110 of bushing 82' may be rounded in profile instead of flat (compare FIGS. 44 and 45 with FIGS. 6 and 7). A rounded shoulder configuration may reduce the amount of cortical bone, if any, that needs to be removed from the inner wall of the far cortex of the bone, relative to a flat shoulder. Accordingly, the rounded shoulder reduces the possibility of weakening or otherwise damaging the far cortex when holes are drilled in the bone for the bushing. The radius of curvature of the shoulder 110 may approximately match, or may be less than, the average radius of curvature of the medullary canal where the bushing is to be installed in the bone.

Figure 46:
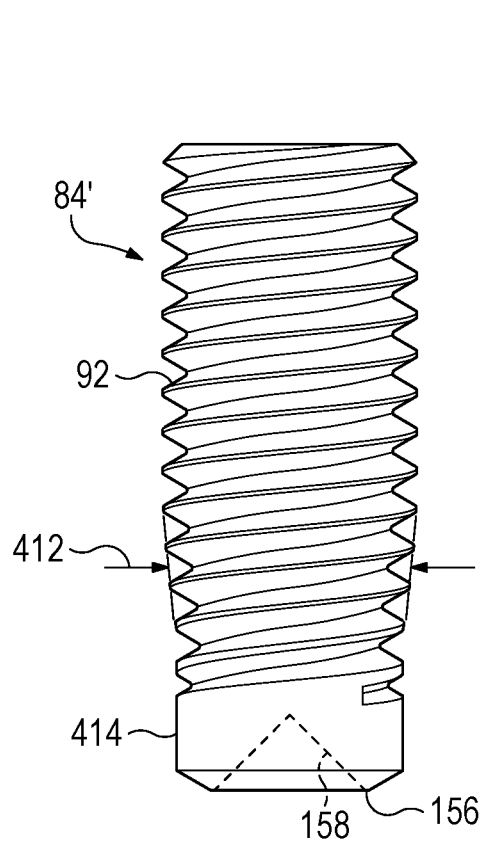
FIG. 46 is a side view of a locking member of the anchor of FIG. 43.
Figure 47:
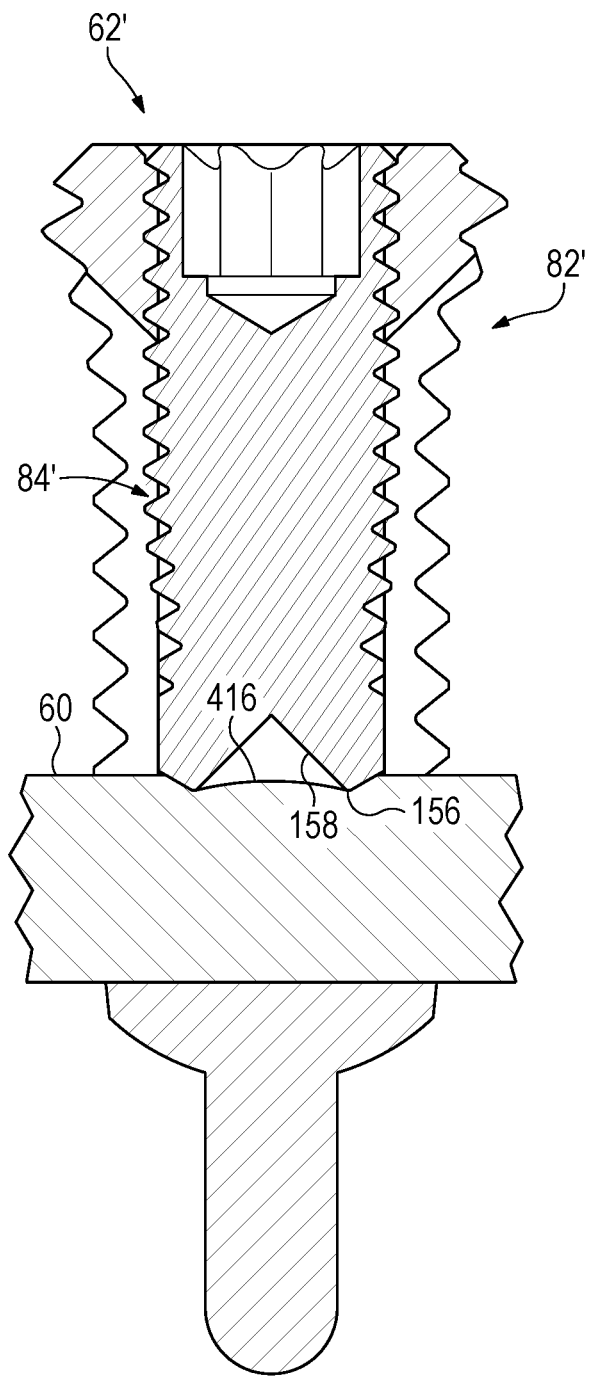
FIG. 47 is a fragmentary, sectional view of the anchor of FIG. 43, taken generally along line 47-47 of FIG. 43 with the anchor encircling and locked to a leading region of the intramedullary nail of FIG. 1.

Locking member 84' may have features that provide tighter threaded engagement with bushing 82' relative to locking member 84 and bushing 82 (compare FIG. 46 with FIGS. 11 and 14). External thread 92 of locking member 84' may extend along a greater length of the locking member, such as more than one-half or three-fourths of the length. Also, a major diameter 412 of external thread 92 may taper distally in a leading end region of locking member 84'. Major diameter 412 may taper to match the diameter of a nonthreaded section 414 located distally of external thread 92. These features may reduce the risk of cross-threading external thread 92 with internal thread 90 of bushing 82', and/or may promote thread-forming in the wall of axial opening 128 by external thread 92, as described further below.

Locking member 84' may have a distal protrusion 156 encircling a depression 158. The distal protrusion of locking member 84' may define a sharper annular rim than on locking member 84 (compare FIGS. 46 and 47 with FIG. 13). The rim may deform a lateral surface region 416 of nail 60 when the distal end of locking member 84' is tightened against the nail (see FIG. 47). This deformation may be encouraged by a difference in hardness between locking member 84' and nail 60. For example, nail 60 and locking member 84' may be composed of a titanium alloy and cobalt-chrome (an alloy of cobalt and chromium), respectively, among others.

Figure 48:
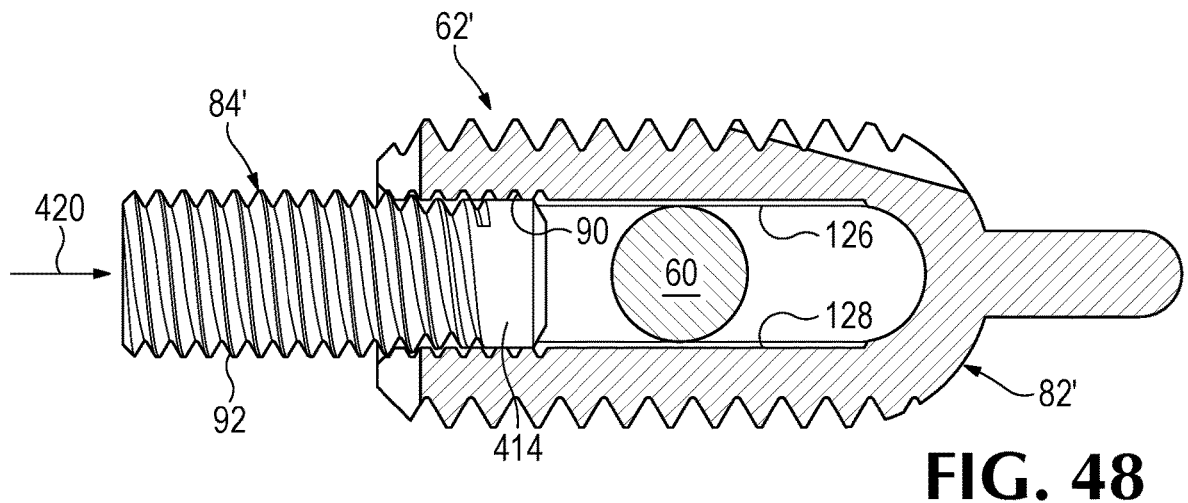
FIG. 48 is a sectional view of the anchor of FIG. 43 at an early stage of assembly, taken generally along line 48-48 of FIG. 43 with a leading region of the intramedullary nail of FIG. 1 extending through the bushing of the anchor, and with the locking member of the anchor advanced only translationally into the axial opening of the bushing and not yet in threaded engagement with the bushing.
Figure 49:
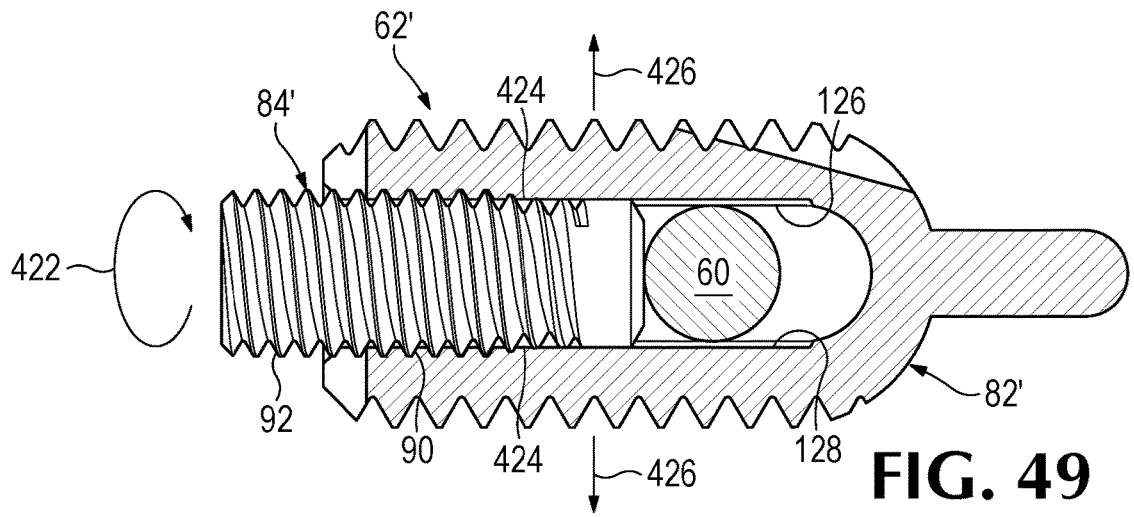
FIG. 49 is another sectional view of the anchor and nail of FIG. 48, taken as in FIG. 48, except with the anchor at an intermediate stage of assembly produced by rotational (threaded) advancement of the locking member into the axial opening of the bushing, such that the nail is pushed partway to the distal end of the bushing's transverse aperture.
Figure 50:
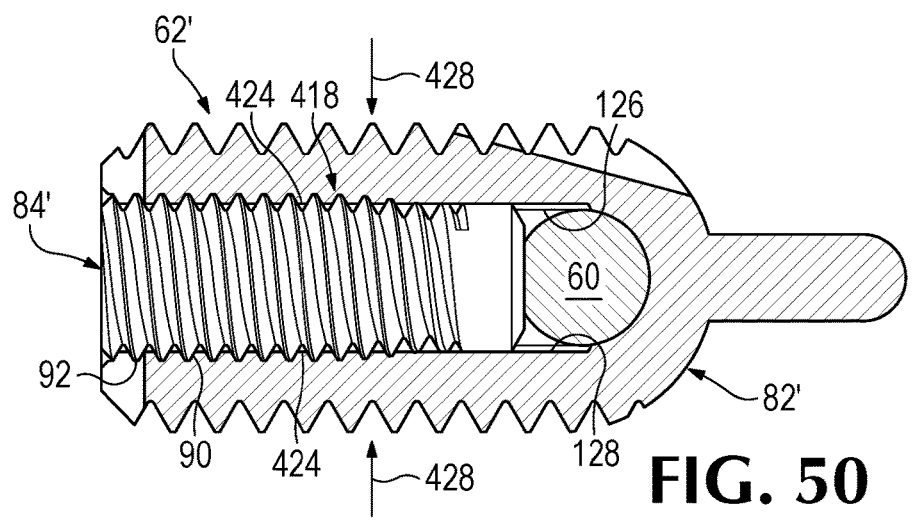
FIG. 50 is another sectional view of the anchor and nail of FIG. 48, taken as in FIG. 49, except with the locking member fully advanced to a seated position that locks the nail to the bushing.
Figure 51:
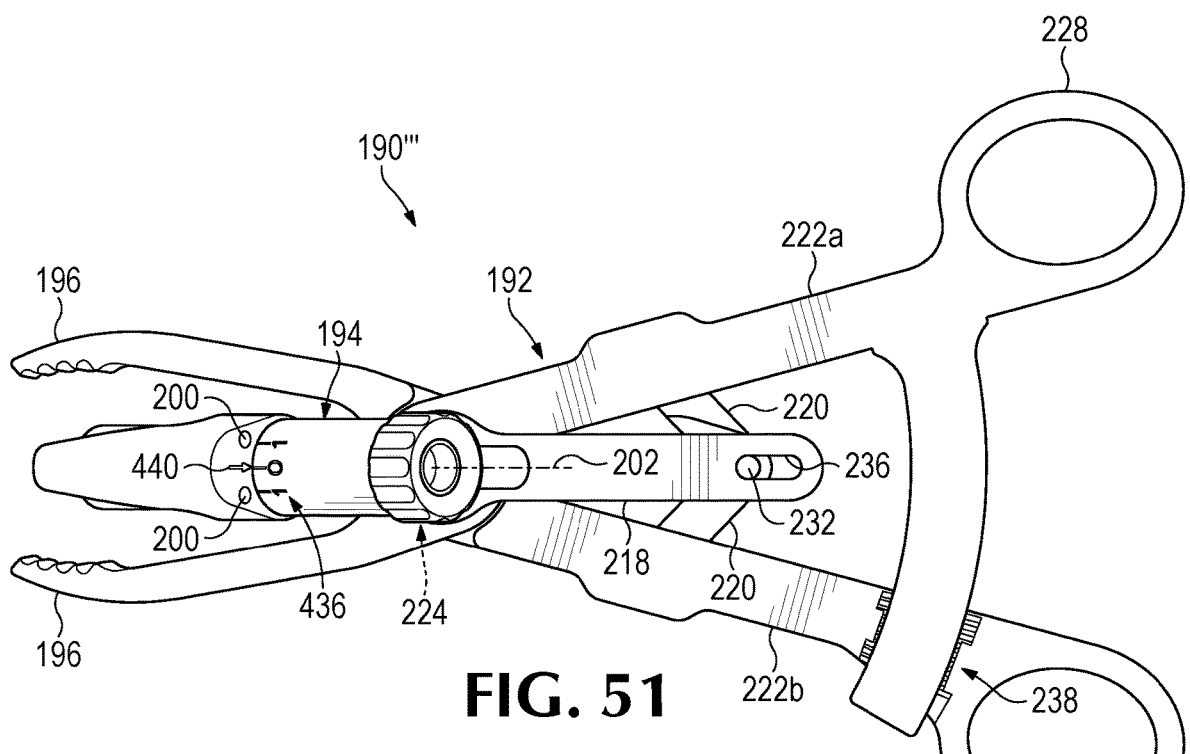
FIG. 51 is a top view of another exemplary instrument to guide installation of a bushing of a nail-encircling anchor, in accordance with aspects of the present disclosure.

FIGS. 48-50 illustrate how locking member 84' may be installed in bushing 82'. This installation urges nail 60 to the distal end of transverse aperture 126 (compare FIG. 48 with FIG. 50), and clamps nail 60 tightly between bushing 82' and locking member 84', optionally with nail 60 deformed by locking member 84', as described above. The installation also may deform the wall of axial opening 128 to form a new internal thread structure 418 inside the bushing. Internal thread structure 418 is a distal extension of internal thread 90. The fit between new internal thread structure 418 and external thread 92 is tight and better resists any tendency for locking member 84' to gradually turn about its long axis and loosen its grip on the nail after installation.

FIG. 48 shows nail 60 extending through bushing 82'. Locking member 84' has been translationally mated with bushing 82', indicated by an arrow at 420. Complementary threads 90, 92 are positioned for rotational mating but are not yet engaged with one another. Nonthreaded section 414 fits closely in axial opening 128 to ensure coaxial alignment of bushing 82' and locking member 84' with one another, which avoids cross-threading.

FIG. 49 shows locking member 84' in threaded engagement with bushing 82' via threads 90, 92 at an intermediate stage of assembly. Locking member 84' has been rotated, indicated by an arrow at 422, to create contact between the distal end of the locking member and nail 60, such that the nail is pushed toward the distal end of transverse aperture 126 as the locking member is advanced further by rotation. Bushing 82' and locking member 84' have an interference fit with one another at this stage of installation, since major diameter 412 of the locking member is larger than a diameter of axial opening 128 distal to internal thread 90 (also see FIG. 46). As a result, locking member 84' applies tension radially outward on opposing walls 424 of axial opening 128, while bushing 82' applies compression radially inward on locking member 84'. In response, bushing 82' may bulge radially outward, indicated by arrows at 426, to slightly increase a width of transverse aperture 126. Alternatively, or in addition, external thread 92 may deform walls 424 to form, or at least begin to form, internal thread structure 418 (also see FIG. 50)

FIG. 50 shows locking member 84' fully advanced by rotation to a seated position that locks nail 60 to bushing 82'. Nail 60 has been pushed into contact with the distal end of transverse aperture 126 and clamped, and optionally deformed, between the bushing and the locking member. Locking member 84' may place bushing 82' under axial tension as the locking member is tightened against nail 60. This tension urges walls 424 radially inward against external thread 92 of locking member 84', indicated by arrows at 428, which may deform walls 424 to form internal thread structure 418. Bushing 82' may be formed of a softer material than locking member 84', such that the bushing is preferentially deformed relative to locking member 84' when internal thread structure 418 is formed. For example, bushing 82' may be composed of a titanium alloy, and locking member may be composed of cobalt-chrome, among others.

Example 2

Instrument with Eccentric Guide Axis

This example describes another exemplary embodiment 190''' of an instrument for fixation system 50 to facilitate installation of bushing 82 (or 82') and/or locking member 84 (or 84') (see Sections I, II, and IV, and Example 1); see FIGS. 51-54.

Instrument 190''' may have any suitable combination of features described elsewhere herein, including a self-centering guide axis 202 with a rotationally-adjustable offset. Instrument 190''' is most similar to instrument 190, and may have a clamp portion 192 connected to a guide portion 194 (see FIG. 51).

Clamp portion 192 may have a pair of levers 222a, 222b that are pivotally connected to one another at a fulcrum 224. The levers form a pair of jaws 196 at one end to grip bone and a pair of handle members 228 at the other end. A locking mechanism 238 structured as a ratchet allows levers 222a, 222b to pivot in a closing direction but not an opening direction of the jaws 196, namely, such that the jaws can pivot toward one another, but not away from one another until teeth and a pawl of the ratchet are disengaged from one another. In some embodiments, the teeth and pawl of the ratchet may be positioned such that the ratchet cannot lock jaws 196 against the bone unless the bone has at least a threshold diameter. The threshold diameter may be selected to ensure the bone is wide enough locally to permit drilling and bushing installation without significant risk of iatrogenically fracturing the bone.

Figure 52:
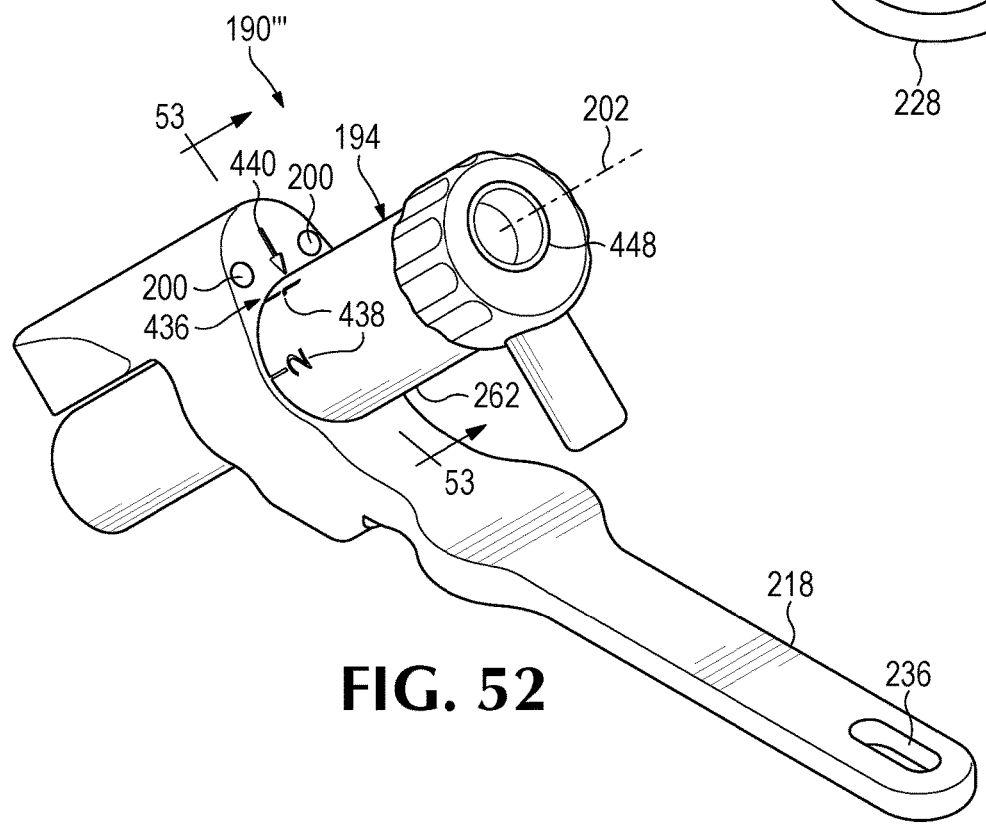
FIG. 52 is a view of a guide portion and holder of the instrument of FIG. 51, taken in isolation from a clamp portion of the instrument.

Guide portion 194 may be connected to clamp portion 192 with a holder 218 (see FIG. 52). Holder 218 may be kept on a central plane of clamp portion 192, as jaws 196 are opened and closed. More specifically, holder 218 may be pivotably connected to clamp portion 192 on the axis of fulcrum 224, and also may be coupled to levers 222a, 222b by a pair of pivotally connected linkage members 220. A pivotable connection 232 between linkage members 220 may slide along a slot 236 defined by holder 218 to keep the holder (and guide portion 194) on the central plane of clamp portion 192. Holder 218 also may define one or more channels 200 for receiving wire members that couple the holder (and thus the instrument) to bone. Each channel may extend from a proximal surface region to a distal end of the holder. The distal end of holder 218 may be configured to contact bone and may be flush with a distal end of guide portion 194. Holder 218 may encircle at least an axial region of the guide portion. Further aspects of the self-centering mechanism for the guide axis, and channels 200, are described above in Section IV.

Figure 53:
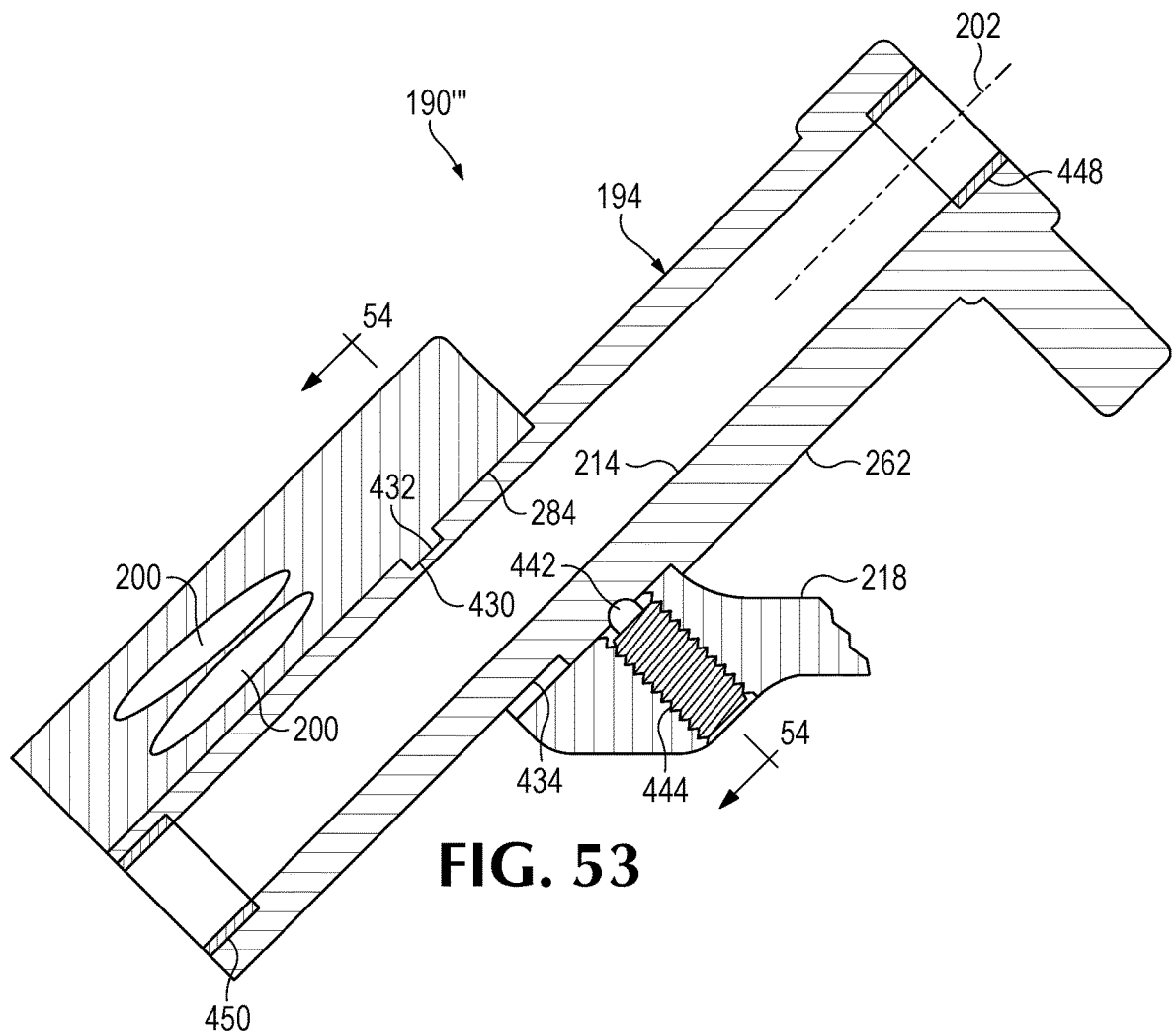
FIG. 53 is a fragmentary, sectional view of the guide portion and holder of FIG. 52, taken generally along line 53-53 of FIG. 52.
Figure 54:
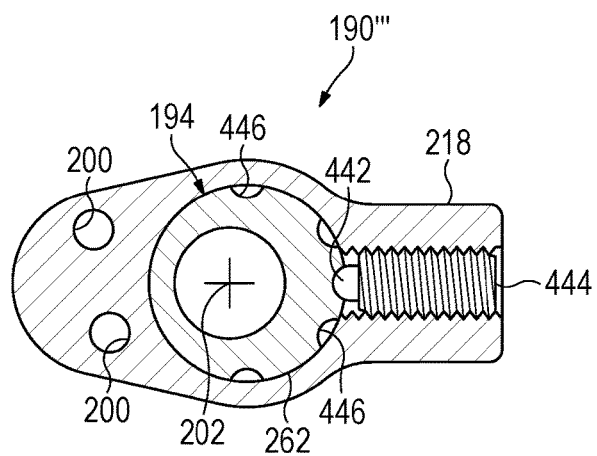
FIG. 54 is another sectional view of the guide portion and holder of FIG. 52, taken generally along line 54-54 of FIG. 53.

Guide portion 194 may be rotatably connected to holder 218 (see FIGS. 52 and 53). The guide portion may include a tube 262 defining an eccentrically located guide channel 214 and a guide axis 202 extending therethrough. Tube 262 may be disposed at least partially in an opening 284 defined by holder 218, and may be connected to the holder by complementary retention features that restrict axial removal of tube 262 from holder 218. In the depicted embodiment, the retention features include a protrusion 430 of holder 218 received in a groove 432 defined by the exterior of tube 262. Groove 432 may extend in circumferential direction around tube 262, to permit rotation of the tube about its central long axis. Groove 432 may open axially at a release site 434, which permits axial removal of tube 262 from holder 218 when release site 434 is rotated into alignment with protrusion 430.

Guide portion 194 and holder 218 collectively may form a gauge 436 to measure and indicate the current offset of guide axis 202 from the central plane of instrument 190''', as determined by the rotational orientation of tube 262 (see FIGS. 51-54). A scale 438 may be displayed by guide portion 194, and an indicator 440 by holder 218, or vice versa (see FIGS. 51 and 52). The scale may have reference marks and/or characters (e.g., letters, numbers, and/or symbols), among others. For example, in the depicted embodiment, scale 438 has the numbers 2, 1, 0, 1, and 2 arranged in this order along a circumferential path on tube 262. Each number represents the distance in millimeters of guide axis 202 from the central plane of instrument 190'''. The numbers are not spaced uniformly; tube 262 is rotated through a larger angle to change the offset from 1 to 2 millimeters relative to 0 to 1 millimeter in either rotational direction.

Guide portion 194 may be movable translationally and/or rotationally to a plurality of predefined offsets of the guide axis from central plane 230. The predefined offsets may be created by features of guide portion 194 and holder 218 that are complementary to one another. For example, guide portion 194 may be retained by complementary features at predefined rotational positions corresponding to the offsets measured by gauge 436 (see FIGS. 53 and 54). A detent 442 may resist rotation of guide portion 194 at each predefined position, and the detent may be released by apply sufficient torque manually to guide portion 194. In the depicted embodiment, detent 442 is a spring-biased ball connected to holder 218 with a screw 444. The exterior of tube 262 defines a plurality of complementary depressions 446 each sized to receive detent 442. (Five depressions 446 are present in the depicted embodiment.) Each depression 446 is located at the same radial orientation as one of the numbers on scale 438.

Instrument 190''' may be formed predominantly of radiolucent material, and may include one or more radiopaque members to permit visualization with fluoroscopy. In the depicted embodiment, the radiopaque members are upper and lower rings 448, 450 each centered on guide axis 202 (see FIG. 53). Rings 448, 450 can be aligned with one another coaxially under fluoroscopy to ensure the viewing axis for fluoroscopy is parallel to guide axis 202, and then can be compared with the position of nail (also see FIG. 29). In exemplary embodiments, rings 448, 450 are formed of metal, and other parts of instrument 190''' are formed of carbon fiber. In some embodiments, the radiopaque members are not centered on guide axis 202 and do not rotate with guide portion 194. For example, the radiopaque members may be mounted to holder 218.

Example 3

Drill Pair for Near Cortex and Far Cortex Hole Formation

This example describes a near-cortex drill 460 and a far-cortex drill 462. This example also describes a two-drill procedure using drills 460, 462 sequentially to form respective holes 160, 161 of different diameter in the near cortex 118 and the far cortex 120 of a bone (e.g., fibula 54), to receive correspondingly-sized regions (provided by body 106 and post 108) of a bushing 82 (or 82'); see FIGS. 55-59.

The two-drill procedure described here may have advantages over a single-drill procedure using drill 204 (see FIG. 21). The single-drill procedure is described in more detail in U.S. patent application Ser. No. 15/728,247, filed Oct. 9, 2017, which is incorporated herein by reference. The advantages of the two-drill procedure may include more reliable formation of narrower hole 161 without excessively weakening or inadvertently over-drilling far cortex 120. The two-drill procedure is enabled by rounded shoulder 110 of bushing 82', which reduces the amount of cortical bone, if any, that needs to be removed from far cortex 120 in order to create a suitable space for receiving shoulder 110.

FIGS. 55 and 57 respectively show near-cortex drill 460 in isolation (FIG. 55) and stopped from further advancement into bone 54 (FIG. 57). Near-cortex drill 460 has a shaft 464 equipped with a distal pointed tip 466. Shaft 464 defines one or more flutes 468 that create at least one cutting edge 470 in a distal boring portion 472 and a proximal boring portion 474 of the drill. The boring portions collectively are configured to bore wider hole 160 through near cortex to receive body 106 of bushing 82 (or 82'). More specifically, distal boring portion 472 forms a narrower hole in near cortex 118 that is reamed by proximal boring portion 474 to create wider hole 160.

A stop member 476 may be located radially outward of shaft 464, and may be formed integrally with or separately from the shaft. If formed separately, stop member 476 may have an adjustable position along shaft 464. The stop member is configured to establish a depth at which near-cortex drill 460 is blocked from further advancement into bone 54. Advancement is blocked by contact between the proximal end of tube 262 of guide portion 194 of any of the clamp/guide instruments disclosed herein, when drilling with near-cortex drill 460 is complete. The axial position of stop member 476 along shaft 464 ensures that further distal travel of drill 460 is blocked after proximal boring portion 474 has bored wider hole 160 completely through near cortex 118, but before the leading end of proximal boring portion 474 reaches far cortex 120 (see FIG. 57). An axial position for the stop member may be selected before or after manufacture of the drill based on a range of bone dimensions present in a population of potential subjects, or based on measurement of at least one bone dimension specific to a particular subject that will receive the bushing. Distal boring portion 472 may or may not bore a far-cortex blind hole 478, depending on whether stop member 476 arrests travel of the drill before the distal boring portion reaches far cortex 120 (see FIG. 57).

FIGS. 56 and 58 respectively show far-cortex drill 462 in isolation (FIG. 56) and stopped from further advancement into bone 54 (FIG. 58). Far-cortex drill 462 has a shaft 480 equipped with a distal pointed tip 482 (e.g., a faceted (trocar) tip). Tip 482 forms a proximal boring portion 484 to bore a narrower hole 161 in/through far cortex 120 (see FIG. 58). Shaft 480 defines one or more flutes 486 that create at least one cutting edge 488 in a proximal reaming portion 490 of the drill. Proximal reaming portion 490 is side-cutting, which allows the reaming portion to efficiently widen a region of medullary canal 64, if needed, to achieve a better fit of rounded shoulder 110 of bushing 82' against the wall of the medullary canal. However, the proximal reaming portion is configured to avoid end-cutting, such that the proximal reaming portion is unable to bore axially into far cortex 120 at narrower hole 161. Accordingly, advancement of far-cortex drill 462 is stopped when the configuration of FIG. 58 is reached. Holes 160, 161 formed by drills 460, 462 are shown in FIG. 59 after removal of drill 462.

Example 4

Selected Embodiments I

This section describes selected embodiments of the present disclosure as a series of indexed paragraphs.

Paragraph A1. A system for bone fixation, comprising: (i) an instrument having a pair of jaws configured to engage opposite sides of a bone, the jaws being coupled to a guide portion defining a guide axis such that the guide axis remains in a central plane that is between and equidistant from the jaws as such jaws are opened and closed; (ii) a bushing configured to be placed transversely into the bone on the guide axis; (iii) a nail configured to be placed longitudinally in a medullary canal of the bone such that the nail extends through the bushing; and (iv) a locking member that locks the nail to the bushing.

Paragraph A2. The system of paragraph A1, further comprising at least one drill, wherein the guide portion is configured to guide drilling of at least one hole in the bone on the guide axis using the at least one drill, and wherein the at least one hole includes a hole having a diameter corresponding to a diameter of the bushing.

Paragraph A3. The system of paragraph A2, wherein the at least one drill is a step drill having a proximal boring portion configured to form a wider hole in a near cortex of the bone and a distal boring portion configured to form a narrower hole in the far cortex of the bone, and wherein the bushing includes a body having a diameter corresponding to the wider hole and a post having a diameter corresponding to the narrower hole.

Paragraph A4. The system of paragraph A2, wherein the at least one drill includes a first drill configured to form a wider hole in a near cortex of the bone, and a second drill configured to form a narrower hole in the far cortex of the bone, and wherein the bushing includes a body having a diameter corresponding to the wider hole and a post having a diameter corresponding to the narrower hole.

Paragraph A5. The system of any of paragraphs A1 to A4, wherein the bushing is configured to be advanced on the guide axis through the guide portion and into the bone.

Paragraph A6. The system of any of paragraphs A1 to A5, wherein the guide portion has a tube defining the guide axis and configured to be movable with respect to the jaws, while the jaws remain engaged with the bone, to offset the guide axis from the central plane.

Paragraph A7. The system of paragraph A6, wherein tube is adjustable to offset the guide axis from the central plane in opposite directions from the central plane.

Paragraph A8. The system of any of paragraphs A1 to A7, wherein the guide portion includes a tube coupled to the jaws via a holder, and wherein the tube is configured to be moved with respect to the holder to offset the guide axis from the central plane.

Paragraph A9. The system of any of paragraphs A1 to A8, wherein jaws are connected to one another at a pivot axis, and wherein the central plane contains the pivot axis.

Paragraph A10. The system of any of paragraphs A1 to A9, wherein the jaws define a plane that is parallel to and spaced from the guide axis.

Paragraph A11. The system of any of paragraphs A1 to A10, wherein the instrument defines a pair of channels configured to receive a pair of wire members and direct the wire members on non-parallel trajectories through the bone, to stabilize the instrument on the bone.

Paragraph A12. The system of paragraph A11, wherein the channels are configured to direct the wire members on trajectories through the bone that avoid the medullary canal thereof.

Paragraph A13. The system of paragraph A11 or A12, wherein the trajectories have their closest approach to one another before reaching the bone.

Paragraph A14. The system of any of paragraphs A1 to A13, wherein the instrument has a gauge that measures a local width of the bone where engaged by the jaws.

Paragraph A15. The system of paragraph A14, wherein the gauge is configured to indicate whether the local width of the bone is sufficient for safe installation of the bushing.

Paragraph A16. The system of paragraph A15, wherein the gauge has color coding to indicate whether the local width of the bone is sufficient.

Paragraph A17. The system of any of paragraphs A1 to A16, further comprising a set of bushings having the same diameter and different length from one another and including the bushing, each bushing of the set defining an aperture through which the nail is configured to extend, the aperture of each bushing having a different size measured parallel to a long axis of the bushing and corresponding to the different length of the bushing.

Paragraph A18. The system of any of paragraphs A1 to A17, further comprising any other limitation(s) of any other indexed paragraph(s) of Section VIII.

Paragraph B1. A method of fixing bone, the method comprising: (i) engaging opposite sides of a bone with jaws of an instrument having a guide portion defining a guide axis, the jaws being coupled or configured to be coupled to the guide portion such that the guide axis remains in a central plane that is between and equidistant from the jaws as such jaws are opened and closed; (ii) boring at least one hole transversely in the bone on the guide axis; (iii) placing a bushing into the bone at the at least one hole; (iv) advancing a nail longitudinally in a medullary canal of the bone such that the nail extends through the bushing; and (v) locking the nail to the bushing.

Paragraph B2. The method of paragraph B1, wherein the jaws define a clamping plane that is orthogonal to the central plane, and parallel to and spaced from the guide axis.

Paragraph B3. The method of paragraph B2, wherein the step of engaging includes a step of orienting the clamping plane substantially orthogonal to a long axis of the bone.

Paragraph B4. The method of any of paragraphs B1 to B3, wherein the jaws are pivotable with respect to one another about a pivot axis defined by the instrument, wherein the pivot axis is oblique to the guide axis, and wherein the step of engaging includes a step of orienting the pivot axis obliquely to a long axis defined by the bone.

Paragraph B5. The method of any of paragraphs B1 to B4, further comprising a step of offsetting the guide axis from the central plane before the step of boring, while the jaws remain engaged with the bone.

Paragraph B6. The method of paragraph B5, further comprising a step of fluoroscopically viewing an alignment between the nail or a reamer and at least part of the guide portion, wherein the step of offsetting the guide axis improves the alignment.

Paragraph B7. The method of paragraph B5 or B6, wherein the step of offsetting includes a step of moving at least part of the guide portion with respect to the jaws such that the guide axis is parallel to and spaced from the central plane.

Paragraph B8. The method of paragraph B7, wherein the step of moving includes a step of rotating at least part of the guide portion with respect to the jaws.

Paragraph B9. The method of paragraph B8, wherein the step of rotating includes a step of rotating at least part of the guide portion about a rotation axis that is parallel to and spaced from the guide axis.

Paragraph B10. The method of paragraph B8, wherein the step of moving includes a step of creating net translational displacement of at least part of the guide portion with respect to the jaws.

Paragraph B11. The method of any of paragraphs B1 to B10, further comprising a step of driving at least one wire member through the bone on a trajectory defined by the instrument, to stabilize the instrument with respect to the bone.

Paragraph B12. The method of paragraph B11, wherein the step of driving includes a step of driving a pair of wire members through the bone on non-parallel trajectories defined by the instrument.

Paragraph B13. The method of paragraph B12, wherein the trajectories have their closest approach to one another before reaching the bone.

Paragraph B14. The method of any of paragraphs B11 to B13, wherein each trajectory is defined by a corresponding channel of the instrument, and wherein each wire member extends through the corresponding channel after the step of driving.

Paragraph B15. The method of any of paragraphs B11 to B14, wherein each wire member is a K-wire.

Paragraph B16. The method of any of paragraphs B1 to B15, further comprising a step of measuring a local width of the bone between the opposite sides engaged by the jaws using a gauge of the instrument.

Paragraph B17. The method of paragraph B16, wherein the gauge indicates the local width numerically and/or as a color.

Paragraph B18. The method of any of paragraphs B1 to B17, further comprising any other limitation(s) of any other indexed paragraph(s) of Section VIII.

Paragraph C1. A system for bone fixation, comprising: (i) an instrument including a pair of jaws configured to engage opposite sides of a bone, and a guide portion coupled to the jaws and defining a guide axis, the instrument being configured to direct a pair of wire members on a pair of non-parallel trajectories through the bone, to stabilize the instrument with respect to the bone; (ii) a bushing configured to be placed transversely in the bone via at least one hole bored in the bone from the guide portion on the guide axis; (iii) a nail configured to be placed longitudinally in a medullary canal of the bone, such that the nail extends through the bushing; and (iv) a locking member configured to lock the nail to the bushing.

Paragraph C2. The system of paragraph C1, wherein the instrument has a pair of channels that define the pair of non-parallel trajectories.

Paragraph C3. The system of paragraph C1 or C2, where the pair of non-parallel trajectories are configured to have a closest approach to one another before reaching the bone.

Paragraph C4. The system of any of paragraphs C1 to C3, wherein the instrument includes a pair of levers pivotably connected to another and forming the jaws, wherein the guide portion is connected to the levers via a holder, and wherein the holder defines each trajectory.

Paragraph C5. The system of paragraph C4, wherein the guide portion includes a tube defining a channel centered on the guide axis, and wherein the holder encircles the tube.

Paragraph C6. The system of any of paragraphs C1 to C5, wherein each trajectory is configured to avoid the medullary canal of the bone.

Paragraph C7. The system of any of paragraphs C1 to C6, further comprising the pair of wire members, wherein each wire member is a K-wire.

Paragraph C8. The system of any of paragraphs C1 to C7, further comprising any other limitation(s) of any indexed paragraph(s) of Section VIII.

Paragraph D1. A method of fixing bone, the method comprising: (i) engaging opposite sides of a bone with jaws of an instrument having a guide portion, the guide portion being coupled to the jaws and defining a guide axis; (ii) driving a pair of wire members into the bone after the step of engaging, such that the wire members extend through the instrument and the bone on non-parallel trajectories defined by the instrument, to stabilize the instrument with respect to the bone; (iii) boring at least one hole in the bone transversely on the guide axis; (iv) placing a bushing into the bone via the at least one hole; (v) advancing a nail longitudinally in a medullary canal of the bone such that the nail extends through the bushing; and (vi) locking the nail to the bushing.

Paragraph D2. The method of paragraph D1, wherein the step of driving includes a step of guiding advancement of each wire member to the bone with a channel defined by the instrument.

Paragraph D3. The method of paragraph D2, wherein the instrument has a pair of levers forming the jaws, wherein the pair of levers are coupled to the guide portion via a holder, and wherein the step of guiding advancement of each wire member includes a step of guiding advancement of the wire member with a channel defined by the holder.

Paragraph D4. The method of any of paragraphs D1 to D3, further comprising any other limitation(s) of any other indexed paragraph(s) of Section VIII.

Paragraph E1. A system for bone fixation, comprising: (i) a nail configured to be placed longitudinally in a medullary canal of a bone; (ii) a bushing having a trailing portion and a leading portion, the trailing portion forming a shoulder adjacent the leading portion and defining a transverse aperture through which the nail is configured to extend, the leading portion being elongated and substantially cylindrical, and (iii) a locking member configured to lock the nail to the bushing.

Paragraph E2. The system of paragraph E1, wherein the trailing portion includes a substantially cylindrical body.

Paragraph E3. The system of paragraph E1 or E2, wherein the trailing portion tapers or ends abruptly to form the shoulder.

Paragraph E4. The system of any of paragraphs E1 to E3, wherein the trailing portion includes one or more lateral protrusions configured to attach the bushing to a near cortex of the bone.

Paragraph E5. The system of paragraph E4, wherein at least one of the lateral protrusions forms at least part of an inlet of the transverse aperture.

Paragraph E6. The system of paragraph E4 or E5, wherein the one or more lateral protrusions form an external thread and/or are configured to function as an external thread.

Paragraph E7. The system of any of paragraphs E4 to E6, wherein the one or more lateral protrusions include a plurality of teeth.

Paragraph E8. The system of paragraph E7, wherein the lateral protrusions form two or more sets of teeth that are circumferentially spaced from one another on the trailing portion, and wherein the teeth of different sets are arranged on a same helical path as one another.

Paragraph E9. The system of paragraph E8, wherein the plurality of teeth includes an axial column of teeth arranged parallel to a long axis of the bushing.

Paragraph E10. The system of any of paragraphs E4 to E9, wherein the one or more lateral protrusions define a plurality of axial columns of teeth.

Paragraph E11. The system of any of paragraphs E1 to E10, wherein the shoulder is spherical or planar.

Paragraph E12. The system of any of paragraphs E1 to E11, wherein the trailing portion of the bushing also defines an axial aperture intersecting the transverse aperture and having an internal thread, and wherein the locking member has an external thread that is complementary to the internal thread.

Paragraph E13. The system of any of paragraphs E1 to E12, wherein a distal end of the bushing is not cylindrical.

Paragraph E14. The system of any of paragraphs E1 to E13, wherein the bushing defines a long axis, and wherein the transverse aperture is elongated parallel to the long axis and has a tapered inlet.

Paragraph E15. The system of any of paragraphs E1 to E14, wherein the transverse aperture has opposite ends that are spaced from one another parallel to a through-axis of the transverse aperture, and wherein each opposite end is beveled circumferentially to form a widened inlet.

Paragraph E16. The system of any of paragraphs E1 to E15, wherein the transverse aperture has an inlet, and wherein the inlet has a length measured parallel to a long axis of the bushing that is at least one-half a length of the trailing portion measured parallel to the long axis.

Paragraph E17. The system of any of paragraphs E1 to E16, wherein the transverse aperture has an inlet, wherein the inlet has a maximum width measured parallel to a diametrical axis of the bushing that is orthogonal to a long axis of the bushing and orthogonal to a through-axis of the aperture, and where the maximum width is at least one-half an average diameter of the trailing portion.

Paragraph E18. The system of any of paragraphs E1 to E17, wherein a leading region of the nail has a main portion defining a long axis and a tip that is offset from the long axis.

Paragraph E19. The system of paragraph E18, wherein the tip is elongated substantially parallel to the long axis of the main portion.

Paragraph E20. The system of paragraph E18 or E19, wherein the main portion has a uniform diameter, and wherein the tip is tapered.

Paragraph E21. The system of any of paragraphs E18 to E20, wherein a trailing region of the nail is curved in a plane, and wherein the tip is offset from the main portion in the plane.

Paragraph E22. The system of any of paragraphs E18 to E21, wherein the tip is less than one-half the length of the main portion.

Paragraph E23. The system of any of paragraphs E1 to E22, wherein the nail had a head and a stem, wherein the head defines a plurality of openings configured to receive fasteners that attach the head to the bone, and wherein the bushing and the locking member configured to attach the stem to the bone.

Paragraph E24. The system of any of paragraphs E1 to E23, further comprising any other limitation(s) of any other indexed paragraph(s) of Section VIII.

Paragraph F1. A method of fixing bone, the method comprising: (i) boring a bone on an axis to form a wider hole through a near cortex and a narrower hole in and/or through a far cortex of the bone; (ii) selecting a bushing having a trailing portion with a diameter corresponding to the wider hole and a leading portion with a diameter corresponding to the narrower hole, the trailing portion forming a shoulder adjacent the leading portion; (iii) driving the bushing as a unit into the bored bone on the axis until the shoulder engages the far cortex to impede further advancement of the bushing; (iv) advancing a nail longitudinally in the medullary canal such that the nail extends through the bushing; and (v) locking the nail to the bushing.

Paragraph F2. The method of paragraph F1, wherein the step of boring a bone includes a step of forming a wider hole that is cylindrical and a narrower hole that is at least partially cylindrical.

Paragraph F3. The method of paragraph F1 or F2, wherein the step of boring a bone is performed with a first drill to form the wider hole and a second drill to form the narrower hole.

Paragraph F4. The method of paragraph F3, further comprising a step of installing a guide wire on the axis before the step of boring, wherein the step of boring is performed over the guide wire using a cannulated first drill and/or a cannulated second drill.

Paragraph F5. The method of paragraph F1 or F2, wherein the step of boring is performed with a step drill that forms the wider hole and the narrower hole.

Paragraph F6. The method of any of paragraphs F1 to F5, wherein the step of boring includes a step of forming a recessed region on the inner side of the far cortex adjacent the narrower hole, and wherein the recessed region is complementary to the trailing portion of the bushing at the shoulder.

Paragraph F7. The method of any of paragraphs F1 to F6, wherein the trailing portion tapers or ends abruptly to form the shoulder.

Paragraph F8. The method of any of paragraphs F1 to F7, wherein the step of driving the bushing includes a step of rotating the bushing more than one full turn about a long axis thereof.

Paragraph F9. The method of any of paragraphs F1 to F8, wherein the trailing portion has one or more lateral protrusions, and wherein the step of driving the bushing includes a step of engaging the near cortex of the bone with the one or more lateral protrusions.

Paragraph F10. The method of paragraph F9, wherein the step of engaging the near cortex includes a step of urging the one or more lateral protrusions into cortical bone at the wider hole.

Paragraph F11. The method of any of paragraphs F1 to F10, wherein the step of driving includes a step of pushing or tapping the bushing to urge the bushing into the bone.

Paragraph F12. The method of any of paragraphs F1 to F11, wherein the nail has a trailing region and a leading region, wherein the step of locking the nail includes a step of clamping a section of the leading region of the nail between the bushing and a locking member, the method further comprising a step of attaching the trailing region of the nail to the bone using one or more fasteners extending into openings defined by the trailing region.

Paragraph F13. The method of paragraph F12, wherein the trailing region forms a wider head, and wherein the leading region forms a narrower stem.

Paragraph F14. The method of any of paragraphs F1 to F13, further comprising any other limitation(s) of any other indexed paragraph(s) of Section VIII.

Paragraph G1. A system for bone fixation, comprising: (i) an instrument having a clamp portion coupled to a guide portion that defines a guide axis, the clamp portion including a pair of jaws configured to engage opposite sides of a bone, wherein the instrument has a gauge that measures a local width of the bone between the jaws; (ii) a bushing configured to be placed transversely into the bone via at least one hole bored in the bone from the guide portion on the guide axis; (iii) a nail configured to be placed longitudinally in a medullary canal of the bone, such that the nail extends through the bushing; and (iv) a locking member configured to lock the nail to the bushing.

Paragraph G2. The system of paragraph G1, wherein the gauge has color coding configured to indicate the local width as one of two or more different colors.

Paragraph G3. The system of paragraph G2, wherein each different color represents a width range, and wherein the width ranges of the two or more different colors do not overlap one another.

Paragraph G4. The system of paragraph G2 or G3, wherein the gauge indicates smaller widths as red and larger widths are green.

Paragraph G5. The system of paragraph G4, wherein the gauge indicates intermediate widths as yellow or orange.

Paragraph G6. The system of paragraph G4 or G5, wherein red corresponds to local widths where installation of the bushing is not advised.

Paragraph G7. The system of any of paragraphs G1 to G6, wherein the gauge includes a graduated scale.

Paragraph G8. The system of paragraph G7, wherein the graduated scale includes one or more numbers indicating the local width according to a standard measurement unit.

Paragraph G9. The system of any of paragraphs G1 to G8, further comprising any other limitation(s) of any other indexed paragraph(s) of Section VIII.

Paragraph H1. A method of fixing bone, the method comprising: (i) engaging opposite sides of a bone with jaws of an instrument having a guide portion, the guide portion being coupled to the jaws and defining a guide axis; (ii) reading a gauge of the instrument, the gauge measuring a local width of the bone between the jaws; (iii) moving the jaws to a different position on the bone if the gauge indicates the local width is too small; (iv) boring at least one hole transversely in the bone on the guide axis; (v) placing a bushing into the bone at the at least one hole; (vi) advancing a nail longitudinally in a medullary canal of the bone such that the nail extends through the bushing; and (vii) locking the nail to the bushing.

Paragraph H2. The method of paragraph H1, wherein the step of reading a gauge includes a step of reading a color from the gauge.

Paragraph H3. The method of paragraph H1 or H2, further comprising any other limitation(s) of any other indexed paragraph(s) of Section VIII.

Paragraph I1. A method of fixing bone, the method comprising: (i) engaging opposite sides of a bone with jaws of an instrument having a guide portion, the guide portion being coupled to the jaws and defining a guide axis; (ii) placing a nail or reamer along a medullary canal of the bone; (iii) determining a degree of alignment of the nail or reamer and the guide portion with one another by fluoroscopy; (iv) repositioning the guide axis, if the degree of alignment is not sufficient, by moving at least part of the guide portion with respect to the jaws while such jaws remain engaged with the bone, to improve the degree of alignment; (v) retracting the nail or reamer; (vi) boring the bone on the guide axis from the guide portion; (vii) placing a bushing into the bored bone; (viii) advancing the nail longitudinally in the medullary canal such that that the nail extends through the bushing; and (ix) locking the nail to the bushing.

Paragraph I2. The method of paragraph I1, Wherein the step of placing a bushing includes a step of passing the bushing through the guide portion on the guide axis.

Paragraph I3. The method of paragraph I1 to I2, further comprising any other limitation(s) of any other indexed paragraph(s) of Section VIII.

Paragraph J1. A system for bone fixation, comprising: (i) a bushing configured to be positioned bicortically in a bone to span a medullary canal thereof, the bushing defining an axial aperture intersecting a transverse aperture; (ii) a nail having a leading region and a trailing region, the nail being configured to be placed along the medullary canal, such that the leading region of the nail extends through the bushing via the transverse aperture, the trailing region defining one or more openings configured to receive fasteners that attach the trailing region to the bone; and (iii) a locking member configured to be received in the axial aperture, to lock the leading region of the nail to the bushing; wherein the leading region of the nail has a main portion and a tip portion, the tip portion being laterally offset from the main portion.

Paragraph J2. The system of paragraph J1, wherein the tip portion is substantially parallel to the main portion.

Paragraph J3. The system of paragraph J1 or J2, wherein the main portion has a uniform diameter, and wherein the tip portion is tapered.

Paragraph J4. The system of any of paragraphs J1 to J3, wherein the trailing portion is curved in a plane, and wherein tip portion is offset from the main portion in the plane.

Paragraph J5. The system of any of paragraphs J1 to J4, wherein the tip portion is less than one-half the length of the main portion.

Paragraph J6. The system of any of paragraphs J1 to J5, further comprising any other limitation(s) of any other indexed paragraph(s) of Section VIII.

Paragraph K1. A method of fixing bone, the method comprising: (i) placing a bushing into a bone such that the bushing spans a medullary canal thereof, the bushing defining an axial aperture intersecting a transverse aperture; (ii) selecting a nail including a leading region and a trailing region, the leading region having a main portion and a tip that is offset from a long axis of the main portion; (iii) advancing the tip along the medullary canal of the bone until the tip approaches the transverse aperture; (iv) rotating the nail about the long axis, if needed, to improve alignment of the tip with the transverse aperture; (v) passing the tip through the transverse aperture; (vi) locking the leading region of the nail to the bushing using a locking member received in the axial aperture of the bushing; and (vii) attaching the trailing region of the nail to the bone.

Paragraph L1. A system for bone fixation, comprising: (i) an instrument having a clamp portion coupled to a guide portion, the guide portion defining a guide axis, the clamp portion including a pair of jaws configured to grip opposite sides of a bone, at least part of the guide portion being configured to be repositioned with respect to the clamp portion, to offset the guide axis, while the jaws remain stationary; (ii) a bushing configured to be placed transversely into the bone (a) through the guide portion on the guide axis, and/or (b) via at least one hole bored in the bone from the guide portion on the guide axis, the bushing defining an aperture; and (iii) a nail configured to be placed along a medullary canal of the bone, such that the nail extends through the aperture of the bushing.

Paragraph L2. The system of paragraph L1, wherein the guide portion defines a channel centered on the guide axis, and wherein the guide portion is radiopaque around the channel.

Example 5

Selected Embodiments II

This section describes further selected embodiments of the present disclosure as a series of indexed paragraphs.

Paragraph 1. A system for bone fixation, comprising: (A) a bushing configured to be placed at least partially into at least one hole bored in a bone; (B) a nail configured to be placed along a medullary canal of the bone such that the nail extends through the bushing; and (C) a locking member configured to lock the nail to the bushing.

Paragraph 2. The system of paragraph 1, further comprising an instrument including a guide portion defining a guide axis and configured to be coupled to a bone such that the guide axis extends across the bone, and wherein the bushing is configured to be placed into the at least one hole bored in the bone along the guide axis.

Paragraph 3. The system of paragraph 2, wherein the instrument includes a pair of jaws, and wherein the jaws are coupled to the guide portion and configured to engage the bone such that the instrument is coupled to the bone, and wherein, optionally, the jaws are movable with respect to one another about a pivot axis.

Paragraph 4. The system of paragraph 3, wherein the guide axis continues to lie in a central plane located between and equidistant from the jaws as the jaws are opened and closed, and wherein, optionally, the jaws are movable with respect to one another about a pivot axis that lies in the central plane.

Paragraph 5. The system of paragraph 3 or paragraph 4, wherein the instrument has a pair of levers that are pivotably connected to one another, wherein the guide portion is coupled to the pair of levers via a holder for the guide portion, wherein the levers are coupled to the holder by respective linkage members that have a pivotable connection to one another, and wherein the pivotable connection of the linkage members moves along a slot defined by the holder when the jaws are opened and closed, thereby ensuring that the guide portion remains equidistant from the jaws, irrespective of the degree of jaw opening.

Paragraph 6. The system of any of paragraphs 3 to 5, wherein the guide portion is configured to be movable from a first position to at least one second position while the jaws remain engaged with the bone, wherein the guide portion is coupled to the jaws in each of the first and second positions, wherein the guide axis in the first position of the guide portion lies in a central plane between the jaws, and wherein the guide axis in each second position of the guide portion is parallel to, but offset from, the central plane and the guide axis in the first position of the guide portion.

Paragraph 7. The system of paragraph 6, wherein the guide portion is configured to be movable from the first position to each second position while the guide portion remains coupled to the jaws.

Paragraph 8. The system of paragraph 6 or 7, wherein the guide portion is movable to at least one third position, and wherein the guide axis in each second position of the guide portion and the guide axis in each third position of the guide portion are parallel to another, but offset from the central plane in opposite directions.

Paragraph 9. The system of any of paragraphs 6 to 8, wherein the guide portion is movable to create a plurality of offsets of the guide axis from the central plane, wherein the guide portion is coupled to the jaws via a holder, and wherein the plurality of offsets are predefined by features of the guide portion and the holder that are complementary to one another.

Paragraph 10. The system of paragraph 9, wherein the plurality of offsets includes predefined offsets that are one millimeter and two millimeters from the central plane.

Paragraph 11. The system of any of paragraphs 6 to 10, wherein the instrument has a gauge to indicate a current offset of the guide axis from the central plane.

Paragraph 12. The system of any of paragraphs 2 to 11, wherein the instrument has a guide portion configured to rotate with respect to the jaws about an axis that is parallel to, but spaced from, the guide axis, to move the guide portion from the first position to each second position.

Paragraph 13. The system of any of paragraphs 2 to 12, wherein the instrument is at least predominantly radiolucent.

Paragraph 14. The system of paragraph 13, wherein the instrument has a guide portion defining the guide axis, and wherein the guide portion includes a radiopaque member centered on the guide axis.

Paragraph 15. The system of paragraph 14, wherein the radiopaque member is a radiopaque ring, and wherein the guide portion includes a pair of radiopaque rings each centered on the guide axis and spaced from one another along the guide axis.

Paragraph 16. The system of any of paragraphs 2 to 15, wherein the instrument defines at least one wire-receiving channel configured to direct a wire member into the bone, to couple the instrument to the bone with the wire member, and wherein, optionally, the instrument defines a pair of wire members configured to direct a pair of wire members on non-parallel trajectories into the bone, to couple the instrument to the bone with each of the wire members.

Paragraph 17. The system of paragraph 16, wherein each wire-receiving channel is configured to direct a wire member on a trajectory through the bone that avoids the space in the medullary canal to be occupied by the nail.

Paragraph 18. The system of paragraph 16 or 17, wherein the instrument includes a pair of levers that are pivotably connected to one another, wherein each lever provides one of the jaws, wherein the guide portion is connected to the levers via a holder for the guide portion, and wherein the holder defines each wire-receiving channel.

Paragraph 19. The system of paragraph 18, wherein a distal end of the guide portion is flush with a distal end of the holder.

Paragraph 20. The system of paragraph 19, wherein the holder has a proximal surface region facing away from the distal end of the holder, and wherein each wire-receiving channel extends through the holder from the proximal surface region to the distal end of the holder.

Paragraph 21. The system of any of paragraphs 18 to 20, wherein the holder encircles at least an axial region of the guide portion.

Paragraph 22. The system of any of paragraphs 16 to 21, wherein the pair of wire-receiving channels are configured such that the non-parallel trajectories have a closest approach to one another before reaching the bone from the instrument.

Paragraph 23. The system of paragraph 22, wherein the pair of wire-receiving channels are configured such that the non-parallel trajectories have a closest approach to one another inside the instrument.

Paragraph 24. The system of any of paragraphs 16 to 23, further comprising the wire member(s), wherein each wire member is a K-wire.

Paragraph 25. The system of any of paragraphs 1 to 24, wherein the at least one hole includes a wider hole and a narrower hole, further comprising one or more drills configured to bore the wider hole along the guide axis in a near cortex of the bone and the narrower hole along the guide axis in a far cortex of the bone, the bushing including a trailing portion having a diameter corresponding to the wider hole and a leading portion having a diameter corresponding to the narrower hole.

Paragraph 26. The system of paragraph 25, wherein the one or more drills include a first drill to bore the wider hole and a second drill to bore the narrower hole.

Paragraph 27. The system of paragraph 26, wherein the first drill includes a boring portion to bore the wider hole and also includes a stop member configured to contact the instrument to prevent axial advancement of the boring portion to the far cortex of the bone.

Paragraph 28. The system of paragraph 26 or 27, wherein the second drill includes a boring portion to bore the narrower hole and a reaming portion to enlarge a region of the medullary canal neighboring the narrower hole.

Paragraph 29. The system of any of paragraphs 1 to 28, wherein the bushing has an external thread structure to engage the bone at a hole of the at least one hole.

Paragraph 30. The system of any of paragraphs 1 to 29, wherein the bushing is configured to be advanced along the guide axis through a guide portion of the instrument and into the bone.

Paragraph 31. The system of any of paragraphs 1 to 30, wherein the bushing includes a body having a shoulder and also includes a post projecting distally from the shoulder.

Paragraph 32. The system of paragraph 31, wherein the shoulder has a rounded profile created by a proximal-to-distal decrease in diameter of a leading end region of the body.

Paragraph 33. The system of paragraph 31 or 32, wherein the post is cylindrical.

Paragraph 34. The system of any of paragraphs 1 to 33, wherein the bushing defines a long axis and also defines a transverse aperture through which the nail is configured to extend, and wherein the transverse aperture is elongated parallel to the long axis of the bushing.

Paragraph 35. The system of paragraph 34, wherein the transverse aperture has a beveled inlet.

Paragraph 36. The system of any of paragraphs 1 to 35, wherein the locking member includes a setscrew having an external thread that is complementary to an internal thread of the bushing.

Paragraph 37. The system of paragraph 36, wherein the bushing defines a transverse aperture and an axial opening that intersect one another, wherein the nail is configured to extend through the transverse aperture, and wherein the setscrew is configured to be advanced into the bushing along the axial opening.

Paragraph 38. The system of paragraph 36 or 37, wherein the setscrew is configured to be disposed in threaded engagement with the bushing and advanced against the nail until the nail is clamped cooperatively by the bushing and the setscrew.

Paragraph 39. The system of paragraph 38, wherein at least one of the bushing and the setscrew has a projection configured to contact and deform a surface region of the nail as the setscrew is being tightened against the nail.

Paragraph 40. The system of paragraph 39, wherein the at least one of the bushing and the setscrew having the projection is composed of a harder material than the nail.

Paragraph 41. The system of paragraph 39 or 40, wherein the setscrew has a projection configured to contact and deform a surface region of the nail, and wherein the projection of the setscrew projects distally from a shaft of the setscrew and forms a distal edge of the setscrew.

Paragraph 42. The system of paragraph 41, wherein the distal edge is annular.

Paragraph 43. The system of any of paragraphs 39 to 42, wherein the bushing has a projection configured to contact and deform a surface region of the nail, and wherein the projection of the bushing is located in a transverse aperture of the bushing.

Paragraph 44. The system of any of paragraphs 36 to 43, wherein the external thread of the setscrew is configured to deform the bushing to create a distal extension of the internal thread in the bushing.

Paragraph 45. The system of paragraph 44, wherein the setscrew is composed of a harder material than the bushing.

Paragraph 46. The system of paragraph 45, wherein each of the bushing and the setscrew is composed of a metal alloy, and wherein the metal alloy of the setscrew is harder than the metal alloy of the bushing.

Paragraph 47. The system of paragraph 46, wherein the setscrew is composed of a cobalt-chrome alloy, and wherein the bushing is composed of a titanium alloy.

Paragraph 48. The system of any of paragraphs 44 to 47, wherein the external thread of the setscrew has a greater axial length than the internal thread of the bushing, before the distal extension of the internal thread is created.

Paragraph 49. The system of any of paragraphs 1 to 48, wherein a leading region of the nail is configured to extend through a transverse aperture of the bushing, wherein the leading region of the nail has an elongated main portion and a distal tip, and wherein the distal tip is radially offset from the main portion.

Paragraph 50. The system of paragraph 49, wherein a central axis of the distal tip is substantially parallel to, and offset from, a longitudinal axis of the main portion.

Paragraph 51. The system of paragraph 49 or 50, wherein the main portion has a uniform diameter, and wherein the tip is tapered.

Paragraph 52. The system of any of paragraphs 49 to 51, wherein a trailing region of the nail is curved in a nail plane, and wherein the tip is offset from the main portion in the nail plane.

Paragraph 53. The system of any of paragraphs 49 to 52, wherein the tip is less than one-half the length of the main portion.

Paragraph 54. The system of any of paragraphs 1 to 53, wherein the guide axis is movable with respect to the bone, to change a transverse position of the guide axis with respect to the bone, while the instrument remains coupled to the bone, wherein, optionally, the guide axis is movable while the bone remains clamped by the instrument and/or remains coupled to the bone with one or more wire members, wherein, optionally, the guide axis is movable from a first position to at least one second position in which the guide axis is parallel to its orientation in the first position, and wherein, optionally, the guide axis is defined by a guide portion that is rotatable to move the guide axis.

Paragraph 55. The system of any of paragraphs 1 to 54, further comprising any limitation or combination of limitations of Examples 4 and 6.

Example 6

Selected Embodiments III

This section describes still further selected embodiments of the present disclosure as a series of indexed paragraphs.

Paragraph 1. A method of fixing bone, the method comprising: (A) selecting an instrument including a pair of jaws and a guide portion defining a guide axis, the guide portion having a self-centering configuration in which the guide axis continues to lie in a central plane located between and equidistant from the jaws as the jaws are opened and closed; (B) engaging a long bone with the jaws such that the guide axis extends across the bone; (C) boring a hole in the bone along the guide axis; (D) placing a bushing at least partially into the hole in the bone; (E) advancing a nail along a medullary canal of the bone such that the nail extends through the bushing; and (F) locking the nail to the bushing.

Paragraph 2. The method of paragraph 1, wherein the step of boring a hole includes boring a wider hole along the guide axis in the near cortex of the bone and a cylindrical, narrower hole along the guide axis in the far cortex of the bone, and wherein the step of placing includes placing a trailing portion of the bushing in the wider hole and a leading portion of the bushing in the narrower hole.

Paragraph 3. The method of paragraph 1 or paragraph 2, wherein the step of placing a bushing includes placing the bushing in threaded engagement with the bone at the hole.

Paragraph 4. The method of any of paragraphs 1 to 3, wherein the step of locking includes gripping the nail cooperatively with the bushing and a setscrew.

Paragraph 5. The method of any of paragraphs 1 to 4, wherein the bushing defines a transverse aperture and an axial opening that intersect one another, wherein the step of advancing a nail includes passing a leading end of the nail through the transverse aperture, and wherein the step of locking includes advancing a setscrew into the bushing along the axial opening.

Paragraph 6. The method of any of paragraphs 1 to 5, wherein the step of placing includes passing the bushing through the guide portion of the instrument along the guide axis.

Paragraph 7. The method of any of paragraphs 1 to 6, wherein the bushing includes a body forming a shoulder and also includes a post projecting distally from the shoulder, and wherein the step of placing a bushing includes advancing the bushing into the bone until contact between the shoulder of the bushing and the far cortex of the bone impedes further advancement.

Paragraph 8. The method of any of paragraphs 1 to 7, further comprising moving the guide portion with respect to the jaws while the jaws remain engaged with the bone, to offset the guide axis from the central plane.

Paragraph 9. The method of paragraph 8, wherein the step of boring a hole is performed along the guide axis with the guide axis offset from the central plane.

Paragraph 10. The method of paragraph 8 or paragraph 9, wherein the step of moving the guide portion includes rotating the guide portion with respect to the jaws about an axis that is parallel to, but offset from, the guide axis.

Paragraph 11. The method of any of paragraphs 1 to 10, further comprising a step of driving a pair of wire members into the bone from the instrument on non-parallel trajectories defined by the instrument, such that each wire member couples the instrument to the bone.

Paragraph 12. The method of paragraph 11, wherein the step of driving a pair of wire members includes passing a leading end of each wire member through a respective wire-receiving channel defined by the instrument and through the bone.

Paragraph 13. A method of fixing bone, the method comprising: (A) engaging opposite sides of a long bone with jaws of an instrument having a guide portion, the guide portion being coupled to the jaws and defining a guide axis extending across the bone; (B) coupling the instrument to the bone with a pair of wire members driven into the bone on non-parallel trajectories defined by the instrument; (C) boring a hole in the bone along the guide axis; (D) placing a bushing at least partially into the hole in the bone; (E) advancing a nail along a medullary canal of the bone such that the nail extends through the bushing; and (F) locking the nail to the bushing.

Paragraph 14. The method of paragraph 13, wherein the step of coupling the instrument includes passing a leading end of each wire member through a wire-receiving channel of the instrument, and wherein the wire-receiving channel defines one of the non-parallel trajectories.

Paragraph 15. The method of paragraph 14, wherein the step of coupling the instrument includes passing the leading end of the wire member through the bone.

Paragraph 16. The method of paragraph 14 or paragraph 15, wherein the instrument includes a pair of levers pivotably connected to each other and forming the jaws, wherein the guide portion is connected to the levers via a holder, and wherein the holder defines each wire-receiving channel.

Paragraph 17. The method of paragraph 16, wherein the holder is in contact with the bone when the step of coupling has been completed.

Paragraph 18. The method of any of paragraphs 13 to 17, wherein the step of coupling the instrument arranges each wire member to extend through a respective wire-receiving channel of the instrument and through the bone.

Paragraph 19. The method of any of paragraphs 13 to 18, where the step of coupling arranges the wire members on non-parallel trajectories having a closest approach to one another before reaching the bone from the instrument.

Paragraph 20. The method of any of paragraphs 13 to 19, wherein each trajectory avoids the medullary canal of the bone.

Paragraph 21. The method of any of paragraphs 13 to 20, wherein each wire member is a K-wire.

Paragraph 22. A system for bone fixation, comprising: (A) a bushing configured to be placed across a medullary canal of a long bone, the bushing including a body and a post, the body having an external thread structure and defining a transverse aperture, the post projecting from a shoulder formed by a leading end region of the body; (B) a nail configured to be placed along the medullary canal of the bone such that the nail extends through the transverse aperture of the bushing; and (C) a setscrew configured to be advanced into the bushing and against the nail, such that the setscrew and the bushing cooperatively grip the nail.

Paragraph 23. The system of paragraph 22, wherein at least one of the bushing and the setscrew has a projection configured to contact and deform a surface region of the nail when the setscrew is advanced into the bushing and against the nail.

Paragraph 24. The system of paragraph 23, wherein the at least one of the bushing and the setscrew having the projection is composed of a harder material than the nail.

Paragraph 25. The system of paragraph 23 or paragraph 24, wherein the setscrew has a projection configured to contact and deform a surface region of the nail, and wherein the projection of the setscrew projects distally from a shaft of the setscrew and forms a distal edge of the setscrew.

Paragraph 26. The system of paragraph 25, wherein the distal edge is annular.

Paragraph 27. The system of any of paragraphs 23 to 26, wherein the bushing has a projection configured to contact and deform a surface region of the nail, and wherein the projection of the bushing is formed by a wall of the transverse aperture.

Paragraph 28. The system of any of paragraphs 22 to 27, wherein the setscrew is composed of a harder material than the bushing, wherein the setscrew has an external thread that is complementary to an internal thread of the bushing, and wherein the external thread of the setscrew is configured to form a distal extension of the internal thread of the bushing when the setscrew is advanced into the bushing and against the nail.

Paragraph 29. The system of paragraph 28, wherein the setscrew is composed of a harder metal alloy, and wherein the bushing is composed of a softer metal alloy.

Paragraph 30. The system of paragraph 29, wherein the harder metal alloy is a cobalt-chrome alloy, and wherein the softer metal alloy is a titanium alloy.

Paragraph 31. The system of any of paragraphs 22 to 30, wherein the post is cylindrical.

Paragraph 32. The system of any of paragraphs 22 to 31, wherein the shoulder has a rounded profile created by a proximal-to-distal decrease in diameter of the leading end region of the body.

Paragraph 33. The system of any of paragraphs 22 to 32, wherein the bushing defines a long axis, and wherein the transverse aperture is elongated parallel to the long axis and has a beveled inlet.

Paragraph 34. A method of fixing bone, the method comprising: (A) boring a wider hole through a near cortex of a long bone and a narrower hole in a far cortex of the bone; (B) selecting a bushing having a body with a diameter corresponding to the wider hole and a post with a diameter corresponding to the narrower hole, the post projecting from a shoulder formed by a leading end region of the body; (C) driving the bushing into the wider and narrower holes until contact between the shoulder and the far cortex of the bone impedes further advancement of the bushing; (D) advancing a nail along the medullary canal such that the nail extends through the bushing; and (E) locking the nail to the bushing.

Paragraph 35. The method of paragraph 34, wherein each of the wider hole and the narrower hole is cylindrical.

Paragraph 36. The method of paragraph 34 or paragraph 35, wherein the step of boring is performed with a first drill to form the wider hole and a second drill to form the narrower hole.

Paragraph 37. The method of any of paragraphs 34 to 36, wherein the step of boring includes forming a recessed region in the far cortex of the bone, and wherein the recessed region is complementary to the shoulder of the bushing.

Paragraph 38. The method of any of paragraphs 34 to 37, wherein the step of driving disposes the bushing in threaded engagement with the bone.

Paragraph 39. The method of any of paragraphs 34 to 38, wherein the step of locking the nail includes a step of clamping an axial region of the nail between the bushing and a setscrew.

Paragraph 40. The method of paragraph 39, wherein the bushing has an internal thread that is complementary to an external thread of the bushing, further comprising a step of forming a distal extension of the internal thread of the bushing using the external thread of the setscrew.

Paragraph 41. The method of paragraph 40, wherein the setscrew is formed of a harder material than the bushing.

Paragraph 42. The method of paragraph 41, wherein the setscrew is formed of a cobalt-chrome alloy, and wherein the bushing is formed of a titanium alloy.

Paragraph 43. A method of fixing bone, the method comprising: (A) engaging a bone with jaws of an instrument having a guide portion, the guide portion being coupled to the jaws and defining a guide axis that extends across the bone; (B) placing a nail or reamer along a medullary canal of the bone; (C) determining a degree of alignment of the nail or reamer and the guide portion with one another by fluoroscopy; (D) repositioning the guide axis, if the degree of alignment is not sufficient, by moving the guide portion with respect to the jaws while the jaws remain engaged with the bone, to improve the degree of alignment; (E) retracting the nail or reamer; (F) boring a hole in the bone along the guide axis from the guide portion; (G) placing a bushing at least partially into the hole in the bone; (H) advancing the nail along the medullary canal such that that the nail extends through the bushing; and (I) locking the nail to the bushing.

Paragraph 44. The method of paragraph 43, wherein the step of placing a bushing includes passing the bushing through the guide portion along the guide axis.

Paragraph 45. A system for bone fixation, comprising: (A) a bushing configured to be positioned bicortically in a bone to transversely a medullary canal of the bone, the bushing defining an axial opening intersecting a transverse aperture; (B) a nail having a leading region and a trailing region, the nail being configured to be placed along the medullary canal such that the leading region of the nail extends through the transverse aperture, the trailing region defining one or more openings configured to receive fasteners that attach the trailing region to the bone; and (C) a locking member configured to be threaded into the axial opening of the bushing and advanced against the nail, to lock the leading region of the nail to the bushing; wherein the leading region of the nail has an elongated main portion and a distal tip, and wherein the tip is radially offset from the main portion.

Paragraph 46. The system of paragraph 45, wherein a central axis of the tip is substantially parallel to, and offset from, a longitudinal axis of the main portion.

Paragraph 47. The system of paragraph 45 or paragraph 46, wherein the main portion has a uniform diameter, and wherein the tip is tapered.

Paragraph 48. The system of any of paragraphs 45 to 47, wherein the trailing region is curved in a plane, and wherein the tip is offset from the main portion in the plane.

Paragraph 49. The system of any of paragraphs 45 to 48, wherein the tip is less than one-half the length of the main portion.

Paragraph 50. A method of fixing bone, the method comprising: (A) placing a bushing at least partially into a bone such that the bushing transversely spans a medullary canal of the bone, the bushing defining an axial opening intersecting a transverse aperture; (B) selecting a nail including a leading region and a trailing region, the leading region having a main portion and a tip, the tip being radially offset from a longitudinal axis of the main portion; (C) advancing the tip along the medullary canal of the bone until the tip approaches the transverse aperture; (D) rotating the nail about the long axis, if needed, to improve alignment of the tip with the transverse aperture; (E) passing the tip through the transverse aperture; (F) locking the leading region of the nail to the bushing using a locking member received in the axial opening of the bushing; and (G) attaching the trailing region of the nail to the bone.

Paragraph 51. A system for bone fixation, comprising: (A) a nail configured to be placed along a medullary canal of a bone; (B) a bushing having an external thread structure to engage bone, the bushing defining a transverse aperture through which the nail is configured to extend and also defining an axial opening having an internal thread; and (C) a setscrew having an external thread configured to be disposed in threaded engagement with the internal thread of the bushing and advanced while in threaded engagement until the nail is gripped cooperatively by the bushing and the setscrew; wherein the setscrew has an interference fit in the bushing such that advancement of the setscrew forms a distal extension of the internal thread at the axial opening of the bushing.

Paragraph 52. The system of paragraph 51, wherein the setscrew is composed of a harder material than the bushing.

Paragraph 53. The system of paragraph 52, wherein the setscrew is composed of a cobalt-chrome alloy, and wherein the bushing is composed of a titanium alloy.

Paragraph 54. The system of any of paragraphs 51 to 53, wherein external thread of the setscrew has a greater axial length than the internal thread of the bushing.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated. Finally, the present disclosure incorporates material by reference. If any ambiguity or conflict in the meaning of a term results from this incorporation by reference, the literal contents of the application govern construction of the term.

We claim:

1. A system for bone fixation, comprising:
an instrument defining a guide axis and configured to be coupled to a bone such that the guide axis extends across the bone;
a bushing configured to be placed at least partially into at least one hole bored in the bone along the guide axis;
a nail configured to be placed along a medullary canal of the bone such that the nail extends through the bushing; and
a locker configured to lock the nail to the bushing,
wherein the instrument includes:
a guide portion defining the guide axis; and
one or more wire-receiving channels, wherein the one or more wire-receiving channels are separate from the guide portion,
wherein the one or more wire-receiving channels are configured to receive one or more wire members and direct the one or more wire members into the bone, to couple the instrument to the bone with the one or more wire members,
wherein the one or more wire-receiving channels are configured to direct a leading end of the one or more wire members on a trajectory through the bone that avoids the space in the medullary canal to be occupied by the nail,
wherein the one or more wire-receiving channels comprise:
a first wire-receiving channel having a first trajectory and configured to receive a first wire member; and
a second wire-receiving channel having a second trajectory and configured to receive a second wire member,
wherein a portion of the first trajectory overlaps with a portion of the second trajectory when viewed from the top of the instrument.

2. The system of claim 1, wherein the instrument includes a pair of jaws, wherein the jaws are coupled to the guide portion and configured to engage the bone such that the instrument is coupled to the bone.

3. The system of claim 2, wherein the guide axis continues to lie in a central plane located between and equidistant from the jaws as the jaws are opened and closed.

4. The system of claim 2, wherein the instrument has a pair of levers that are pivotably connected to one another, wherein the guide portion is coupled to the pair of levers via a holder for the guide portion, wherein the levers are coupled to the holder by respective linkage members that have a pivotable connection to one another, and wherein the pivotable connection of the linkage members moves along a slot defined by the holder when the jaws are opened and closed, thereby ensuring that the guide portion remains equidistant from the jaws, irrespective of the degree of jaw opening.

5. The system of claim 2, wherein the guide portion is configured to be movable from a first position to at least one second position while the jaws remain engaged with the bone, wherein the guide portion is coupled to the jaws in each of the first position and the at least one second position, wherein the guide axis in the first position lies in a central plane between the jaws, and wherein the guide axis in each of the at least one second position is parallel to, but offset from, the central plane and the guide axis in the first position.

6. The system of claim 5, wherein the guide portion is configured to be movable from the first position to each of the at least one second position while the guide portion remains coupled to the jaws.

7. The system of claim 5, wherein the guide portion is configured to rotate with respect to the jaws about an axis that is parallel to, but spaced from, the guide axis, to move the guide portion from the first position to each of the at least one second position.

8. The system of claim 1, wherein the bushing has an external thread structure to engage the bone at a hole of the at least one hole.

9. The system of claim 1, wherein the bushing includes a body having a shoulder and also includes a post projecting distally from the shoulder.

10. The system of claim 9, wherein the post is cylindrical.

11. The system of claim 1, wherein the locker includes a setscrew having an external thread that is complementary to an internal thread of the bushing, and wherein the setscrew is configured to be disposed in threaded engagement with the bushing and advanced against the nail until the nail is clamped cooperatively by the bushing and the setscrew.

12. The system of claim 11, wherein at least one of the bushing and the setscrew has a projection configured to contact and deform a surface region of the nail as the setscrew is being tightened against the nail.

13. The system of claim 11, wherein the external thread of the setscrew is longer than the internal thread of the bushing, wherein the setscrew is composed of a harder material than the bushing, and wherein the external thread of the setscrew is configured to deform the bushing to create a distal extension of the internal thread in the bushing.

14. The system of claim 1, wherein a leading region of the nail is configured to extend through a transverse aperture of the bushing, wherein the leading region of the nail has an elongated main portion and a distal tip, and wherein the distal tip is radially offset from the main portion.

15. The system of claim 1, wherein the portion of the first trajectory overlapped with the portion of the second trajectory is disposed within the first wire-receiving channel, and the portion of the second trajectory overlapped with the portion of the first trajectory is disposed within the second wire-receiving channel.

16. A system for bone fixation, comprising:
an instrument defining a guide axis and configured to be coupled to a long bone such that the guide axis extends across the bone;
a bushing configured to be placed across a medullary canal of the long bone, the bushing including a body and a post, the body having an external thread structure and defining a transverse aperture, the post projecting from a shoulder provided by a leading end region of the body;

a nail configured to be placed along the medullary canal of the long bone such that the nail extends through the transverse aperture of the bushing; and a setscrew configured to be advanced into the bushing and against the nail, such that the setscrew and the bushing cooperatively grip the nail, wherein the instrument includes:
   a guide portion defining the guide axis; and
   one or more wire-receiving channels, wherein the one or more wire-receiving channels are separate from the guide portion, wherein the one or more wire-receiving channels are configured to receive one or more wire members and direct the one or more wire members into the bone, to couple the instrument to the long bone with the one or more wire members, wherein the one or more wire-receiving channels are configured to direct a leading end of the one or more wire members on a trajectory through the long bone that avoids the space in the medullary canal to be occupied by the nail, wherein the one or more wire-receiving channels comprise:
   a first wire-receiving channel having a first trajectory and configured to receive a first wire member; and
   a second wire-receiving channel having a second trajectory and configured to receive a second wire member, wherein a portion of the first trajectory overlaps with a portion of the second trajectory when viewed from the top of the instrument.

17. The system of claim 16, wherein the portion of the first trajectory overlapped with the portion of the second trajectory is disposed within the first wire-receiving channel, and the portion of the second trajectory overlapped with the portion of the first trajectory is disposed within the second wire-receiving channel.

18. A method of fixing bone, the method comprising:
selecting an instrument defining a guide axis;
coupling the instrument to a bone such that the guide axis extends across the bone;
boring at least one hole in the bone along the guide axis;
placing a bushing at least partially into the at least one hole in the bone;
advancing a nail along a medullary canal of the bone such that the nail extends through the bushing; and
locking the nail to the bushing,
wherein the instrument includes:
   a guide portion defining the guide axis; and
   one or more wire-receiving channels, wherein the one or more wire-receiving channels are separate from the guide portion, wherein the one or more wire-receiving channels are configured to receive one or more wire members and direct the one or more wire members into the bone, to couple the instrument to the bone with the one or more wire members, wherein the one or more wire-receiving channels are configured to direct a leading end of the one or more wire members on a trajectory through the bone that avoids the space in the medullary canal to be occupied by the nail, wherein the one or more wire-receiving channels comprise:
   a first wire-receiving channel having a first trajectory and configured to receive a first wire member; and
   a second wire-receiving channel having a second trajectory and configured to receive a second wire member, wherein a portion of the first trajectory overlaps with a portion of the second trajectory when viewed from the top of the instrument.

19. The method of claim 18, wherein the instrument includes a pair of jaws, wherein the step of coupling includes engaging the bone with the jaws, and wherein the guide axis continues to lie in a central plane located between and equidistant from the jaws as the jaws are opened and closed.

20. The method of claim 18, wherein the portion of the first trajectory overlapped with the portion of the second trajectory is disposed within the first wire-receiving channel, and the portion of the second trajectory overlapped with the portion of the first trajectory is disposed within the second wire-receiving channel.

* * * * *